US011726081B2

United States Patent
Sachs et al.

(10) Patent No.: US 11,726,081 B2
(45) Date of Patent: Aug. 15, 2023

(54) METHODS TO IDENTIFY MODULATORS OF TAU PROTEIN STRUCTURE

(71) Applicant: REGENTS OF THE UNIVERSITY OF MINNESOTA, Minneapolis, MN (US)

(72) Inventors: Jonathan N. Sachs, Minneapolis, MN (US); Chih Hung Lo, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 546 days.

(21) Appl. No.: 16/790,486

(22) Filed: Feb. 13, 2020

(65) Prior Publication Data

US 2020/0264162 A1    Aug. 20, 2020

Related U.S. Application Data

(60) Provisional application No. 62/806,345, filed on Feb. 15, 2019.

(51) Int. Cl.
  *G01N 33/50*    (2006.01)
  *G01N 33/68*    (2006.01)
  *G01N 21/64*    (2006.01)

(52) U.S. Cl.
  CPC ....... *G01N 33/502* (2013.01); *G01N 21/6486* (2013.01); *G01N 33/6896* (2013.01)

(58) Field of Classification Search
  CPC ............. G01N 33/502; G01N 21/6486; G01N 33/6896
  See application file for complete search history.

(56) References Cited

U.S. PATENT DOCUMENTS

| | | |
|---|---|---|
| 6,816,102 B2 | 11/2004 | Pavicic |
| 7,157,566 B2 | 1/2007 | Tsien et al. |
| 7,413,862 B2 | 8/2008 | van Dongen et al. |
| 7,674,584 B2 | 3/2010 | Briggs et al. |
| 7,888,090 B2 | 2/2011 | Barnikow et al. |
| 8,957,029 B2 | 2/2015 | Wedlich-Söldner et al. |
| 9,255,128 B2 | 2/2016 | Wedlich-Soldner et al. |
| 9,693,954 B2 | 7/2017 | Mooney et al. |

(Continued)

FOREIGN PATENT DOCUMENTS

| | | |
|---|---|---|
| CN | 108267435 | 7/2018 |
| EP | 2294159 | 3/2011 |

(Continued)

OTHER PUBLICATIONS

Akoury et al., Inhibition of tau filament formation by conformational modulation. *J Am Chem Soc* 135, 2853-2862 (2013).

(Continued)

*Primary Examiner* — Jamil Ahmed
(74) *Attorney, Agent, or Firm* — Mueting Raasch Group

(57) ABSTRACT

The present disclosure provides methods for identifying compounds that cause structural changes in tau protein monomer and oligomer conformation. The methods include the use of cells that include tau proteins labeled with one or more chromophores, and exposing the cells to a test compound. The method further includes detecting a change in fluorescence resonance energy transfer (FRET) between the chromophores.

20 Claims, 36 Drawing Sheets

(56) References Cited

U.S. PATENT DOCUMENTS

| | | |
|---|---|---|
| 10,794,898 B2 | 10/2020 | Thomas et al. |
| 11,345,964 B2 | 5/2022 | Albitar et al. |
| 11,360,096 B2 | 6/2022 | Pack et al. |
| 2003/0059835 A1 | 3/2003 | Tsien et al. |
| 2004/0023874 A1 | 2/2004 | Burgess et al. |
| 2006/0003420 A1 | 1/2006 | Tsien et al. |
| 2006/0068414 A1 | 3/2006 | Kennedy et al. |
| 2006/0094101 A1 | 5/2006 | Yannoni et al. |
| 2006/0134644 A1 | 6/2006 | Hartel et al. |
| 2007/0207532 A1 | 9/2007 | Barnikow et al. |
| 2008/0064054 A1 | 3/2008 | Fernandez-Salas et al. |
| 2011/0126305 A1 | 5/2011 | Chang |
| 2011/0165593 A1 | 7/2011 | Barnikow et al. |
| 2012/0021926 A1 | 1/2012 | Thomas et al. |
| 2013/0231262 A1 | 9/2013 | Robia |
| 2013/0272966 A1 | 10/2013 | Xiong et al. |
| 2014/0039156 A1 | 2/2014 | Lasmezas et al. |
| 2015/0020487 A1 | 1/2015 | Scott et al. |
| 2015/0113671 A1 | 4/2015 | Wedlich-Soldner et al. |
| 2015/0204847 A1* | 7/2015 | Thomas ............. G01N 21/6408 435/29 |
| 2015/0309054 A1 | 10/2015 | Diamond et al. |
| 2015/0369740 A1 | 12/2015 | Cohen et al. |
| 2018/0238901 A1 | 8/2018 | Schaaf et al. |
| 2019/0353663 A9 | 11/2019 | Schaaf et al. |
| 2020/0264162 A1 | 8/2020 | Sachs et al. |
| 2020/0393445 A1 | 12/2020 | Avery et al. |
| 2021/0255195 A1 | 8/2021 | Schaaf et al. |

FOREIGN PATENT DOCUMENTS

| | | |
|---|---|---|
| WO | WO 2009/156019 | 12/2009 |
| WO | 2010/085514 | 7/2010 |
| WO | WO 2015/052331 | 4/2015 |

OTHER PUBLICATIONS

Alonso et al., Promotion of hyperphosphorylation by frontotemporal dementia tau mutations, *J. Biol. Chem.* 2004, 279(33):34873-81.

Avila et al., Role of tau protein in both physiological and pathological conditions. *Physiol Rev* 84, 361-384 (2004).

Baggett et al., The Rational Discovery of a Tau Aggregation Inhibitor. *Biochemistry* 57, 6099-6107 (2018).

Ballatore et al., Tau-mediated neurodegeneration in Alzheimer's disease and related disorders. *Nat Rev Neurosci* 8, 663-672 (2007).

Berger et al., Accumulation of pathological tau species and memory loss in a conditional model of tauopathy. *J Neurosci* 27, 3650-3662 (2007).

Birmingham et al., Statistical methods for analysis of high-throughput RNA interference screens. *Nat Methods* 6, 569-575 (2009).

Bramblett et al., Abnormal tau phosphorylation at Ser396 in Alzheimer's disease recapitulates development and contributes to reduced microtubule binding. *Neuron* 10, 1089-1099 (1993).

Breuzard et al., Molecular mechanisms of Tau binding to microtubules and its role in microtubule dynamics in live cells. *J Cell Sci* 126, 2810-2819 (2013).

Brunden et al., Advances in tau-focused drug discovery for Alzheimer's disease and related tauopathies. *Nat Rev Drug Discov* 8, 783-793 (2009).

Bubber et al., Mitochondrial abnormalities in Alzheimer brain: mechanistic implications. *Ann Neurol* 57, 695-703 (2005).

Chen et al., Fluorescence Self-Quenching from Reporter Dyes Informs on the Structural Properties of Amyloid Clusters Formed in Vitro and in Cells. *Nano Lett* 17, 143-149 (2017).

Chirita et al., Triggers of full-length tau aggregation: a role for partially folded intermediates. *Biochemistry* 44, 5862-5872 (2005).

Chu et al., The influence of 5-lipoxygenase on Alzheimer's disease-related tau pathology: in vivo and in vitro evidence. *Biol Psychiatry* 74, 321-328 (2013).

Chun et al., Activation of glycogen synthase kinase 3beta promotes the intermolecular association of tau. The use of fluorescence resonance energy transfer microscopy. *J Biol Chem* 282, 23410-23417 (2007).

Combs et al., Pseudohyperphosphorylation has differential effects on polymerization and function of tau isoforms. *Biochemistry* 50, 9446-9456 (2011).

Cowan et al., Are tau aggregates toxic or protective in tauopathies? *Front Neurol* 4, 114(2013).

Cowan et al., What is the pathological significance of tau oligomers? *Biochem Soc Trans* 40, 693-697 (2012).

Cummings et al., Alzheimer's disease drug development pipeline: 2018. *Alzheimers Dement (N Y)* 4, 195-214 (2018).

De Calignon et al., Caspase activation precedes and leads to tangles. *Nature* 464, 1201-1204 (2010).

Devi et al., Heterogeneity of Alzheimer's disease: consequence for drug trials? *Alzheimers Res Ther* 10, 122 (2018).

Di Primio et al., The Distance between N and C Termini of Tau and of FTDP-17 Mutants is Modulated by Microtubule Interactions in Living Cells. Frontiers in Molecular Neuroscience 10, (2017). https://www.ncbi.nlm.nih.gov/pmc/articles/PMC5492851.

Dujardin et al., Different tau species lead to heterogeneous tau pathology propagation and misfolding, *Acta Neuropathol Commun* 6, 132 (2018).

Ebneth et al., Overexpression of tau protein inhibits kinesin-dependent trafficking of vesicles, mitochondria, and endoplasmic reticulum: implications for Alzheimer's disease. *J Cell Biol* 143, 777-794 (1998).

Elbaum-Garfinkle et al., Identification of an aggregation-prone structure of tau. *J Am Chem Soc* 134, 16607-16613 (2012).

Ferrari et al., beta-Amyloid induces paired helical filament-like tau filaments in tissue culture. *J Biol Chem* 278, 40162-40168 (2003).

Flach et al., Tau oligomers impair artificial membrane integrity and cellular viability. *J Biol Chem* 287, 43223-43233 (2012).

Gauthier et al., Efficacy and safety of tau-aggregation inhibitor therapy in patients with mild or moderate Alzheimer's disease: a randomised, controlled, double-blind, parallel-arm, phase 3 trial. *Lancet* 388, 2873-2884 (2016).

Gendron et al., The role of tau in neurodegeneration. *Mol Neurodegener* 4, 13 (2009).

Gerson et al., Advances in therapeutics for neurodegenerative tauopathies: moving toward the specific targeting of the most toxic tau species. *ACS Chem Neurosci* 5, 752-769 (2014).

Gerson et al., Potential mechanisms and implications for the formation of tau oligomeric strains. *Crit Rev Biochem Mol Biol* 51, 482-496 (2016).

Ghetti et al., Invited review: Frontotemporal dementia caused by microtubule-associated protein tau gene (MAPT) mutations: a chameleon for neuropathology and neuroimaging. *Neuropathol Appl Neurobiol* 41, 24-46 (2015).

Giacobini et al., Alzheimer disease therapy—moving from amyloid-beta to tau. *Nat Rev Neurol* 9, 677-686 (2013).

Gotz et al., What Renders TAU Toxic. *Front Neurol* 4, 72 (2013).

Gruber et al., Discovery of enzyme modulators via high-throughput time-resolved FRET in living cells. *J Biomol Screen* 19, 215-222 (2014).

Guzman-Martinez et al., Tau oligomers as potential targets for Alzheimer's diagnosis and novel drugs. *Front Neurol* 4, 167 (2013).

Holmes et al., Proteopathic tau seeding predicts tauopathy in vivo. *Proc Natl Acad Sci U S A* 111, E4376-4385 (2014).

Huang et al., Probing Conformational Dynamics of Tau Protein by Hydrogen/Deuterium Exchange Mass Spectrometry. *J Am Soc Mass Spectrom* 29, 174-182 (2018).

Hubscher et al., Generation of transgenic mice expressing FRET biosensors. *Methods Mol Biol* 1294, 117-129 (2015).

Iqbal et al., Hyperphosphorylation-induced tau oligomers. *Front Neurol* 4, 112 (2013).

Jeganathan et al., Global hairpin folding of tau in solution. *Biochemistry* 45, 2283-2293 (2006).

Kadavath et al., Tau stabilizes microtubules by binding at the interface between tubulin heterodimers. *Proc Natl Acad Sci U S A* 112, 7501-7506 (2015).

Kfoury et al., Trans-cellular propagation of Tau aggregation by fibrillar species. *J Biol Chem* 287, 19440-19451 (2012).

(56) References Cited

OTHER PUBLICATIONS

Khan et al., Tau: The Center of a Signaling Nexus in Alzheimer's Disease. *Front Neurosci* 10, 31 (2016).
Kjaergaard et al., Oligomer Diversity during the Aggregation of the Repeat Region of Tau. *ACS Chem Neurosci* 9, 3060-3071 (2018).
Klegeris et al., Toxicity of human monocytic THP-1 cells and microglia toward SH-SY5Y neuroblastoma cells is reduced by inhibitors of 5-lipoxygenase and its activating protein FLAP. *J Leukoc Biol* 73, 369-378 (2003).
Ko et al., Cellular Models for Tau Filament Assembly. *J Mole Neurosci* 19, 311-316 (2003).
Kolarova et al., Structure and pathology of tau protein in Alzheimer disease. *Int J Alzheimers Dis* 2012, 731526 (2012) doi:10.1155/2012/731526.
Kopeikina et al., Soluble forms of tau are toxic in Alzheimer's disease. *Transl Neurosci* 3, 223-233 (2012).
Kovacs, Invited review: Neuropathology of tauopathies: principles and practice. *Neuropathol Appl Neurobiol* 41, 3-23 (2015).
Kuret et al., Evaluating triggers and enhancers of tau fibrillization. *Microsc Res Tech* 61, 141-155 (2005).
Lasagna-Reeves et al., Identification of oligomers at early stages of tau aggregation in Alzheimer's disease. *FASEB J* 26, 1946-1959 (2012).
Lee et al., Three Dimensional Human Neuro-Spheroid Model of Alzheimer's Disease Based on Differentiated Induced Pluripotent Stem Cells. *PLoS One* 11, e0163072 (2016).
Li et al., Deletions of the Aequorea victoria green fluorescent protein define the minimal domain required for fluorescence. *J Biol Chem* 212, 28545-28549 (1997).
Lo Cascio et al., Azure C Targets and Modulates Toxic Tau Oligomers. *ACS Chem Neurosci* 9, 1317-1326 (2018).
Lo et al., Discovery of Novel Small-Molecule Inhibitor of Tau Oligomerization by FRET-Based High-Throughput Screening, Poster, 1 page, Sep. 24, 2018.
Lo et al., Manipulation of Tau Oligomerization and Aggregation Characterized by Time-Resolved FRET, *2906-Pos Board B114*, Feb. 2, 2018, pp. 585a-586a.
Lo et al., Manipulation of Tau Oligomerization and Aggregation Characterized by Time-Resolved FRET, *2906-Pos Board B114*, Poster, 1 page, Feb. 21, 2018.
Lo et al., Targeting the ensemble of heterogeneous tau oligomers in cells: A novel small molecule screening platform for tauopathies. *Alzheimers Dement* 15, 1489-1502 (2019).
Lo et al., Noncompetitive inhibitors of TNFR1 probe conformational activation states. *Sci Signal* 12, (2019).
Lo et al., An Innovative High-Throughput Screening Approach for Discovery of Small Molecules That Inhibit TNF Receptors. *SLAS Discov* 22, 950-961 (2017).
Lutz et al., Novel approach for accurate tissue-based protein colocalization and proximity microscopy. *Sci Rep* 7, 2668 (2017).
Macdonald et al., Assembly of transgenic human P301S Tau is necessary for neurodegeneration in murine spinal cord. *Acta Neuropathol Commun* 7, 44 (2019).
Maeda et al., Increased levels of granular tau oligomers: an early sign of brain aging and Alzheimer's disease. *Neurosci Res* 54, 197-201 (2006).
Majid et al., In vivo axonal transport deficits in a mouse model of fronto-temporal dementia. *Neuroimage Clin* 4, 711-717 (2014).
Mancini et al., 5-Lipoxygenase-activating protein is the target of a novel hybrid of two classes of leukotriene biosynthesis inhibitors. *Mol Pharmacol* 41, 267-272 (1992).
Medina, An Overview on the Clinical Development of Tau-Based Therapeutics. *Int J Mol Sci* 19, (2018).
Mirbaha et al., Inert and seed-competent tau monomers suggest structural origins of aggregation. *Elife* 7, (2018).
Mondragon-Rodriguez et al., Phosphorylation of tau protein as the link between oxidative stress, mitochondrial dysfunction, and connectivity failure: implications for Alzheimer's disease. *Oxid Med Cell Longev* 2013, 940603 (2013).
Moussaud et al., Alpha-synuclein and tau: teammates in neurodegeneration? *Mol Neurodegener* 9, 43 (2014).
Muraya et al., Benzbromarone Attenuates Oxidative Stress in Angiotensin II- and Salt-Induced Hypertensive Model Rats. *Oxid Med Cell Longev* 2018, 7635274 (2018).
Muretta et al., High-performance time-resolved fluorescence by direct waveform recording. *Rev Sci Instrum* 81, 103101 (2010).
Nath et al., The conformational ensembles of alpha-synuclein and tau: combining single-molecule FRET and simulations. *Biophys J* 103, 1940-1949 (2012).
Nouar et al., FRET and FRAP imaging: approaches to characterise tau and stathmin interactions with microtubules in cells. *Biol Cell* 105, 149-161 (2013).
Orr et al., A Brief Overview of Tauopathy: Causes, Consequences, and Therapeutic Strategies. *Trends Pharmacol Sci* 38, 637-648 (2017).
Ozsoy et al., Oxidative stress promotes ligand-independent and enhanced ligand-dependent tumor necrosis factor receptor signaling. *J Biol Chem* 283, 23419-23428 (2008).
Petersen et al., Fluorescence lifetime plate reader: resolution and precision meet high-throughput. *Rev Sci Instrum* 85, 113101 (2014).
Polanco et al., Extracellular Vesicles Isolated from the Brains of rTg4510 Mice Seed Tau Protein Aggregation in a Threshold-dependent Manner. *J Biol Chem* 291, 12445-12466 (2016).
Raja et al., Self-Organizing 3D Human Neural Tissue Derived from Induced Pluripotent Stem Cells Recapitulate Alzheimer's Disease Phenotypes. *PLoS One* 11, e0161969 (2016).
Rane et al., Curcumin Inhibits Tau Aggregation and Disintegrates Preformed Tau Filaments in vitro, *J Alzheimers Dis* 60, 999-1014 (2017).
Rhein et al., Amyloid-beta and tau synergistically impair the oxidative phosphorylation system in triple transgenic Alzheimer's disease mice. *Proc Natl Acad Sci U S A* 106, 20057-20062 (2009).
Rodriguez et al., Structure of the toxic core of alpha-synuclein from invisible crystals. *Nature* 525, 486-490 (2015).
Romo et al., Minimal Nucleation State of alpha-Synuclein Is Stabilized by Dynamic Threonine-Water Networks. *ACS Chem Neurosci* 8, 1859-1864 (2017).
Sahara et al., Assembly of tau in transgenic animals expressing P301L tau: alteration of phosphorylation and solubility. *J Neurochem* 83, 1498-1508 (2002).
Sahara et al., Tau oligomerization: a role for tau aggregation intermediates linked to neurodegeneration. *Curr Alzheimer Res* 5, 591-598 (2008).
Santacruz et al., Tau suppression in a neurodegenerative mouse model improves memory function. *Science* 309, 476-481 (2005).
Saunders et al. "Characterization of a tau FRET biosensor sensitive to tau intramolecular folding." Program No. 048.14. 2018 Neuroscience Meeting Planner. San Diego, CA: Society for Neuroscience, 2018, Online. Nov. 3, 2018.
Schaaf et al., Red-Shifted FRET Biosensors for High-Throughput Fluorescence Lifetime Screening, *Biosensors (Basel)* 8, (2018).
Schaaf et al., High-Throughput Spectral and Lifetime-Based FRET Screening in Living Cells to Identify Small-Molecule Effectors of SERCA. *SLAS Discov* 22, 262-273 (2017).
Schaaf et al., Spectral Unmixing Plate Reader: High-Throughput, High-Precision FRET Assays in Living Cells. *SLAS Discov* 22, 250-261 (2017).
Schulz et al., A new link to mitochondrial impairment in tauopathies. *Mol Neurobiol* 46, 205-216 (2012).
Sharma et al., Tau monomer encodes strains. *Elife* 7, (2018).
Shin et al., Visualization of Tau(−)Tubulin Interaction in a Living Cell Using Bifluorescence Complementation Technique. *Int J Mol Sci* 19, 2978 (2018).
Squire et al., Red-edge anisotropy microscopy enables dynamic imaging of homo-FRET between green fluorescent proteins in cells. *J Struct Biol* 147, 62-69 (2004).
Sultana et al., Oxidative modification of brain proteins in Alzheimer's disease: perspective on future studies based on results of redox proteomics studies. *J Alzheimers Dis* 33 Suppl 1, S243-251 (2013).
Tak et al., Bimolecular fluorescence complementation; lighting-up tau-tau interaction in living cells. *PLoS One* 8, e81682 (2013).

(56) References Cited

OTHER PUBLICATIONS

Taniguchi et al., Inhibition of heparin-induced tau filament formation by phenothiazines, polyphenols, and porphyrins. *J Biol Chem* 280, 7614-7623 (2005).
Theillet et al., Structural disorder of monomeric alpha-synuclein persists in mammalian cells. *Nature* 530, 45-50 (2016).
Timm et al., Microtubule affinity regulating kinase activity in living neurons was examined by a genetically encoded fluorescence resonance energy transfer/fluorescence lifetime imaging-based biosensor: inhibitors with therapeutic potential. *J Biol Chem* 286, 41711-41722 (2011).
Tramier et al., Sensitivity of CFP/YFP and GFP/mCherry pairs to donor photobleaching on FRET determination by fluorescence lifetime imaging microscopy in living cells. *Microsc Res Tech* 69, 933-939 (2006).
Tramier et al., Fluorescence anisotropy imaging microscopy for homo-FRET in living cells. *Methods Cell Biol* 85, 395-414 (2008).
Tuttle et al., Solid-state NMR structure of a pathogenic fibril of full-length human alpha-synuclein, *Nat Struct Mol Biol* 23, 409-415 (2016).
Valentin et al., Photoconversion of YFP into a CFP-like species during acceptor photobleaching FRET experiments. *Nat Methods* 2, 801 (2005).
Valera et al., Modulation of 5-lipoxygenase in proteotoxicity and Alzheimer's disease. *J Neurosci* 33, 10512-10525 (2013).
Verheyen et al., Using Human iPSC-Derived Neurons to Model TAU Aggregation, *PLoS One* 10, e0146127 (2015).
Vunnam et al., Soluble Extracellular Domain of Death Receptor 5 Inhibits TRAIL-Induced Apoptosis by Disrupting Receptor-Receptor Interactions. *J Mol Biol* 429, 2943-2953 (2017).
Wang et al., Triclosan Enhances the Clearing of Pathogenic Intracellular Salmonella or Candida albicans but Disturbs the Intestinal Microbiota through mTOR-Independent Autophagy. *Front Cell Infect Microbiol* 8, 49 (2018).
Wang et al., Binding and neurotoxicity mitigation of toxic tau oligomers by synthetic heparin like oligosaccharides. *Chem Commun (Camb)* 54, 10120-10123 (2018).
Wang et al., Tau in physiology and pathology. *Nat Rev Neurosci* 17, 22-35 (2016).
Ward et al., Tau oligomers and tau toxicity in neurodegenerative disease. *Biochem Soc Trans* 40, 667-671 (2012).
Weaver et al., Conformational change as one of the earliest alterations of tau in Alzheimer's disease. *Neurobiol Aging* 21, 719-727 (2000).
Weissmann et al., Microtubule binding and trapping at the tip of neurites regulate tau motion in living neurons. *Traffic* 10, 1655-1668 (2009).
Wischik et al., Selective inhibition of Alzheimer disease-like tau aggregation by phenothiazines. *Proc Natl Acad Sci U S A* 93, 11213-11218 (1996).
Wittmann et al., Tauopathy in *Drosophila*: neurodegeneration without neurofibrillary tangles. *Science* 293, 711-714 (2001).
Wobst et al., The green tea polyphenol (−)-epigallocatechin gallate prevents the aggregation of tau protein into toxic oligomers at substoichiometric ratios. *FEBS Lett* 589, 77-83 (2015).
Wood et al., Neurofibrillary tangles of Alzheimer disease share antigenic determinants with the axonal microtubule-associated protein tau (tau). *Proc Natl Acad Sci U S A* 83, 4040-4043 (1986).
Xia et al., Impaired tau-microtubule interactions are prevalent among pathogenic tau variants arising from missense mutations. *J Biol Chem* 294, 18488-18503 (2019).
Xiao et al., Recent Advances on Small-Molecule Survivin Inhibitors. *Curr Med Chem* 22, 1136-1146 (2015).
Yasar et al., Antihypertensive drugs decrease risk of Alzheimer disease: Ginkgo Evaluation of Memory Study. *Neurology* 81, 896-903 (2013).
Yoshiyama et al., Synapse loss and microglial activation precede tangles in a P301S tauopathy mouse model. *Neuron* 53, 337-351 (2007).
Zacharias et al., Partitioning of lipid-modified monomeric GFPs into membrane microdomains of live cells. *Science* 296, 913-916 (2002).
Zhang et al., A Simple Statistical Parameter for Use in Evaluation and Validation of High Throughput Screening Assays. *J Biomol Screen* 4, 67-73 (1999).
Zhang et al., In-Cell NMR Study of Tau and MARK2 Phosphorylated Tau. *Int J Mol Sci* 20, (2018).
Zhao et al., A role of P301L tau mutant in anti-apoptotic gene expression, cell cycle and apoptosis. *Mol Cell Neurosci* 24, 367-379 (2003).
Zhao et al., Caspase-2 cleavage of tau reversibly impairs memory. *Nat Med* 22, 1268-1276 (2016).
Zigoneanu et al., Interaction of alpha-synuclein and a cell penetrating fusion peptide with higher eukaryotic cell membranes assessed by (1)(9)F NMR. *Mol Pharm* 9, 1024-1029 (2012).
Acker et al., Considerations for the design and reporting of enzyme assays in high-throughput screening applications, Perspect Sci, May 2014;1(1-6):56-73.
Ai et al., Ca2+/calmodulin-dependent protein kinase modulates cardiac ryanodine receptor phosphorylation and sarcoplasmic reticulum Ca2+ leak in heart failure, CircRes, 2005;97:1314-1322.
Akrap et al., Forster distances for fluorescence resonant energy transfer between mCherry and other visible fluorescent proteins. Anal Biochem 402, 105-106 (2010).
Amin et al., Oncogene Overdose: Too Much of a Bad Thing for Oncogene-Addicted Cancer Cells. Biomark Cancer 7, 25-32 (2015).
Andersson et al., Leaky ryanodine receptors in beta-sarcoglycan deficient mice: A potential common defect in muscular dystrophy, Skelet Muscle, 2012;2:9.
Aracena et al., Effects of S-Glutathionylation and S-Nitrosylation on Calmodulin Binding to Triads and FKBP12 Binding to Type 1 Calcium Release Channels, Antioxid Redox Signal, 2005;7:870-881.
Arbabian et al., Endoplasmic reticulum calcium pumps and cancer, Biofactors, 2011;37:139-149.
Ariazi et al., Estrogen-related receptors as emerging targets in cancer and metabolic disorders Curr Top Med Chem, 2006;6:203-215.
Arnou et al., The Plasmodium falciparum Ca(2+)-ATPase PfATP6: insensitive to artemisinin, but a potential drug target, Biochem Soc Trans, 2011;39:823-831.
Asakura et al., Isolation and characterization of a novel actin filament-binding protein from *Saccharomyces cerevisiae*. Oncogene 16, 121-130 (1998).
Ausuebel, R.M., Current Protocols in Molecular Biology, 1994.
Avery et al., A human beta-III-spectrin spinocerebellar ataxia type 5 mutation causes high-affinity F-actin binding, Sci Rep 6, 21375 (2016).
Avery et al., beta-III-spectrin spinocerebellar ataxia type 5 mutation reveals a dominant cytoskeletal mechanism that underlies dendritic arborization. Proc Natl Acad Sci U S A 114, E9376-E9385 (2017).
Avery et al., Structural basis for high-affinity actin binding revealed by a beta-III-spectrin SCA5 missense mutation. Nat Commun 8, 1350 (2017).
Babaoglu et al., Comprehensive mechanistic analysis of hits from high-throughput and docking screens against beta-lactamase. J Med Chem 51, 2502-2511 (2008).
Bagshaw et al., ATP analogues at a glance, J Cell Science, Feb. 1, 2001;114(3):459-460.
Balog et al., AmJPhysiolHeartCircPhysiol., 2006;290:H794-H799.
Balshaw et al., Calmodulin Binding and Inhibition of Cardiac Muscle Calcium Release Channel (Ryanodine Receptor), JBiolChem, 2001;276;20144-20153.
Balshaw et al., Modulation of intracellular calcium-release channels by calmodulin, J Membr Biol., 2002;185:1-8.
Banerjee et al., Proteoliposome as the model for the study of membrane-bound enzymes and transport proteins, Molecular and Cellular Biochemistry, 1983;50:3-15.
Bañuelos et al., Structural comparisons of calponin homology domains: implications for actin binding. Structure 6, 1419-1431 (1998).
Beechem et al., Numer Comput Methods, 1992;210;37.

(56) References Cited

OTHER PUBLICATIONS

Bers, Cardiac excitation-contraction coupling, Nature, 2002;415:198-205.
Bers, Cardiac Sarcoplasmic Reticulum Calcium Leak: Basis and Roles in Cardiac Dysfunction, AnnuRevPhysiol, Feb. 2014;76:107-127.
Bers et al., Ratio of ryanodine to dihydropyridine receptors in cardiac and skeletal muscle implications forE-C coupling, Am J Physiol, 1993;264:C1587-C1593.
Bers, Macromolecular complexes regulating cardiac ryanodine receptor function, JMolCellCardiol, 2004;37:417-429.
Bers, Ryanodine receptor S2808 phosphorylation in heart failure: smoking gun or red herring, CircRes, 2012;110:796-799.
Boraso et al., AmJPhysiol., 1994;267:H1010-1016.
Bossuyt et al., Spatiotemporally Distinct Protein Kinase D Activation in Adult Cardiomyocytes in Response to Phenylephrine and Endothelin, J Biol Chem, Sep. 23, 2011;286(38):33390-33400.
Bubb et al., Swinholide A is a microfilament disrupting marine toxin that stabilizes actin dimers and severs actin filaments. J Biol Chem 270, 3463-3466 (1995).
Burk et al., Spinocerebellar ataxia type 5: clinical and molecular genetic features of a German kindred. Neurology 62, 327-329 (2004).
Cho et al., A family with spinocerebellar ataxia type 5 found to have a novel missense mutation within a SPTBN2 spectrin repeat. Cerebellum 12, 162-164 (2013).
Clark et al., Skeletal dysplasias due to filamin A mutations result from a gain-of-function mechanism distinct from allelic neurological disorders. Hum Mol Genet 18, 4791-4800 (2009).
Clarkson et al., Beta-III spectrin mutation L253P associated with spinocerebellar ataxia type 5 interferes with binding to Arp1 and protein trafficking from the Golgi. Hum Mol Genet 19, 3634-3641 (2010).
Comtey, Fluorescence Lifetime—finally picking up momentum! Drug Discovery World Summer 2010; pp. 71-82.
Cooper et al., Microinjection of gelsolin into living cells. J Cell Biol 104, 491-501 (1987).
Cornea et al., High-throughput FRET assay yields allosteric SERCA activators. J Biomol Screen 18, 97-107 (2013).
Cornea et al., Mapping the ryanodine receptor FK506-binding protein subunit using fluorescence resonance energy transfer, J BiolChem, 2010;285:19219-19226.
Cornea et al.,FRET-based mapping of calmodulin bound to the RyR1 Ca2+ release channel, PNAS USA, 2009;106:6128-6133.
Courtemanche et al., Avoiding artefacts when counting polymerized actin in live cells with LifeAct fused to fluorescent proteins. Nat Cell Biol 18, 676-683 (2016).
Dahlin et al., PAINS in the assay: chemical mechanisms of assay interference and promiscuous enzymatic inhibition observed during a sulfhydryl-scavenging HTS. J Med Chem 58, 2091-2113 (2015).
Dahlin et al., The essential roles of chemistry in high-throughput screening triage. Future Med Chem 6, 1265-1290 (2014).
Degorce et al., HTRF: A Technology Tailored for Drug Discovery—A Review of Theoretical Aspects and Recent Applications, Curr Chem Genomics, Mar. 2009;3:22-32.
Diaz-Sylvester et al., Halothane modulation of skeletal muscle ryanodine receptors: dependence on Ca2+, Mg2+, and ATP, AmJPhysiolCellPhysiol., Apr. 1, 2008;294(4):C1103-C1112.
Doak et al., Colloid formation by drugs in simulated intestinal fluid. J Med Chem 53, 4259-4265 (2010).
Dong et al., Time-resolved FRET reveals the structural mechanism of SERCA-PLB regulation, Biochem Biophys Res Commun, Jun. 27, 2014;449(2):196-201.
Donoso et al., Stimulation of NOX2 in isolated hearts reversibly sensitizes RyR2 channels to activation by cytoplasmic calcium,JMolCellCardiol, Mar. 2014;68:38-46.
Duff et al., Mutations in the N-terminal actin-binding domain of filamin C cause a distal myopathy. Am J Hum Genet 88, 729-740 (2011).

Erickson et al., A Dynamic Pathway for Calcium-Independent Activation of CaMKII by Methionine Oxidation,Cell, May 2, 2008;133:462-474.
Erickson et al., Diabetic hyperglycaemia activates CaMKII and arrhythmias by O-linked glycosylation, Nature, Oct. 17, 2013;502:372-376.
Feher et al., Determinants of calcium loading at steady state in sarcoplasmic reticulum, Biochem Biophys Acta, 1983;727:389-402.
Ferreira et al., Complementarity between a docking and a high-throughput screen in discovering new cruzain inhibitors. J Med Chem 53, 4891-4905 (2010).
Fluorescence Innovations, NovaFluor PR Fluorescence Lifetime Plate Reader Poster, Mar. 2011.
Fluorescence Innovations, Inc., Lifetime Characterization of Cerulean:: Venus FRET Standards in Live Cells Using the NovaFluor PR Fluorescence Lifetime Plate Reader, Poster Presentation, available online, 2 pages (2010).
Fruen et al., Differential Ca2+ sensitivity of skeletal and cardiac muscle ryanodine receptors in the presence of calmodulin, Am J Physiol-Cell Phys, Sep. 1, 2000;279:C724-C733.
Fu et al., Aberrant lipid metabolism disrupts calcium homeostasis causing liver endoplasmic reticulum stress in obesity, Nature, 2011;473:528-531.
Fukuda et al., Enhanced binding of calmodulin to RyR2 corrects arrhythmogenic channel disorder in CPVT-associated myocytes, BiochemBiophysResComm, 2014;448:1-7.
Gakamsky et al., Use of fluorescence lifetime technology to provide efficient protection from false hits in screening applications, Anal. Biochem, Feb. 1, 2011;409(1):89-97.
Gao et al., beta-III spectrin is critical for development of purkinje cell dendritic tree and spine morphogenesis. J Neurosci 31, 16581-16590 (2011).
Gehrig et al., Hsp72 preserves muscle function and slows progression of sever muscular dystrophy, Nature, 2012;484:394-398.
George, Ryanodine Receptor Regulation by Intramolecular Interaction between Cytoplasmic and Transmembrane Domains Jun. 2004 Molecular Biology of the Cell, 15:2627-2638.
Girolami et al., Novel a-actinin 2 variant associated with familial hypertrophic cardiomyopathy and juvenile atrial arrhythmias: a massively parallel sequencing study. Circ Cardiovasc Genet 7, 741-750 (2014).
Goonasekera et al., Mitigation of muscular dystrophy in mice by SERCA overexpression in skeletal muscle, J Clin Invest, 2011;121:1044-1052.
Grashoff et al., Nature(London), 2010;466:263.
Greensmith et al., The effects of hydrogen peroxide on intracellular calcium handling and contractility in the rat ventricular myocyte, CellCalcium, 2010;48:341-351.
Gribbon et al., Fluorescence readouts in HTS: no gain without pain? Drug Discov Today, Nov. 15, 2003;8(22):1035-1043.
Gruber et al., Discovery of Enzyme Modulators via High-Throughput Time-Resolved FRET in Living Cells, J Biomolecular Screening, 2014;19(2):215-222.
Gruber et al., Phospholamban mutants compete with wild tye for SERCA binding in living cells, Biochem Biophys Res Commun, 2012;420:236-240.
Gruber—In-cell FRET as a Tool to Develop SERCA Activators for Drug or Gene Therapy, Poster presented at 57th Biophysical Society Annual Meeting, Feb. 2-6, 2013; Philadelphia, PA.
Guhathakurta et al., High-throughput screen, using time-resolved FRET, yields actin-binding compounds that modulate actin-myosin structure and function. J Biol Chem 293, 12288-12298 (2018).
Guo et al., Ca2+/Calmodulin-dependent protein kinase II phosphorylation of ryanodine receptor does affect calcium sparks in mouse ventricular myocytes, CircRes, Aug. 18, 2006;99(4):398-406.
Guo et al., FRET detection of calmodulin binding to the RyR2 calcium release channel, BiophysJ, 2011;101:2170-2177.
Guo et al., Kinetics of FKBP12.6 binding to ryanodine receptors in permeabilized cardiac myocytes and effects on Ca sparks, CircRes, Jun. 11, 2010;106(11):1743-1752.
Hamilton, SL., Ryanodine receptor structure: Progress and challenges, J Biol Chem, Feb. 13, 2009; 284(7):4047-4051.

(56) References Cited

OTHER PUBLICATIONS

Harris et al., Steric regulation of tandem calponin homology domain actin-binding affinity. Mol Biol Cell 30, 3112-3122 (2019).
Hartigan et al., Tracking HTS Assay Development Time: opportunity for improving drug discovery, Drug Discovery World Summer 2010; pp. 51-58.
Henderson et al., Disease-causing missense mutations in actin binding domain 1 of dystrophin induce thermodynamic instability and protein aggregation. Proc Natl Acad Sci U S A 107, 9632-9637 (2010).
Hermanson et al., Dual mechanisms of sHA 14-1 in inducing cell death through endoplasmic reticulum and mitochondria, Mol Pharmacol, 200+9;76:667-678.
Higuchi-Sanabria et al., Spatial regulation of the actin cytoskeleton by HSF-1 during aging, Molecular Biology of the Cell, vol. 29, pp. 2522-2527 (2018).
Ho et al., JPhysiol., 2011;19:4697-4708.
Holmes et al., Electron cryo-microscopy shows how strong binding of myosin to actin releases nucleotide. Nature 425, 423-427 (2003).
Hou et al., 2-Color calcium pump reveals closure of the cytoplasmic headpiece with calcium binding, PLoSONE, Jul. 11, 2012;7(7):e40369: 10 pgs.
Houser et al., Protein Kinase A-Mediated Hyperphosphorylation of the Ryanodine Receptor at Serine 2808 Does Not Alter Cardiac Contractility or Cause Heart Failure and Arrhythmias, CircRes, Apr. 11, 2014;114(8):1320-1327.
Huang et al., Two potential calmodulin-binding sequences in the ryanodine receptor contribute to a mobile, intra-subunit calmodulin-binding domain, J Cell Sci, Oct. 1, 2013;126(19):4527-4535.
Hughes et al., Principles of early drug discovery. Br J Pharmacol 162, 1239-1249 (2011).
Hurley et al., Non-pungent long chain capsaicin-analogs arvanil and olvanil display better anti-invasive activity than capsaicin in human small cell lung cancers. Cell Adh Migr 11, 80-97 (2017).
Hwang et al., Divergent Regulation of Ryanodine Receptor 2 Calcium Release Channels by Arrhythmogenic Human Calmodulin Missense Mutants, CircRes, Mar. 28, 2014;114(7):1114-1124.
Ikeda et al., Spectrin mutations cause spinocerebellar ataxia type 5. Nat Genet 38, 184-190 (2006).
Ikemoto, Regulation of calcium release by interdomain interaction within ryanodine receptors, FrontBiosci, 2002;7:d671-d683.
Ikemoto, Ryanodine Receptors: Structure, Function and Dysfunction in Clinical Diseases, New York, NY; Springer, 2004;53-65.
Inesi et al., Concerted conformational effects of Ca2+ and ATP are required for activation of sequential reactions in the Ca2+ ATPase (SERCA) catalytic cycle, Biochemistry, 2006;45:13769-13778.
Inesi et al., The Ca2+ ATPase of ccardiac sarcoplasmic reticulum: Physiological role and relevance to diseases, Biochem Biophys Res Commun, 2008;369:182-187.
Inglese et al., Nat Chem Biol, 2007;3:466.
Irwin et al., An Aggregation Advisor for Ligand Discovery. J Med Chem 58, 7076-7087 (2015).
Isenberg et al., Biophys J, 1969;9:1337.
Iwamoto et al., Structural basis of the filamin A actin-binding domain interaction with F-actin. Nat Struct Mol Biol 25, 918-927 (2018).
Jacob et al., Case of infantile onset spinocerebellar ataxia type 5. J Child Neurol 28, 1292-1295 (2012).
Jager et al., High level transient production of recombinant antibodies and antibody fusion proteins in HEK293 cells. BMC Biotechnol 13, 52 (2013).
Jameson et al., Investigations of protein—protein interactions using time-resolved fluorescence and phasors, Methods, Mar. 1, 2013;59(3):278-286.
Jessup et al., Calcium Upregulation by percutaneous Administration of Gene Therapy in Cardiac Disease (CUPID): a phase 2 trial of intracoronary gene therapy of sarcoplasmic reticulum Ca2+-ATPase in patients with advanced heart failure, Circulation, 2011;124:304-313.
Johnson et al., Cardiac sarcoplasimic reticulum function and regulation of contractility—Introduction, Ann NY Acad Sci, 1998;853:xi-xvi.
Johnson et al., Pharmacology of the cardiac sarcoplasmic reticulum calcium ATPase phospholamban interaction, Ann NY Acad Sci, 1998;853:380-392.
Jung et al., EMBOMolMed, 2012;4:180-191.
Kaplan et al., Mutations in ACTN4, encoding alpha-actinin-4, cause familial focal segmental glomerulosclerosis. Nat Genet 24, 251-256 (2000).
Kast et al., Proc Natl Acad Sci USA, 2010;107:8207.
Kimura et al., Alternative splicing of ryr1 alters the efficacy of skeletal ec coupling, CellCalcium, 2009;45:264-274.
Kleinfelder, Proc SPIE, 2003;4858:316.
Knutson et al., Chem Phys Lett, 1983;102:501.
Kobayashi et al., Dantrolene Stabilzes Domain Interactions within the Ryanodine Receptor, JBiolChem, Feb. 25, 2005; 280(8):6580-6587.
Kobayashi et al., Dantrolene, a therapeutic agent for malignant hyperthermia, markedly improves the function of failing cardiomyocytes by stabilizing interdomain interactions within the ryanodine receptor, JAmCollCardiol, 2009;53:1993-2005.
Kobayashi et al., CircJ., 2010;74:2579-2584.
Krause et al., Anaesthesia, 2004;59:364-373.
Kumar et al., Cardiotoxicity of calmidazolium chloride is attributed to calcium aggravation, oxidative and nitrosative stress, and apoptosis. Free Radic Biol Med 47, 699-709 (2009).
Lagalwar et al., Methods Mol Biol, 2013;1010:201-209.
Lakowicz et al. Principles of Fluorescence Spectroscopy, 3rd ed. Springer, New York, 2006; Table of Contents and Index.
Lanner, Ryanodine Receptors: Structure, Expression, Molecular Details, and Function in Calcium Release 2010 Cold Spring Harb Perspectives in Biology, 2:1-21.
Lebakken et al., A Fluorescence Lifetime-Based Binding Assay to Characterize Kinase Inhibitors, J Biomol Screening, 2007;12:828.
Li et al., A phosphorylation of the ryanodine does not affect calcium sparks in mouse ventricular myocytes, CircRes, 2002;90:309-316.
LI et al., Electrophoresis, 2014;35(12-13):1846.
Liu et al., Dynamic, inter-subunit interactions between the N-terminal and central mutation regions of cardiac ryanodine receptors, J Cell Sci, 2010;123:1775-1784.
Liu et al., A Novel Missense Mutation in the Spectrin Beta Nonerythrocytic 2 Gene Likely Associated with Spinocerebellar Ataxia Type 5. Chin Med J (Engl) 129, 2516-2517 (2016).
Loignon et al., Stable high volumetric production of glycosylated human recombinant IFNalpha2b in HEK293 cells. BMC Biotechnol 8, 65 (2008).
Lopata et al., Affimer proteins for F-actin: novel affinity reagents that label F-actin in live and fixed cells. Sci Rep 8, 6572 (2018).
Maclennan et al., Phospholamban: a crucial regulator of cardiac contractility, Nature Reviews, 2003;4:666-678.
Maltman et al., Chem Commun, 2010;46:6929.
Marks, Calcium cycling proteins and heart failure: Mechanisms and therapeutics, J Clin Invest, 2013;123:46-52.
Marquez et al., Curr Drug Targets, 2011;12:600-620.
Martin et al., Accepting from the best donor; analysis of long-lifetime donor fluorescent protein pairings to optimise dynamic FLIM-based FRET experiments, PLOS One, 25 pages (2018).
Maruyama et al., Mutation of aspartic acid-351, lysine-352, and lysine-515 alters the Ca2+ transport activity of the Ca2+-ATPase expressed in COS-1 cells, PNAS USA, 1988;85:3314-3318.
Marx et al., CircRes, 2001;88:1151-1158.
Maxwell et al., AmJPhysiolHeartCircPhysiol., 2012;302:H953-63.
Mcmurray et al., EurHeartJ, 1993;14:1493-1498.
Meng et al., Orientation-based FRET sensor for real-time imaging of cellular forces, J Cell Sci, 2012;125:743.
Michelangeli et al., A diversity of SERCA Ca2+ pump inhibitors, Biochem Soc Trans, 2011;39:789-797.
Mizuno et al., Infantile-onset spinocerebellar ataxia type 5 associated with a novel SPTBN2 mutation: A case report. Brain Dev 41, 630-633 (2019).
Moger et al., Screening, 2006;11:765.

(56) References Cited

OTHER PUBLICATIONS

Morine et al., Overexpression of SERCA1a in the mdx diaphragm reduces susceptibility to contraction-induced damage, Hum Gene Ther, 2010; 21:1735-1739.
Mueller et al., Direct detection of phospholamban and sarcoplasmic reticulum Ca-ATPase interaction in membranes using fluorescence resonance energy transfer, Biochemistry, 2004;43:8754-8765.
Mueller et al., SERCA structural dynamics induced by ATP and calcium, Biochemistry, 2004;43:12846-12854.
Muretta et al., High-performance time-resolved fluorescence by direct waveform recording, Rev Sci Instrum, 2010;81:103101.
Muretta et al., Direct real-time detection of the actin-activated power stroke within the myosin catalytic domain, Proc Acad Natl Sci USA, 2013;110:7211-7216.
Murphy et al., Congenital macrothrombocytopenia-linked mutations in the actin-binding domain of alpha-actinin-1 enhance F-actin association. FEBS Lett 590, 685-695 (2016).
Nesmelov et al., Proc Acad Natl Sci USA, 2011;108(5):1891.
Ni et al., Discovery of candesartan cilexetic as a novel neddylation inhibitor for suppressing tumor growth. Eur J Med Chem 185, 111848 (2020).
Nicita et al., Heterozygous missense variants of SPTBN2 are a frequent cause of congenital cerebellar ataxia. Clin Genet 96, 169-175 (2019).
Oda et al., Defective Regulation of interdomain interactions within ryanodine receptor plays a key role in the pathogenesis of heart failure, Circulation, 2005;111:3400-3410.
Oda et al., In Cardiomyocytes, Binding of Unzipping Peptide Activates Ryanodine Receptor 2 and Reciprocally Inhibits Calmodulin binding, Circulation, 2013;112:487-497.
Ohara et al., Characterization of a new beta-spectrin gene which is predominantly expressed in brain. Brain Res Mol Brain Res 57, 181-192 (1998).
Ono et al., CardiovasRes, 2010;87:609-617.
Park et al., Sarco(endo)plasmic reticulum Ca2+-ATPase 2b is a major regulator of endoplasmic reticulum stress and glucose homeostasis in obesity, Proc Natl Acad Sci USA, 2010;107:19320-19325.
Paterson et al., A fluorescence lifetime-based assay for serine and threonine kinases that is suitable for high-throughput screening, Anal Biochem, 2010;402:54.
Paul-Pletzer et al., Biochem J, 2005;387:905-909.
Perkins et al., Loss of beta-III spectrin leads to Purkinje cell dysfunction recapitulating the behavior and neuropathology of spinocerebellar ataxia type 5 in humans. J Neurosci 30, 4857-4867 (2010).
Petegem, Ryanodine Receptors: Structure and Function Sep. 2012 The Journal of Biological Chemistry, 287(38):31624-3632.
Picht et al., Sparkmaster: Automated calcium Spark Analysis with ImageJ, Am J Physiol Cell; Physiol, :2007;293:C1073-C1081.
Prestle et al., Overexpression of FK506-binding protein FKBP12.6 in cardiomyocytes reduces ryanodine receptor-mediated Ca(2+) leak from the sarcoplasmic reticulum and increases contractility, CircRes, 2001;88:188-194.
Priori et al., Inherited dysfunction of sarcoplasmic reticulum Ca2+ handling and arrhythmogenesis, CircRes, 2011;108:871-883.
Pritz et al., A Fluorescence Lifetime-Based Assay for Abelson Kinase, J Biomol Screening, 2011;16(1): 65-72.
Pritz et al., Fluorescence lifetime assays: current advances and applications in drug delivery, Expert Opinion on Drug Discovery, pp. 663-670, (2011).
Prochniewicz et al., Cooperativity in F-actin: chemical modifications of actin monomers affect the functional interactions of myosin with unmodified monomers in the same actin filament. Biophys J 65, 113-123 (1993).
Prochniewicz et al., Microsecond rotational dynamics of actin: spectroscopic detection and theoretical simulation. J Mol Biol 255, 446-457 (1996).
Prochniewicz et al., Myosin isoform determines the conformational dynamics and cooperativity of actin filaments in the strongly bound actomyosin complex. J Mol Biol 396, 501-509 (2010).

Prochniewicz et al., Structural dynamics of actin during active interaction with myosin: different effects of weakly and strongly bound myosin heads. Biochemistry 43, 10642-10652 (2004).
Qin et al., JAmHeartAssoc, 2013;2:e000184.
Raina et al., PLoSOne, 2012;7:e38594.
Rebbeck et al., High-Throughput Screens to Discover Small-Molecule Modulators of Ryanodine Receptor Calcium Release Channels. SLAS Discov 22, 176-186 (2017).
Rebbeck et al., RyR1-targeted drug discovery pipeline integrating FRET-based high-throughput screening and human myofiber dynamic Ca(2+) assays. Sci Rep 10, 1791 (2020).
Riedl et al., Lifeact: a versatile marker to visualize F-actin. Nat Methods 5, 605-607 (2008).
Robia et al., Forster Transfer Recovery Reveals That Phospholamban Exchanges Slowly From Pentamer but Rapidly From the SERCA Regulatory Complex, Circulation Research, pp. 1123-1129 (2007).
Rolland et al., Sarcopenia: Its assessment, etiology, pathogenesis, consequences and future perspectives, J Nutr Health Aging, 2008;12:433-450.
Sambrook et al., Molecular Cloning: A Laboratory Manual, Cold Spring Harbor Laboratory Press, 1989.
Samso et al., Apocalmodulin and Ca2+-calmodulin bind to neighboring locations on the ryanodine receptor, JBiolChem, Jan. 11, 2002;277(2):1349-1353.
Samso et al., Structural Characterization of the RyR1-FKBP12 interaction, J Mol Biol, 2006;356:917-927.
Sawyer et al., Disease-associated substitutions in the filamin B actin binding domain confer enhanced actin binding affinity in the absence of major structural disturbance: Insights from the crystal structures of filamin B actin binding domains. J Mol Biol 390, 1030-1047 (2009).
Shan et al., JClinInvest, 2010;120:4375-4387.
Shelley et al., Structure-activity studies on gossypol in tumor cell lines. Anticancer Drugs 11, 209-216 (2000).
Shyu et al., Visualization of ternary complexes in living cells by using a BiFC-based FRET assay. Nat Protoc 3, 1693-1702 (2008).
Simeonov et al., Fluorescence Spectroscopic Profiling of Compound Libraries, J Med Chem, 2008;51:2363.
Singh et al., The N-terminal flanking region modulates the actin binding affinity of the utrophin tandem calponin-homology domain. Biochemistry 56, 2627-2636 (2017).
Song et al., Differential integration of Ca2+-calmodulin signal in intact ventricular myocytes at low and high affinity Ca2+-calmodulin targets, JBiolChem, 2008;283:31531-31540.
Song et al., J Biol Chem, 2011;286:9120-9126.
Sorensen et al., Screening of protein kinase inhibitors identifies PKC inhibitors as inhibitors of osteoclastic acid secretion and bone resorption. BMC Musculoskelet Disord 11, 250 (2010).
Spector et al., Latrunculins—novel marine macrolides that disrupt microfilament organization and affect cell growth: I. Comparison with cytochalasin D. Cell Motil Cytoskeleton 13, 127-144 (1989).
Stange et al., JBiolChem., 2003;278:51693-51702.
Stankewich et al., Targeted deletion of betaIII spectrin impairs synaptogenesis and generates ataxic and seizure phenotypes. Proc Natl Acad Sci U S A 107, 6022-6027 (2010).
Stergiopoulous et al., BMC Health Serv Res, 2012;12:345.
Stroik et al., Targeting protein-protein interactions for therapeutic discovery via FRET-based high-throughput screening in living cells. Sci Rep 8, 12560 (2018).
Szollosi et al., CommunicationsinClinicalCytometry, 1998;34:159-179.
Tateishi et al., Defective domain-domain interactions within the ryanodine receptor as a critical cause of diastolic Ca2+ leak in failing hearts, CardiovascRes, 2009;81:536-545.
Tazzeo et al. the NADPH oxidase inhibitor diphenyleneiodonium is also a potent inhibitor of cholinesterases and the internal Ca(2+) pump, Br J Pharmacol, 2009;158:790-796.
Terentyev et al., CircRes, 2008;103:1466-1472.
Terry et al., Misakinolide A is a marine macrolide that caps but does not sever filamentous actin. J Biol Chem 272, 7841-7845 (1997).
Thomas et al., PNAS USA, 1978;75:5746-5750.

(56) References Cited

OTHER PUBLICATIONS

Thorne et al., Apparent activity in high-throughput screening: origins of compound-dependent assay interference, Curr Opin Chem Biol, 2010;14:315.

Tung et al., The amino-terminal disease hotspot of ryanodine receptors forms a cytoplasmic vestibule, Nature, 2010;468:585-588.

Uchinoumi et al., Catecholaminergic polymorphic ventricular tachycardia is caused by mutation-linked defective conformational regulation of the ryanodine receptor, CircRes, 2010;106:1413-1424.

Valley et al., Tumor Necrosis Factor-related Apoptosis-inducing Ligand (TRAIL) Induces Death Receptor 5 Networks That Are Highly Organized, J Biol Chem, 2012;287:21265-21278.

Wager et al., Defining desirable central nervous system drug space through the alignment of molecular properties, in vitro ADME, and safety attributes. ACS Chem Neurosci 1, 420-434 (2010).

Wager et al., Moving beyond rules: the development of a central nervous system multiparameter optimization (CNS MPO) approach to enable alignment of druglike properties. ACS Chem Neurosci 1, 435-449 (2010).

Wagner et al., CircRes, 2011;108:555-565.

Wang et al., Localization of an NH(2)-terminal disease-causing mutation hot spot to the clamp region in the three-dimensional structure of the cardiac ryanodine receptor, JBiolChem, 2007;282:17785-17793.

Wang et al., JBiolChem, 2011;286:12202-12212.

Wang et al., A Japanese SCA5 family with a novel three-nucleotide in-frame deletion mutation in the SPTBN2 gene: a clinical and genetic study. J Hum Genet 59, 569-573 (2014).

Wehrens et al., FKBP12.6 deficiency and defective calcium release channel (ryanodine receptor) function linked to exercise-induced sudden cardiac death, Cell, 2003;113:829-840.

Wehrens et al., Ryanodine receptor/calcium release channel PKA phosphorylation: A critical mediator of heart failure progression, PNAS USA, 2006;103:511-518.

Weins et al. Disease-associated mutant alpha-actinin-4 reveals a mechanism for regulating its F-actin-binding affinity. Proc Natl Acad Sci USA 104, 16080-5 (2007).

Weins et al., Mutational and Biological Analysis of alpha-actinin-4 in focal segmental glomerulosclerosis. J Am Soc Nephrol 16, 3694-3701 (2005).

Xiao et al., Removal of FKBP12.6 does not alter the conductance and activation of the cardiac ryanodine receptor or the susceptibility to stress-induced ventricular arrhythmias, J Biol Chem, 2007;282:34828-34838.

Xu et al., Defective calmodulin binding to the cardiac ryanodine plays a role in CPVT-associated channel dysfunction, BiochemBiophysResComm, 2010;394:660-666.

Yamaguchi et al., Molecular basis of calmodulin binding to cardiac muscle Ca(2+) release channel (ryanodine receptor), J Biol Chem, 2003;278:23480-23486.

Yamaguchi et al., JClinInvest, 2007;117:1344-1353.

Yamamoto et al., Peptide Probe study of the critical regulatory domain of the cardiac ryanodine receptor, BiochemBiophysResCommun, 2002;291:1102-1108.

Yamamoto et al., Postulated role of interdomain interaction within the ryanodine receptor Ca(2+) channel regulation, JBiolChem, 2000;275:11618-11625.

Yamamoto et al., Spectroscopic Monitoring of Local Conformational Changes during the Intramolecular Domain-Domain Interaction of the Ryanodine Receptor, Biochem, 2002;41(5):1492-1501.

Yan et al., Bidirectional regulation of Ca21 sparks by mitochondria-derived reactive oxygen species in cardiac myocytes, CardiovasRes, 2008;77:432-441.

Yang et al., In situ measurement of RyR2-calmodulin binding in permeablized cardiomyocytes, Biophys J, 2011;100:413a-414a.

Yang et al., CircRes, 2014;114:295-306.

Yano et al., Altered stoichiometry of FKBP12.6 versus ryanodine receptor as a cause of abnormal Ca(2+) leak through ryanodine receptor in heart failure, Circulation, 2000;2131-2136.

Yano et al., Circulation, 2005;112:3633-3643.

Yuan et al., Genetic mapping of targets mediating differential chemical phenotypes in Plasmodium falciparum, Nat Chem Biol, 2009;5:765-771.

Zadran et al., Fluorescence resonance energy transfer (FRET)-based biosensors: visualizing cellular dynamics and bioenergetics. Appl Microbiol Biotechnol 96, 895-902 (2012).

Zima et al., J Physiol., 2010;588:4743-4757.

Schaaf et al., Red-Shifted FRET Biosensors for High-Throughput Fluorescence Lifetime Screening. Biosensors (Basel) 8, 99 (2018).

\* cited by examiner

METHODS TO IDENTIFY MODULATORS OF TAU PROTEIN STRUCTURE

CROSS-REFERENCE TO RELATED APPLICATIONS

This application claims the benefit of U.S. Provisional Application Ser. No. 62/806,345, filed Feb. 15, 2019, which is incorporated by reference herein in its entirety.

GOVERNMENT FUNDING

This invention was made with government support under AG053951 and AG026160 awarded by National Institutes of Health. The government has certain rights in the invention.

SUMMARY OF THE APPLICATION

Tau neurofibrillary tangles (NFTs), made up of aggregates of hyperphosphorylated tau proteins, were believed to be the main histopathological hallmark of tauopathies including the Alzheimer's disease for the past few decades. However, recent studies suggest that these large insoluble aggregates of NFTs do not play the primary role as toxic entities leading to progression of disease. Tau oligomer, an intermediate form of tau prior to NFTs formation, has instead been proposed to be the primary species leading to toxicity. Tau oligomers promote toxicity in cell models and are linked to neurodegeneration and cognitive phenotypes in vivo. The present disclosure describes methods for the direct detection and targeting of the toxic tau oligomers through disrupting tau-tau interactions or altering the ensemble of conformational states of the toxic species.

A challenge in identifying tau-targeting molecules is that the exact toxic tau oligomeric species driving the neurodegenerative processes have yet to be defined. Hence, it is helpful to target the pathological species and leave the non-toxic or the neuroprotective species undisturbed. There is a lack of drug developments targeting tau that make use of biophysical approaches to directly detect ensemble changes in both oligomeric states and monomeric protein conformations of tau with high sensitivity. The FRET-based biosensors disclosed herein are capable of detecting the ensemble of conformational states of tau oligomers and monomers, and delineating the toxic and the non-toxic species with support of other cellular and biochemical assays.

The present disclosure provides methods for identifying compounds. In one embodiment, the method includes providing a genetically engineered cell that includes two tau proteins. The first tau protein includes a first heterologous domain which includes a first probe, and the second tau protein includes a second heterologous domain which includes a second probe. The cell is incubated under conditions suitable for the first and second tau proteins to form an oligomer in the cell. The method further includes contacting the cell with a test compound to form a mixture, and measuring fluorescence lifetime of the first probe, the second probe, or the combination thereof. In some embodiments, a difference between the fluorescence lifetime in the presence of the test compound and the fluorescence lifetime in the absence of the test compound is not observed. In other embodiments, the fluorescence lifetime in the presence of the test compound is reduced compared to the fluorescence lifetime in the absence of the test compound.

In one embodiment, the method includes providing a genetically engineered cell that includes a tau protein, where the tau protein includes two heterologous domains. The first heterologous domain includes a first probe, and the second heterologous domain includes a second probe. In one embodiment, the cell is incubated under conditions suitable for the tau protein to form an oligomer in the cell, and in another embodiment, the cell is incubated under conditions suitable for the tau protein to not form an oligomer, e.g., the monomer tau protein is present in the cell. The method further includes contacting the cell with a test compound to form a mixture, and measuring fluorescence lifetime of the first probe, the second probe, or the combination thereof. In some embodiments, a difference between the fluorescence lifetime in the presence of the test compound and the fluorescence lifetime in the absence of the test compound is not observed. In other embodiments, the fluorescence lifetime in the presence of the test compound is reduced compared to the fluorescence lifetime in the absence of the test compound.

In some embodiments, the cell is substantially free of fibrillar tau proteins, and optionally fibrillar tau proteins are not detectable. In some embodiments, the cell is substantially free of tau protein oligomers, and optionally tau protein oligomers are not detectable. In some embodiments, the cell is substantially free of fibrillar tau proteins and tau protein oligomers.

The method can further include determining the ability of a test compound to bind to a tau protein, and optionally identifying a test compound that binds to a tau protein or identifying a test compound that does not bind to a tau protein.

When the genetically engineered cell includes two tau proteins, in some embodiments the first heterologous domain is located at the amino-terminal end of the first tau protein and the second heterologous domain is located at the carboxy-terminal end of the second tau protein. When the genetically engineered cell includes one tau protein, in some embodiments the first heterologous domain is located at the amino-terminal end of the tau protein and the second heterologous domain is located at the carboxy-terminal end of the tau protein.

Definitions

As used herein, "tau oligomer" and "tau protein oligomer" are used interchangeably and refer to one tau protein that is folded back on itself, and also refers to two or more tau proteins. A tau oligomer can include at least 2, at least 5, at least 7, or at least 10 tau proteins A tau oligomer is typically soluble in an aqueous environment such as the cytoplasm of a cell, though it is possible that the tau oligomers may be excreted by the cells and migrate to other cells, leading to the propagation of tau pathology. A tau oligomer does not include a fibrillar form of tau. Methods for distinguishing between tau oligomers and tau fibrils are known in the art. Typically, oligomers are non-β-sheet aggregates and fibrils are β-sheet aggregates.

As used herein, the term "protein" refers broadly to a polymer of two or more amino acids joined together by peptide bonds. The term "protein" also includes molecules which contain more than one protein joined by disulfide bonds, ionic bonds, or hydrophobic interactions, or complexes of polypeptides that are joined together, covalently or noncovalently, as multimers (e.g., dimers, trimers, tetramers). Thus, the terms peptide, oligopeptide, and polypeptide are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, the terms "FRET," "fluorescence resonance energy transfer," "Förster resonance energy transfer" and "resonance energy transfer" are used interchangeably, and refer to a nonradiative energy transfer process that occurs between two chromophores.

As used herein, the term "homo-FRET" refers to a type of FRET where a single type of chromophore is used. For example, tau-GFP and tau-GFP or GFP-tau-GFP homo-FRET pairs. Homo-FRET is typically measured by fluorescence anisotropy microscopy. In fluorescence anisotropy microscopy, after excitation by polarized light, transfer of energy between like chromophores oriented differently induces a depolarization of the emitted fluorescence (Tramier et al., Methods in Cell Biology 2008, 85:395-414). Homo-FRET has greater sensitivity and the advantage of using a single spectral variant to detect interactions between identical molecules than conventional FRET techniques (Squire et al., 2004, J Struct Biol, 147:62-69). In addition, enhanced-GFP (EGFP, Li et al., 1997, J. Biol. Chem., 272:28545-28549) provides a useful chromophore for homo-FRET because its fluorescence decay is mainly mono-exponential and its fluorescence is less sensitive to light excitation (no photoconversion) than other fluorescent proteins (Tramier et al., Microscopy Research and Technique 2006, 69(11): 933-999; Valentin et al., Nature Methods 2005, 2: 801). Thus, provided that the two like chromophore probes are physically located sufficiently close (most often within 2.5 to 12 nm), the two probes function together and, upon excitation with a polarized light of an appropriate wavelength, one probe transfers a precise amount of energy (proportional to the negative sixth power of the chromophore-chromophore distance) to the other probe. This process can be specifically and quantitatively detected by observing the decrease in anisotropy. Thus, homo-FRET assays are typically used to measure (1) mutual orientation and (2) the distance and/or distance changes between the two like chromophores. When both like chromophores are attached to the same molecule, homo-FRET can be used to detect a change in the molecule's structure. When the two like chromophores are attached to different molecules, FRET can be used to detect a change in the relative positions (e.g., binding, distance apart and orientation) and structures of the two molecules.

As used herein, a "chromophore" is a molecule that includes a region that adsorbs certain wavelengths of light and interacts with such a region of another chromophore so as to be useful for FRET. Chromophores suitable for use in a FRET assay are known to the skilled person and are readily available. In one embodiment, a chromophore may be a donor (also referred to as a donor probe). A donor probe refers to a molecule that will absorb energy and then re-emit at least a portion of the energy over time. In one embodiment, a chromophore may be an acceptor (also referred to as an acceptor probe). An acceptor probe refers to a molecule that will accept energy nonradiatively from a donor, thus decreasing the donor's emission intensity and excited-state lifetime. Thus, provided that a donor probe and an acceptor probe are physically located sufficiently close (most often within 2.5 to 12 nm), the two probes function together and, upon excitation with an appropriate wavelength, the donor probe transfers a precise amount of energy (proportional to the negative sixth power of the donor-acceptor distance) to the acceptor probe. This process can be specifically and quantitatively detected by observing the decrease in donor fluorescence intensity or lifetime or, in some cases, also the energy re-emitted by the acceptor probe as fluorescence. Thus, FRET assays are typically used to measure (1) the mole fraction of donors coupled with acceptor (e.g., to determine the binding affinity between the donor-labeled and acceptor-labeled molecules) and (2) the distance and/or distance changes between donor and acceptor. When donor and acceptor are both attached to the same molecule, FRET can be used to detect a change in the molecule's structure. When donor and acceptor are attached to different molecules, FRET can be used to detect a change in the relative positions (e.g., binding, orientation) and structures of the two molecules. In one embodiment, when a fluorescent dye is attached to a protein, changes in fluorescence of the dye can be used to detect a change in the structure of the protein.

As used herein, the term "high-throughput screening" or "HTS" refers to a method drawing on different technologies and disciplines, for example, optics, chemistry, biology or image analysis, to permit rapid analysis of multiple samples at rates that permit highly parallel biological research and drug discovery. Typically, HTS includes a step of detecting FRET in a sample, with the detection taking no longer than 10, no longer than 6, or no longer than 3 minutes to read all well of a 384-well or a 1536-well plate.

As used herein, the term "wild-type" refers to the most typical form of an organism, protein, or characteristic as it occurs in nature. A "wild-type" tau protein is one having an amino acid sequence that is one of the typical forms present in an organism, such as a human.

As used herein, "genetically engineered cell" and "genetically modified cell" are used interchangeably and refer to cell into which has been introduced an exogenous polynucleotide and has been altered by human intervention. A cell is a genetically engineered cell by virtue of introduction of an exogenous polynucleotide that encodes a tau protein described herein. In one embodiment, the genetically engineered cell includes more than one exogenous polynucleotide. In one embodiment, the genetically engineered cell stably expresses a tau protein, for instance, the exogenous polynucleotide is not diluted through mitosis and/or degraded (expression of the tau protein is not transient).

As used herein, "coefficient of variation" (CV) refers to a normalized measure of dispersion of a probability distribution or frequency distribution and is defined as the ratio of the standard deviation to the mean.

As used herein, "substantially free of" a material (including, for example, a fibrillar form that includes tau proteins) refers to a cell or a composition having less than 10% of the material, less than 5% of the material, less than 4% of the material, less than 3% of the material, less than 2% of the material, or less than 1% of the material. In one embodiment, the presence of the material in a composition is undetectable.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Conditions that are "suitable" for an event to occur, such as expression of a tau protein, or "suitable" conditions are conditions that do not prevent such events from occurring. Thus, these conditions permit, enhance, facilitate, and/or are conducive to the event.

As used herein, "providing" in the context of a genetically engineered cell, a composition, an article, or a test compound means making the genetically engineered cell, composition, article, or test compound, purchasing the genetically engineered cell, composition, article, or test compound, or otherwise obtaining the genetically engineered cell, composition, article, or test compound.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The following detailed description of illustrative embodiments of the present disclosure may be best understood when read in conjunction with the following drawings.

(FIG. 2A) Schematic representation of live-cell based tau inter-molecular FRET biosensor. FRET signal is observed when tau oligomers form, which can be modulated by small-molecule inhibitors. Tau oligomer is drawn as a dimer for illustration but it can be any species more than a dimer ($\geq$2-mers). (FIG. 2B) Fluorescence microscopy images of (i) GFP channel, (ii) RFP channel and (iii) merged channel of HEK293 cells expressing tau-GFP/RFP (tau FRET biosensor). (FIG. 2C) Titration of tau-RFP (acceptor) to tau-GFP (donor) illustrates that the FRET efficiency of the biosensor follows a hyperbolic dependence on acceptor concentration. (FIG. 2D) Fluorescence lifetime measurements of the tau biosensor show efficient FRET, indicating tau self-association. (FIG. 2E) Thioflavin-S (ThS) staining of HEK293 cells expressing tau-RFP (in same total DNA concentration as used in the FRET biosensor) in the presence and absence of the positive control of tau preformed fibrils (PFF). Data are means±SD of three independent experiments. ****$P<0.0001$ by two-tailed unpaired t test.

(FIG. 3A) Expression of tau-GFP and tau-RFP expressed in HEK293 cells stained with Tau-5 antibody. (FIG. 3B) Kinetic of the FRET measurements for WT tau FRET biosensor expressed in HEK293 cells. (FIG. 3C) Fluorescent microscopy images of soluble free GFP/RFP-only (fluorophore-only control) expressed in HEK293 cells at the same donor-to-acceptor ratio as the FRET biosensor. (FIG. 3D) Fluorescence lifetime measurement of the GFP/RFP-only control indicates the basal FRET from free soluble fluorophore. (FIG. 3E) Confirmation of the functionality of the tau FRET biosensor with addition of forskolin (a known small molecule that induces tau hyperphosphorylation and self-association) and gossypetin (a known inhibitor or remodeler of fibril formation). (FIG. 3F) Quantification of in-cell thioflavin-S(ThS) staining with tau preformed fibril (PFF) used as a positive control. Data are means±SD of three independent experiments. ****$P<0.0001$ and n.s. indicates not significant by two-tailed unpaired t test.

(FIG. 4A) Representative pilot screening with NCC library containing 727 compounds. A FRET efficiency cutoff threshold was applied at a change in FRET efficiency of 5SD (black lines). Five reproducible hits decreased FRET by more than 5SD below the mean of all cells (solid circle) and MK-886 induced the largest FRET change (arrow). Surface plasmon resonance (SPR) binding curve for MK-886 to purified recombinant full-length 2N4R (FIG. 4B) wild-type (WT) and (FIG. 4C) P301L tau proteins. (FIG. 3D) FRET analysis of the dose response of MK-886 in both WT and P301L tau inter-molecular biosensors indicates $EC_{50}$ values of 1.40 and 1.84 μM respectively. Data are means±SD of three independent experiments. *$P<0.05$, $P<0.01$, *$P<0.001$ and ****$P<0.0001$ by two-tailed unpaired t test.

(FIG. 5A) Histogram plot of all compounds from the NCC screen with the tau intermolecular FRET biosensors after removal of fluorescent compounds to obtain the average FRET efficiency and the standard deviation (SD) of the screen. (FIG. 5B) Representative donor-only control screen with NCC library using cells expressing only tau-GFP which do not show FRET signal so the lifetime plot is shown. Applied threshold at a change in lifetime of 5SD is shown by the black lines. There is no reproducible hit from the donor-screen indicating that the hits observed are due to random occurrence. In addition, the hit compounds obtained from the FRET screen do not appear as hits in any of the donor-only control screens. (FIG. 5C) Histogram plot of all compounds from the NCC donor-only screen after removal of fluorescent compounds to obtain the average lifetime and the SD of the screen. SPR raw binding curves for MK-886 on (FIG. 5D) purified WT tau protein and (FIG. 5E) purified P301L tau protein. (FIG. 5F) SPR characterization of other four hit compounds show no direct binding or interaction between the compounds and the tau protein. Square: benzbromarone, circle: bumetanide, triangle: torsemide and hexagon: triclosan. Data are means±SD of three independent experiments and n.s. indicates not significant by two-tailed unpaired t test.

(FIG. 6A) Kinetic of the FRET measurements for P301L tau FRET biosensor expressed in HEK293 cells. (FIG. 6B) Characterization of the GFP-32AA-RFP (fluorophores-only FRET control) expressing cells indicates FRET. The control FRET biosensor was used to test compound interference with GFP or RFP fluorophores, eliminating non-specific compounds that cause a FRET change in the screen. (FIG. 6C) MK-886 does not cause any significant FRET change in the GFP-32AA-RFP expressing control cells. (FIG. 6D) MK-886 does not cause any significant FRET change in the soluble free GFP/RFP-only expressing control cells. Data are means±SD of three independent experiments and n.s. indicates not significant by two-tailed unpaired t test.

(FIG. 7A) Kinetic of the FRET measurements for P301L tau FRET biosensor expressed in SH-SY5Y cells. (FIG. 7B) FRET analysis of the dose response of MK-886 in the P301L tau FRET biosensors expressed in SH-SY5Y cells (for 96 hrs) indicates an $EC_{50}$ value of 1.06 µM. Data are means±SD of three independent experiments. *P<0.05 and ***P<0.001 by two-tailed unpaired t test.

(FIG. 8A) SH-SY5Y cells were transfected with vector control and P301L tau. Significant cell death is observed in cells transfected with P301L tau as compared to the vector control. (FIG. 8B) MK-886 rescued P301L tau induced cytotoxicity in SH-SY5Y cells with an $IC_{50}$ of 0.523 µM. Data are means±SD of three independent experiments. *P<0.05, P<0.01, and *P<0.001 by two-tailed unpaired t test.

(FIG. 9A) Kinetic of the P301L tau induced cell cytotoxicity in SH-SY5Y cells. (FIG. 9B) Effect of MK-886 on the total amount of tau expressed is shown by the Tau-5 antibody staining. (FIG. 9C) Effect of MK-886 on the phosphorylation state Serine 396 of P301L tau expressed in SH-SY5Y cells is shown by the Phospho-Tau S396 antibody. β-actin was used as loading control. Both controls indicate that the rescue of cell death by MK-886 is not due to an indirect mechanism. Data are means±SD of three independent experiments. *P<0.05, P<0.01 and *P<0.001 by two-tailed unpaired t test.

FIGS. 11A-5D show MK-886 binds and perturbs tau monomer conformation. (FIG. 11A) Single-molecule FRET (smFRET) measurements in the absence and presence of MK-886 with WT 2N4R tau double labeled at the proline-rich region/microtubule binding region (PRR/MTBR, left) or at the N-terminal domain (right). Tau schematic represents the labelling position for each construct. The black line is drawn from the peak of the histogram in buffer for comparison with DMSO and MK-886 samples. Representative histograms are shown.

(FIG. 13A) Effect of MK-886 on the tau fibrillization cascade characterized by thioflavin-T (ThT) assay with purified WT tau proteins. Fibrillization was induced by heparin (0.4 mg/ml) in the presence of DMSO control, MK-886 (0.5 and 5 µM) and gossypetin (50 µM, a known small-molecule inhibitor or remodeler of tau fibrils as positive control). Hexagon: tau+ no heparin, square: tau+heparin, triangle: tau+heparin+MK-886 (0.5 µM), circle: tau+heparin+MK-886 (5 µM) and diamond: tau+heparin+gossypetin (50 µM). (FIG. 13B) Effect of MK-886 on tau preformed fibrils (PFF) with gossypetin as a positive control. All samples were treated with DTT (5 mM). Data are means±SD of three independent experiments. *P<0.001, **P<0.0001 and n. s. indicates not significant by two-tailed unpaired t test.

(FIG. 14A) MK-886 and gossypetin do not interfere with ThT fluorescence after 72 hours of incubation. (FIG. 14B) MK-886 does not act as a nucleation center for fibril formation after 72 hours of incubation. Only the positive control of heparin shows a significant ThT positive signal. Data are means±SD of three independent experiments. ****P<0.0001 and n.s. indicates not significant by two-tailed unpaired t test.

DETAILED DESCRIPTION OF ILLUSTRATIVE EMBODIMENTS

Figure 1:
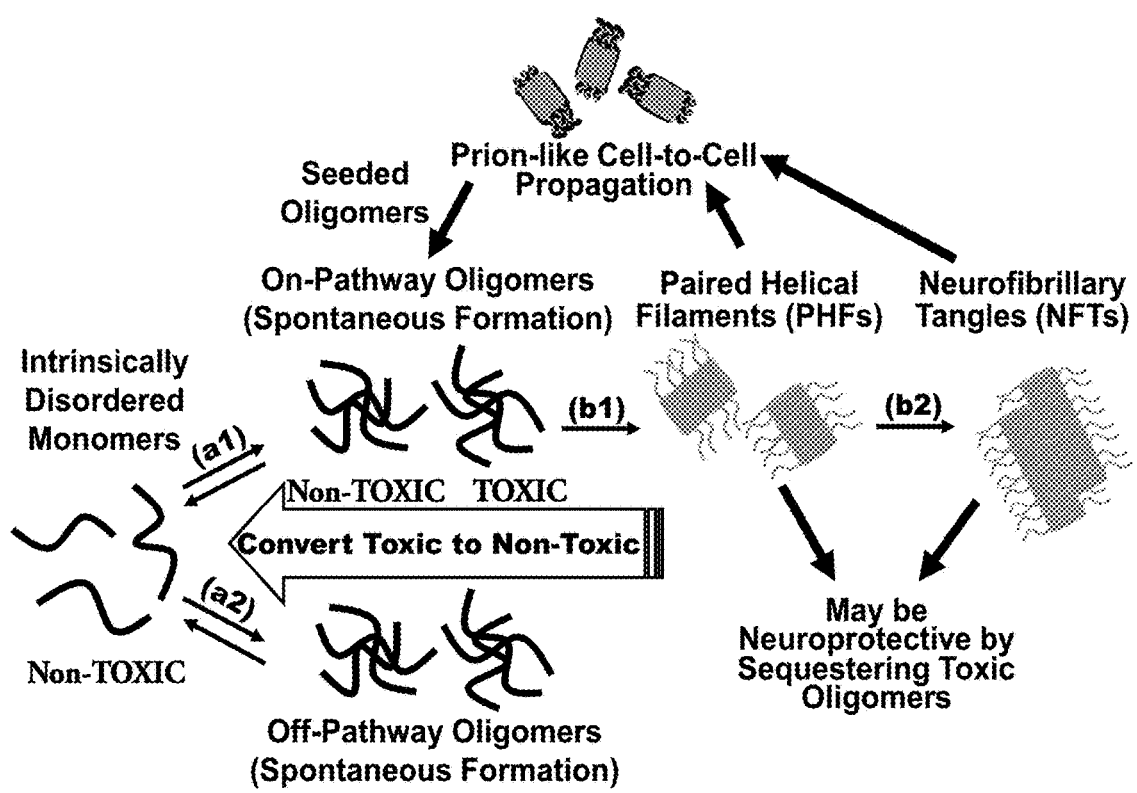
FIG. 1 shows tau fibrillogenesis cascade for tauopathies and Alzheimer's disease (AD). The intrinsically disordered tau monomer is capable of misfolding into spontaneously formed oligomers, producing toxic assemblies implicated in AD (arrows a1 and a2). While oligomers are metastable and difficult to monitor with high precision and accuracy, the large assemblies (paired helical filaments (PHFs) and neurofibrillary tangles (NFTs), arrows b1 and b2) form irreversibly with β-sheet structures. The fibrillar species can be excreted via exosomes leading to a prion-like cell-to-cell propagation of pathology and may induce seeded oligomerization. NFTs may be neuroprotective by sequestering toxic oligomers and disruption of NFTs may induce toxicity from elevated concentrations of toxic oligomers. The cellular time-resolved fluorescence resonance energy transfer (FRET) biosensors of the present disclosure target reversible spontaneous oligomerization (a1 and a2), while also monitoring seeded aggregation and downstream processes such as fibrillization (b1 and b2) with high sensitivity.

Tau protein, a member of a group of proteins referred to as Microtubule-Associated Proteins (MAPs), is an intrinsically disordered protein, i.e., it has a very low content of secondary structure. There are six isoforms of tau protein that differ according to the presence of three (3R) or four (4R) tubulin binding domains of 31 or 32 amino acids, respectively, in the C-terminal part of tau protein and one (1N), two (2N), or no inserts of 29 amino acids each in the N-terminal portion of the molecule. The six different isoforms are 2N4R (441 amino acids), 2N3R (410 amino acids), 1N4R (412 amino acids), 1N3R (381 amino acids), 0N4R (383 amino acids), and 0N3R (352 amino acids) (Kolarova et al., International Journal of Alzheimer's Disease, Volume 2012, Article ID 731526, 13 pages, doi: 10.1155/2012/731526).

Tau protein is typically bound to microtubules, but under pathological conditions can be hyperphosphorylated and detached. Unbound tau has a tendency to misfold, undergoing conformational changes that initiate the tau amyloidgenesis cascade, with an initial formation of tau oligomers that subsequently nucleate into paired helical filaments, and eventually intracellular neurofibrillary tangles. Tau oligomers exist as an ensemble of distinct assemblies (referred to as a conformational ensemble) which include both toxic and non-toxic, on- and off-pathway species along the fibrillogenesis cascade. The inventors have identified a method for monitoring the intra- and inter-molecular interactions between tau proteins that are present in an oligomer and identifying compounds that alter that interaction.

Provided herein are methods for identifying a compound that alters fluorescence resonance emission transfer (FRET) of one or more tau proteins. The alteration can be an increase or a decrease in FRET. Any isomer can be used in the methods described herein. Thus, in one embodiment, a tau protein includes the amino acid sequence of a naturally occurring tau protein. In one embodiment, a tau protein includes a naturally occurring small molecular weight species of tau or a cleaved isoform of tau. An example of a cleaved isoform of tau is delta-tau-314 (Zhao et al., 2016, Nature Medicine, 22:1268-1276).

In one embodiment, a tau protein can have one or more mutations. A mutation can be, and typically is, one of those known in the art as associated with an increase or decrease in oligomerization, an increase or decrease in fibrilization, an increase or decrease in Alzheimer's disease pathology, or a combination thereof (Wang and Mandelkow, 2016, Nature Reviews Neuroscience 17:22-35). In one embodiment, a mutation in a tau protein is a naturally occurring mutation, e.g., it is a mutation that is observed in a pathological form of tau protein. In one embodiment, a mutation is a familial Alzheimer's disease associated mutation. In one embodiment, the mutation is P301L, which can be found in isoforms 0N4R, 1N4R and 2N4R. Other examples of mutations include, but are not limited to, G272V, P301S, V337M, and R406W, which have been shown to make tau a preferable substrate for abnormal hyperphosphorylation and enhance tau oligomerization (Alonso et al., 2004, J Biol Chem, 279:34873-34881; Yoshiyama et al., 2007, Neuron, 53:337-351; Iqbal et al., 2013, Frontiers in Neurology, 4:112; and Macdonald et al., 2019, Acta Neuropathologica Communications, 7:44). The G272V, V337M and R406W mutations are present in all isoforms, and the P301S mutation is 4R isoform specific (0N4R, 1N4R and 2N4R). Other mutations include, but are not limited to, sites that are susceptible to phosphorylation by kinase such as GSK-3β, including S199, S202, T205, T231, S235, S396, and S404, which affect the oligomerization and aggregation of different tau isoforms (Combs et al., 2011, Biochemistry, 50:9446-9456). The S199, S202, T205, T231, S235, S396, and S404 mutations can be found in all isoforms.

A tau protein used in the methods described herein includes at least one heterologous domain. In one embodiment, a tau protein includes one or two heterologous domains. As used herein, a "heterologous domain" refers to a foreign sequence, e.g., an amino acid sequence (such as a fluorescent protein or a domain to which a fluorescent dye can attach such as an amino acid sequence or an unnatural amino acid) that is not normally part of a wild-type protein. The skilled person will understand that a domain to which a fluorescent dye can attach may be desirable in those embodiments where the heterologous domain is present within a tau protein, i.e., not at the N- or C-terminal end of the tau protein. In those aspects of the methods described herein using two tau proteins with each having a different chromophore, the two tau proteins can be the same or different isomers.

In one embodiment, a tau protein includes two heterologous domains, where one of the heterologous domains is a donor probe, and the second is an acceptor probe. In one embodiment, each heterologous domain is a fluorescent protein. In one embodiment, one heterologous domain is a fluorescent protein and the other is a domain to which a fluorescent dye can attach. In one embodiment, each heterologous domain is a domain to which a fluorescent dye can attach. This type of tau protein permits analysis of intramolecular FRET.

In those embodiments where the tau protein includes two heterologous domains, each heterologous domain may be present at any location in a tau protein. In one embodiment, the heterologous domains are present at the amino-terminal and the carboxy-terminal ends. In one embodiment, one or both heterologous domains are located near the proline-rich region and/or the microtubule-binding region (Elbaum-Garfinkle et al., 2012, Journal of the American Chemical Society, 134(40):16607-16613) of a tau protein. However, while the two heterologous domains can be independently located, the two heterologous domains are present at two locations that are close enough to allow FRET to occur between the two. Thus, in one embodiment, a tau protein includes a donor probe domain and an acceptor probe domain, where the distance between them in the tertiary structure of the tau protein is estimated to be no greater than 2 nanometers (nm), no greater than 4 nm, no greater than 6 nm, no greater than 8 nm, no greater than 10 nm, or no greater than 12 nm. In one embodiment, a tau protein includes a donor probe domain and an acceptor probe domain, where the distance between them in the primary structure of the tau protein is at least 3 amino acids, at least 5 amino acids, at least 10 amino acids, at least 50 amino acids, at least 100 amino acids, at least 200 amino acids, at least 300 amino acids, or at least 400 amino acids.

In one embodiment, a tau protein includes one heterologous domain. The heterologous domain may be a donor probe or an acceptor probe. The heterologous domain may be a fluorescent protein or may be a domain to which a fluorescent dye can attach. In those embodiments where a cell expresses two tau proteins, one having a heterologous domain that includes a donor probe and the other having a heterologous domain that includes an acceptor probe, the two probes are a donor-acceptor pair. This type of use of two tau proteins permits analysis of intermolecular FRET.

In those embodiments where the tau protein includes one heterologous domain, the heterologous domain may be present at any location. Thus, a heterologous domain may be at the amino-terminus of a protein, the carboxy-terminus of a protein, or at a location within the protein, such as near the proline-rich region and/or the microtubule-binding region of a tau protein.

The addition of one or two probe domains may alter the function of the tau protein in some way. Thus, in one embodiment, the function of a tau protein that includes one or two probe domains does not have any detectable change in activity or behavior compared to the wild-type tau protein that does not include the one or two probe domains. In another embodiment, the function of a tau protein that includes one or two probe domains does have a detectable change. Tau proteins useful in the methods described herein may have altered function, but preserve one or more essential characteristics that can be analyzed as disclosed herein. In some embodiments, a tau protein is a wild-type (in other words, it is a wild-type protein modified to include the two heterologous probe domains), and in others the tau protein can include one or more mutations associated with altered function of a tau protein. In one embodiment, tau activity includes binding to microtubules (Avila et al., 2004, Physiological Reviews, 84:361-384). Methods to monitor the interaction between tau and microtubule include bifluorescence complementation technique (Shin et al., 2018, International Journal of Molecular Sciences, 19(10):2978), FRET (Breuzard et al., 2013, Journal of Cell Science, 126:2810-2819), biochemical assays (Xia et al., 2019, Journal of Biological Chemistry, 294(48):18488-18503) as well as nuclear magnetic resonance spectroscopy and mass spectrometry (Kadavath et al., 2015, Proceedings of the National Academy of Sciences, 112(24):7501-7506).

Methods for engineering proteins to include one or more heterologous domains are known in the art and are routine. Typical locations for an inserted heterologous domain include the amino-terminus, the carboxy-terminus, and an internal site.

A tau protein used in the methods described herein can be produced using recombinant techniques, chemical or enzymatic synthesis, or be naturally occurring. A tau protein can be isolated or can be present in a cell.

Chromophores suitable for the methods described herein are known to the skilled person and are routinely used. Examples of suitable chromophores include, but are not limited to, fluorescent proteins, including green fluorescent protein, red fluorescent protein, yellow fluorescent protein, blue fluorescent protein, orange fluorescent protein, and maroon fluorescent protein. In some embodiments, green fluorescent protein and red fluorescent protein may be used as a donor-acceptor pair, blue fluorescent protein and yellow fluorescent protein may be used as a donor-acceptor pair, or orange fluorescent protein and maroon fluorescent protein may be used as a donor-acceptor pair. The amino acid sequences of different versions of these and other fluorescent proteins are known to the skilled person and are readily available, as are analogues of these proteins. Other chromophores include fluorescent dyes, such as fluorescent dyes that can be attached to a protein when the protein is present in a cell. Examples of such dyes are known in the art and are routinely used. Examples include dyes that react with cysteine, having reactive iodoacetamide, maleimide, or thiosulfonate groups. Other examples include the protein labeling reagent FLASH-EDT2, a dye that can react with the domain CCXXCC (SEQ ID NO:1) (Invitrogen), and SNAP-tag, a self-labeling protein tag (New England Biolabs). Other fluorescent dyes are available that react specifically with an unnatural amino acid that is incorporated into a tau protein by a modified tRNA. In one embodiment, a fluorescent dye is one that will pass through a cell membrane. Specific examples of fluorescent dyes include, but are not limited to, Alexa Fluor dyes.

Any appropriately selected two chromophores can be used as a donor-acceptor pair in the methods described herein, provided that the energy emitted by a donor (the emission spectrum) overlaps with the energy absorbed by an acceptor (the excitation spectrum), e.g., an energy transfer process (FRET) occurs between two chromophores. A donor and an acceptor that meet this overlap are referred to as a donor-acceptor pair. In one embodiment, donor-acceptor pairs are chosen such that interference from cell autofluorescence or test-compound fluorescence is minimized. Cells contain certain proteins which will absorb wavelengths of 200 to 300 nm. Accordingly, in one embodiment, donors that can be excited at longer wavelengths are typically superior to those excitable at shorter wavelengths. For instance, donors that can be excited at wavelengths of greater than 300 nm, greater than 400 nm, or greater than 500 nm, are preferred in some embodiments. In some embodiments, red-shifted donors (greater than 600 nm, greater than 700 nm, or greater than 800 nm) can be used (Schaaf et al., 2018, Biosensors, 8(4):99). Examples of wavelengths that can be used with green fluorescent protein and red fluorescent protein include, but are not limited to, an excitation wavelength of 488 nm and an emission wavelength of 517 nm. Examples of wavelengths that can be used with orange fluorescent protein and maroon fluorescent protein include, but are not limited to, an excitation wavelength of 532 nm and an emission wavelength of 568 nm. Also, probes with longer fluorescence lifetime (more than 3 nanoseconds (ns)) will be superior to probes with shorter fluorescence lifetime.

A tau protein is expressed in a cell. A polynucleotide sequence encoding the tau protein with the one or two probe domains can be readily produced by reference to the standard genetic code using known and routine methods, and the polynucleotide can be inserted into a vector. A vector is a replicating polynucleotide, such as a plasmid, phage, or cosmid, to which another polynucleotide may be attached so as to bring about the replication of the attached polynucleotide. Construction of vectors containing a polynucleotide encoding a tau protein employs standard ligation techniques known in the art. See, e.g., Sambrook et al, *Molecular Cloning: A Laboratory Manual*, Cold Spring Harbor Laboratory Press (1989) or Ausubel, R. M., ed. *Current Protocols in Molecular Biology* (1994). A vector can provide for further cloning (amplification of the polynucleotide), i.e., a cloning vector, or for expression of the protein encoded by the coding region, i.e., an expression vector. The term vector includes, but is not limited to, plasmid vectors, viral vectors, cosmid vectors, or artificial chromosome vectors.

In the exemplary methods described herein, the experimental observations indicate that FRET detection of intermolecular interaction between two tau proteins, one fused to a red fluorescent protein and one fused to a green fluorescent protein, provides measurable indications of the structural state of tau oligomers in a live cell. The experimental observations also indicate that FRET detection of intramolecular interaction within a tau protein, one end of the tau protein fused to a green fluorescent protein and the other end fused to a red fluorescent protein, provides measurable indications of the structural state of tau oligomers in a live cell.

The methods described herein use the lifetime of a chromophore instead of its intensity. A measuring instrument useful in the methods disclosed herein is a spectrometer that is compatible with FRET assays and can perform direct waveform recording to detect the entire time course of a time-resolved fluorescence decay with high quality (signal/noise>100) within 1 millisecond (ms) or less, in a microplate format that allows for the analysis of at least 100 samples per minute. An example of such an instrument is described by Petersen et al. (Rev Sci Instrum. 2014, 85(11):113101) and Schaaf et al. (SLAS Discov. 2017, 22(3): 250-261). An example of a laser suitable for the methods described herein is a passively Q-switched microchip laser (multi-wavelength series laser devices, model number FP2-473-3-10, manufactured by Concepts Research Corp., Charlotte, N.C., USA). An example of a digitizer suitable for the methods described herein is described in Pavicic (U.S. Pat. No. 6,816,102). An example of direct waveform recording suitable for the methods described herein is described in Muretta, et al. (2010, Rev Sci Instrum 81:103101).

In one embodiment, FLT is measured using a format that permits rapid evaluation of multiple samples over a short period of time, e.g., a high throughput format. In one embodiment, such a format is a plate reader (FLT-PR). FLT-PRs useful in the methods described herein are readily available (Fluorescence Innovations, Minneapolis, Minn.). The measurement of FLT by using direct waveform recording detection technology in a plate reader provides the precision to resolve small changes in FRET, and can scan the plate rapidly.

In one embodiment, a method includes identifying a compound that alters FRET of one or more tau proteins. The alteration of FRET is evidence of a perturbation of the conformational ensembles of the intrinsically unstructured two or more tau proteins that are present in an oligomer. The method includes providing a genetically engineered cell that includes one or more tau proteins and contacting the cell with a test compound to form a mixture. In one embodiment, the cell includes a tau protein having two heterologous domains; a first heterologous domain that includes a first probe, and a second heterologous domain that includes a second probe. In another embodiment, the cell includes two tau proteins, where one tau protein has a first heterologous domain that includes a first probe, and the other tau protein has a second heterologous domain that includes a second probe. The first and second probes are a donor-acceptor pair.

The genetically engineered cell can be a live cell cultured under conditions suitable for replication. In one embodiment, the genetically engineered call can be exposed to conditions suitable for the formation of tau oligomers. In one embodiment, the genetically engineered call can be exposed to conditions suitable for the analysis of tau monomers.

The method can further include use of tau proteins that have been post-translationally modified. In one embodiment, the phosphorylation of a tau protein can be altered, e.g., a tau protein can be hyperphosphorylated by, for instance, the use of forskolin. In one embodiment, a tau protein can be acylated. When a post-translationally modified tau protein is used, the method can include exposing the genetically engineered cell to conditions or an agent that results in the post-translational modification.

The method can further include determining if tau oligomers formed in the cell are cytotoxic. In one embodiment, tau oligomer-mediated cytotoxicity can be identified by comparing cells expressing one or more tau protein described herein with a control cell that does not express the tau protein(s). Optionally, the method can also include determining if a test compound that alters FRET also alters tau oligomer-mediated cytotoxicity.

The fluorescence lifetime of the donor probe, the acceptor probe, or a combination thereof is then measured. A difference between the fluorescence lifetime in the presence of the test compound and the fluorescence lifetime in the absence of the test compound indicates that the test compound alters the FRET between the donor and acceptor probes. The change in FRET can be an increase or a decrease. In one embodiment, the change in FRET can be a statistically significant change. An altered FRET can indicate changes in tau conformations, potentially shifting the tau proteins from a toxic conformation to a non-toxic conformation. This shift in tau conformations can potentially mean disruption of tau oligomers (from higher number of tau proteins to a lower number of tau proteins) or may promote non-toxic on-pathway oligomers which may initiate the tau amyloidgenesis cascade to potentially form fibrils (which have been suggested to have neuroprotective effect). A test compound identified using a method described herein is a potential therapeutic and lead compound that can be modified by medicinal chemistry and further tested in animal studies.

In those embodiments where two tau proteins are present in a cell and each tau protein includes different probes that are a donor-acceptor pair, the two tau proteins can be the same isomer or different isomers. In one embodiment, the isoform or combination of isoforms expressed in the cell are selected to increase the formation of oligomers and reduce the formation of fibrils. Tau oligomers can be formed by spontaneous self-assembly or the self-assembly may be triggered with an addition of seeds, such as a fibrillar species of tau. In one embodiment, aggregation inducers such as glycogen synthase kinase 3β, forskolin, or okadaic acid can be used to promote oligomer formation. In another embodiment, fibrillar species of tau can be used to trigger fibril formation. In another embodiment, tau aggregation inhibitors can be used to reduce the formation of tau fibrils.

An alteration in FRET may be due to the test compound directly interacting with a tau protein or by acting through an indirect pathway. Methods for determining if a compound directly interacts with a tau protein are known and include, for instance, surface plasmon resonance.

A test compound identified as changing the fluorescence lifetime of the donor probe can be further tested to determine how the compound affects the biology of tau proteins in a cell. In one embodiment, a test compound that is identified as changing the fluorescence lifetime of the donor probe can be further evaluated to determine if it reduces cytotoxicity of tau proteins. Methods for testing tau-induced cytotoxicity are known in the art and include the SH-SY5Y neuroblastoma cell model (Flach et al., Journal of Biological Chemistry 2012, 283:43223-43233; Lo Cascio et al., ACS Chemical Neuroscience 2018, 9(6):1317-1326; Zhao et al., Molecular and Cellular Neuroscience 2003, 24(2):367-379; Schulz et al., Molecular Neurobiology 2012, 46(1):205-216). Known tau mutants that are cytotoxic can be expressed in a cell and the effect of the test compound on cytotoxicity determined. Examples of tau mutations that are cytotoxic are known and include, for example, the P301L mutation (Kfoury et al., J Biol Chem., 2012, 287(23): 19440-51).

In one embodiment, the genetically modified cell is live. The genetically modified cell can be in suspension or adhered to a surface. Examples of cells useful in the methods described herein include eukaryotic cells and prokaryotic cells. Examples of eukaryotic cells include mammalian cells, such as vertebrate cells, e.g., human, murine (including mouse and rat), canine, or porcine cells. Examples of cells include, for instance, primary cells (e.g., cells that have recently been removed from a subject and are capable of limited growth in tissue culture medium), and cultured cells (e.g., cells that are capable of long-term culture in tissue culture medium). An example of a specific cell type is a neuronal cell, such as the SH-SY5Y neuroblastoma cell available from ATCC. Other examples of cells include, but are not limited to, inducible cell lines (Kfoury et al., J Biol Chem., 2012, 287(23):19440-19451), and patient-derived induced pluripotent stem cells (iPSC) neurons (Verheyen et al., PLOS ONE, 2015, 10(12):e0146127) and iPSC-derived spheroids (Lee et al., PloS One, 2016, 11(9):e0163072-e0163072; Raja et al., PloS One, 2016, 11(9):e0161969-e0161969). Other examples of eukaryotic cells include invertebrates (such as parasites, including helminths and protozoans such as *Plasmodium* spp.) and unicellular eukaryotic cells, such as yeast cells. Examples of prokaryotic cells include, for instance, *E. coli*. In some embodiments, cellular models of tau pathology can be used including, but not limited to, modification of the oligomerization trigger through the addition of tau seeds (fibrils, oligomers, or monomer), upregulation of specific kinases or chaperone proteins (e.g. GSK3β or HSP70), and treatment with environmental toxins (Gerson et al., ACS Chemical Neuroscience, 2014, 5(9):752-769). The types of cells useful for expression and analysis of a tau protein will vary depending on the tau protein, and the skilled person will be able to determine which cells can be used based on prior reports of expression of tau proteins. In some embodiments, a dysfunctional cell may be used. For instance, pathological primary neurons from mice (Zhao et al., Nature Medicine 2016, 22: 1268-1276; Weissmann et al., Traffic 2009, 10(11): 1655-1668; Timm et al., J. Biol. Chem., 2011, 286: 41711-41722), human brain-tissue (Lutz et al., Scientific Reports 2017, 7: 2668), or primary cells from transgenic animals (Hubscher et al., cAMP signaling 2015, 1294: 117-129) can be used. In one embodiment, the cell is one that can be cultured in suspension (e.g., non-adherent) and does not require contact with a surface for replication. In one embodiment, expression of the tau protein in a genetically modified cell is stable, e.g., an exogenous polynucleotide encoding the tau protein is integrated into the genomic DNA of a cell. In one embodiment, the expression of the tau protein in a genetically modified cell is transient. In one embodiment, the cells are lysed before FRET is measured. Methods for obtaining cell homogenates are known in the art.

A compound useful in the method includes, but is not limited to, an organic compound, an inorganic compound, a metal, a polypeptide, a non-ribosomal polypeptide, a polyketide, or a peptidomimetic compound. The sources for compounds that may alter activity of a protein described herein include, but are not limited to, chemical compound libraries, fermentation media of Streptomycetes, other bacteria and fungi, and cell extracts of plants and other vegetations. Small molecule libraries are available, and include AMRI library, AnalytiCon, BioFocus DPI Library, ChemX-Infinity, ChemBridge Library, ChemDiv Library, Enamine Library, The Greenpharma Natural Compound Library, Life Chemicals Library, LOPAC1280™, MicroSource Spectrum Collection, Pharmakon, The Prestwick Chemical Library®, SPECS, NIH Clinical Collection, Chiral Centers Diversity Library. In one embodiment, a library includes compounds for targeting the central nervous system (CNS) (e.g., have favorable blood-brain barrier permeability), such as CNS-MPO and CNS-Set libraries. In some embodiments, the number of compounds evaluated in an assay includes between 1 and 10,000,000 compounds, between 1 and 1,000,000 compounds, between 1 and 100,000 compounds, or between 1 and 1,000 test compounds.

Measuring the fluorescence lifetime of a donor probe, an acceptor probe, or both, of a cell that includes a single tau protein and test compound mixture or two differently labeled tau proteins and test compound mixture (e.g., a mixture present in a well) may occur over a specific time period. In one embodiment, the time period of measuring the fluorescence lifetime of a mixture is no greater than 5 seconds, no greater than 1 second, no greater than 0.5 seconds, no greater than 0.1 seconds, no greater than 0.01 seconds, no greater than 0.001 seconds, no greater than 0.0001 seconds, no greater than 0.00001 seconds, or no greater than 0.000005 seconds. This time period for measurement is distinct from the time period a donor probe fluoresces (i.e., the fluorescence lifetime of a donor probe), which is on the order of nanoseconds.

In one embodiment, the coefficient of variation (CV) obtained from a sample of cells that include a single tau protein and test compound mixture or two differently labeled tau proteins and test compound mixture (e.g., a mixture present in a well) is no greater than 1%, no greater than 0.5%, or no greater than 0.3%.

In one embodiment, a waveform obtained from a sample of cells that include a single tau protein and test compound mixture or two differently labeled tau proteins and test compound mixture (e.g., a mixture present in a well) has a signal/noise (S/N) that is at least 100, at least 200, at least 300, or at least 400.

In certain embodiments, the FRET assays disclosed herein are measured at a single emission wavelength. In certain embodiments, the FRET fluorescence lifetime properties are measured at two or more wavelengths. In certain embodiments, the methods provided herein are carried out in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (for instance, round- or flat-bottom multi-well plates). Examples of multi-well plate formats that can be used in the methods provided herein include those found on 96-well plates (12×8 array of wells), 384-well plates (24×16 array of wells), 1536-well plate (48×3 2 array of well), 3456-well plates and 9600-well plates. Other formats that may be used in the methods provided herein include, but are not limited to, single or multi-well plates comprising a plurality of domains. In certain embodiments, the plates are opaque-wall, opaque-bottom plates. In certain embodiments, the plates are black-wall, black-bottom plates. In certain embodiments, the plates have black walls and clear bottoms in order to allow bottom excitation and reading of the fluorescence signals. In certain embodiments, the plates are chosen with minimal and uniform intrinsic fluorescence intensity within the range used in the method to avoid interference with the FRET signals.

Also provided herein are kits for identifying a compound that modulates tau. A kit may include, in any combination, a tau protein labeled with a donor and an acceptor probe, a tau protein labeled with a donor probe, or a tau protein labeled with an acceptor probe. The protein(s) can be present in a genetically modified cell, or the kit can include a polynucleotide, such as a vector, encoding one or more of the tau proteins for use in transfecting a cell.

In certain embodiments, a kit may further include buffers and reagents useful for the procedure, and instructions for carrying out the assay. In certain embodiments, a kit may further include other useful agents, such as positive and negative control reagents, and the like.

Methods that can be practiced using a kit disclosed herein may be carried out in numerous formats known in the art. In certain embodiments, the methods provided herein are carried out using solid-phase assay formats. In certain embodiments, the methods provided herein are carried out in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (for instance, round- or flat-bottom multi-well plates). Examples of multi-well plate formats that can be used in the methods provided herein include those found on 96-well plates (12×8 array of wells), 384-well plates (24×16 array of wells), 1536-well plate (48×3 2 array of well), 3456-well plates and 9600-well plates. Other formats that may be used in the methods provided herein include, but are not limited to, single or multi-well plates comprising a plurality of domains. In certain embodiments, the plates are opaque-wall, opaque-bottom plates. In certain embodiments, the plates are black-wall, black-bottom plates. In certain embodiments, the plates have black walls and clear bottoms in order to allow bottom excitation and reading of the fluorescence signals. In certain embodiments, the plates are chosen with minimal and uniform intrinsic fluorescence intensity within the range used in the method to avoid interference with the FRET signals.

EXAMPLES

The present invention is illustrated by the following examples. It is to be understood that the particular examples, materials, amounts, and procedures are to be interpreted broadly in accordance with the scope and spirit of the invention as set forth herein.

Example 1

Targeting the Ensemble of Heterogeneous Tau Oligomers in Cells: A Novel Small Molecule Screening Platform for Tauopathies 1. Structured Abstract
Objective:
Understanding the heterogeneous pathology in Alzheimer's disease (AD) and related tauopathies is one of the most urgent and fundamental challenges facing the discovery of novel disease modifying therapies. Through monitoring ensembles of toxic and non-toxic tau oligomers spontaneously formed in cells, our biosensor technology can identify tool compounds that modulate tau oligomer structure and toxicity, providing much needed insight into the nature and properties of toxic tau oligomers.
Background:
Tauopathies are a group of neurodegenerative disorders characterized by pathological aggregation of the microtubule binding protein tau. Recent studies suggest that tau oligomers are the primary toxic species in tauopathies.

New/Updated Hypothesis:
We hypothesize that tau biosensors capable of monitoring tau oligomer conformation are able to identify tool compounds that modulate the structure and conformation of these tau assemblies, providing key insight into the unique structural fingerprints of toxic tau oligomers. These fingerprints will provide gravely needed biomarker profiles to improve staging of early tauopathy pathology as well as generate lead compounds for potential new therapeutics. Our time-resolved FRET (TR-FRET) biosensors provide us an exquisitely sensitive technique to monitor minute structural changes in monomer and oligomer conformation. In this proof-of-concept study, we identified a novel tool compound, MK-886, which directly binds tau, perturbs the conformation of toxic tau oligomers, and rescues tau induced cytotoxicity. Furthermore, we show that MK-886 alters the conformation of tau monomer at the proline-rich and microtubule binding regions, stabilizing an on-pathway oligomer.
Major Challenges for the Hypothesis:
Our approach monitors changes in the ensemble of assemblies that are spontaneously formed in cells.
Linkage to Other Major Theories:
Our biosensor technology is broadly applicable to other areas of tauopathy therapeutic development. These biosensors can be readily modified for different isoforms of tau, specific post-translational modifications, as well as familial AD associated mutations. We are eager to explore tau interactions with chaperone proteins, monitor cross-reactivity with other intrinsically disordered proteins, and target seeded oligomer pathology.
2. Objective
This Example emphasizes the need for targeting the heterogeneous ensemble of toxic tau oligomers in Alzheimer's disease (AD) and other tauopathies based on emerging biosensor technology. We report on two novel cellular fluorescence resonance energy transfer (FRET) biosensors that monitor tau oligomer and monomer conformations and can be used as a high-throughput screening (HTS) platform to identify novel tool compounds that modulate tau oligomer conformations, thereby attenuating their toxicity. With our biosensors and HTS platform we are poised to (1) study the conformational ensemble of tau oligomers; (2) identify novel tool compounds capable of targeting tau species, both monomer and oligomer, to disrupt oligomer formation or stabilize different tau conformations; (3) develop a biophysical fingerprint that delineates toxic and non-toxic oligomers, allowing us to better stage tau pathology, improve biomarker development, and reduce the heterogeneity present in clinical trials; and (4) provide a novel therapeutic pipeline to identify lead compounds that target spontaneously formed, early-stage oligomers, instead of late-stage neurofibrillary tangles (NFTs).
3. Background
a. Historical Evolution
Tauopathies, including AD, are a group of neurodegenerative disorders characterized by the presence of tau inclusions in affected brain regions [1]. Despite decades of rigorous and focused research, there are currently no significant disease modifying therapies for AD or related tauopathies [2]. Furthermore, there is a dearth of compounds that target tau, with only five out of the 105 small molecules currently in clinical trials being tau-focused [3,4].

Tau is an intrinsically disordered protein (IDP) that plays an important role in the regulation of microtubule stability and axonal transport [7]. Under pathological conditions, tau is hyperphosphorylated and detaches from microtubules, accumulating in the cytosol [8]. These pathological conditions have been correlated with upstream mitochondrial dysfunctions in the Krebs cycle and/or the electron transport system, oxidative stress [9,10], as well as defects in neuron morphology and axonal transport [11]. Unbound tau can misfold, initiating the tau fibrillogenesis cascade with an initial formation of tau oligomers that subsequently nucleate into paired helical filaments (PHFs), and eventually intracellular NFTs (FIG. 1) [12]. NFTs have been the primary histopathological hallmark of tauopathies, with their presence in the brain showing significant correlation with the degree of cognitive impairment [13]. However, recent studies suggest that these large insoluble NFTs are not the principle toxic species, implicating soluble oligomeric tau—intermediate tau assemblies formed prior to PHFs—in the induction of neurodegeneration [14,15]. Tau oligomers promote cytotoxicity in vitro and are linked to neurodegeneration and cognitive phenotypes in vivo [15-21]. They exist as an ensemble of distinct assemblies which include both toxic and non-toxic, on- and off-pathway species along the fibrillogenesis cascade (FIG. 1) [22-28]. Critically, no specific toxic tau oligomer species has been isolated or identified to date [29-31].

b. Rationale

Recent efforts to target toxic tau oligomers have yielded compounds with low micromolar $IC_{50}$ [32-38]. Of these small molecules, only methylene blue advanced to phase III clinical trials, albeit with unsuccessful results [39]. One commonality among these molecules is that they were initially identified using in vitro purified protein assays [32-38]. These systems do not recapitulate the cellular environment, lacking the numerous chaperone proteins that may be required to produce the ensemble of tau oligomers that populate the fibrillogenesis cascade. Additionally, purified protein assays are only capable of identifying hits that directly perturb tau and are wholly naive against indirect mechanism of action (MOA). Furthermore, many of the small molecules discovered in purified protein assays disrupted both fibrils and tau oligomers, the former having recently been suggested to be potentially inert and neuroprotective [40]. Therapeutic development for tauopathies has thus begun to shift from targeting large fibrillar aggregates to inhibiting or disrupting the formation of these toxic tau oligomers [14,31,41,42]. The complex heterogeneity of tau oligomers likely requires the cellular environment (e.g. post-translational modifications (PTM) and chaperone proteins) to produce the ensemble of toxic and non-toxic tau assemblies. Hence, a cellular biosensor approach capable of monitoring this ensemble holds promise as a novel HTS platform to discover more effective therapeutics.

Biosensors have been engineered to detect pathogenic species in patient biofluids as a biomarker for AD diagnosis [43]. We have developed a technology platform that directly monitors spontaneous tau oligomerization in cells, enabling therapeutic targeting of early-stage tau pathology. Our robust assay can be easily modified to accommodate additional tauopathy cell models and new pathological phenotypes as they continue to be elucidated. Through our approach we will develop two unique classes of tool compounds, direct tau binders and indirect tau effectors (modifying tau oligomers through orthogonal pathways). The interplay between direct and indirect MOA and corresponding changes to tau oligomer conformations and toxicity will provide much needed insight into tau pathology.

We engineered two distinct FRET biosensors to monitor tau oligomerization. These biosensors were used for HTS of the NIH Clinical Collection (NCC) library using a fluorescence lifetime plate reader (FLT-PR) [44]. Fluorescence lifetime (FLT) detection increases the precision of FRET-based screening by a factor of 30 compared with conventional fluorescence intensity detection [45], and provides exquisite sensitivity to resolve minute structural changes within protein ensembles. This sensitivity allows direct detection of conformational changes within an ensemble of oligomers (e.g. conversion from toxic to non-toxic oligomers), the dissociation of oligomers, or even changes in monomer conformations [46-48]. The FRET biosensors express full-length 2N4R wild-type (WT) tau and fluorescent protein fusion constructs in living cells, allowing us to monitor inter-molecular or intra-molecular tau interactions. Using full-length 2N4R WT tau ensures the targeting of spontaneously formed ensembles of tau oligomers, not fibrils, as the 2N4R isoform of WT tau does not fibrillize without seeding [49-52].

After first establishing that the new technology platform specifically monitors tau oligomer formation (using known tau aggregators), we identified a small molecule, MK-886, that directly binds tau and strongly attenuates FRET with an $EC_{50}$ of 1.40 µM in human embryonic kidney 293 cells (HEK293) used in our HTS (and a FRET $EC_{50}$ of 1.06 µM in SH-SY5Y cells). The compound rescues tau induced cell cytotoxicity with an $IC_{50}$ of 0.523 µM. To elucidate the MOA, we used an advanced single-molecule FRET (smFRET) technique to show that MK-886 perturbs the folding of purified, monomeric tau in the proline-rich and microtubule-binding regions. This effect is recapitulated in our cellular intra-molecular FRET biosensor and indicates an unfolding of the two termini of tau.

To further explore MK-886's MOA we employed a heparin induced thioflavin-T (ThT) aggregation assay with purified tau. MK-886 reduces the lag phase of tau fibrillization and is unable to nucleate tau fibrillization without the presence of heparin. It has been shown that overexpression of P301L tau does not induce fibril formation in SH-SY5Y cells [52], suggesting that P301L tau induced toxicity is due to toxic oligomer. Because MK-886 rescues tau induced cytotoxicity while not fully ablating tau oligomer associated FRET, we hypothesize that the rescue of P301L tau induced cytotoxicity by MK-886 is through conversion of toxic tau oligomers into non-toxic oligomers. Whether these new oligomers are on- or off-pathway species is difficult to determine in our cellular system, without the use of inducers. Thus, the rescue of P301L tau induced toxicity could be through an accelerated conversion of toxic tau oligomers into neuroprotective fibrils. Nevertheless, our new technology is well suited to identify novel compounds capable of remodeling tau oligomers and rescuing tau induced cytotoxicity.

4. New or Updated Hypothesis

Updated hypothesis: We hypothesize that the spontaneously formed ensemble of tau oligomers includes early-stage toxic tau species and by resolving conformational differences between toxic and non-toxic oligomers, we can target toxic tau assemblies, thereby rescuing tau induced pathology. Small-molecule modulation of tau conformations can be correlated with changes in the FRET signal as well as tau induced cytotoxicity. Lastly, through investigating tau oligomerization in the cellular environment, we include other protein machineries (e.g. chaperone proteins) which may play significant roles in tau pathogenesis.

a. Early Experimental or Observational Data

Figure 2A:
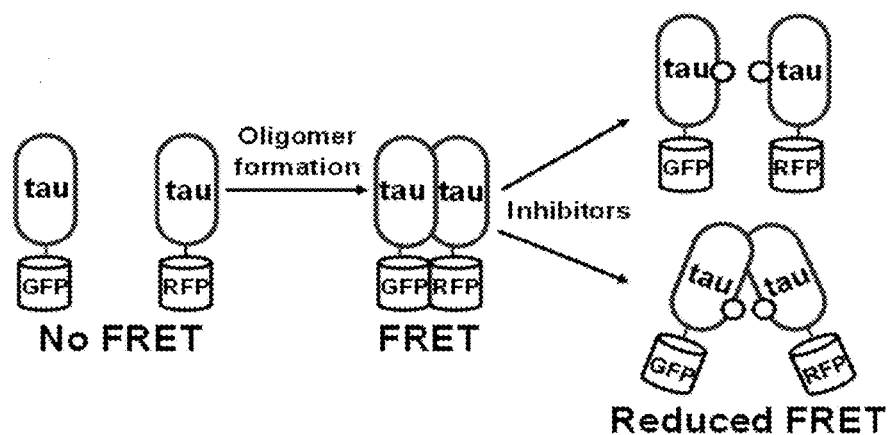
FIGS. 2A-2E show the tau inter-molecular FRET biosensor and fluorescence lifetime technology enables direct monitoring of tau oligomerization in cells.
Figure 2B:
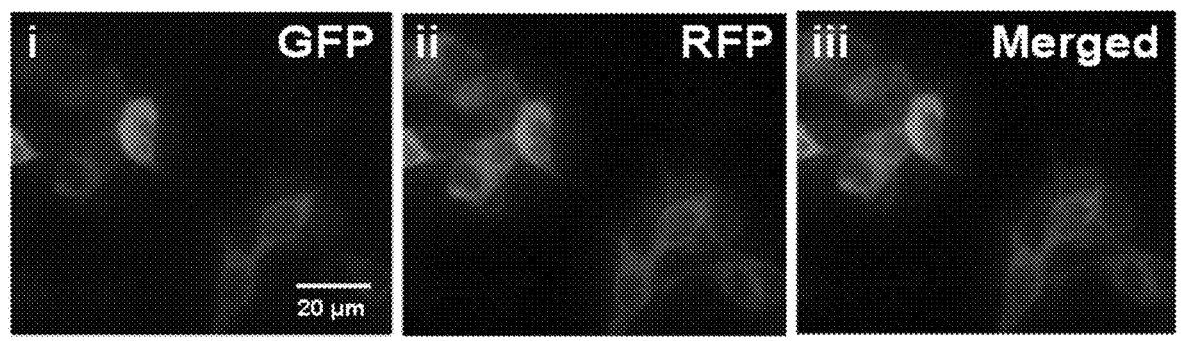
Figure 3A:
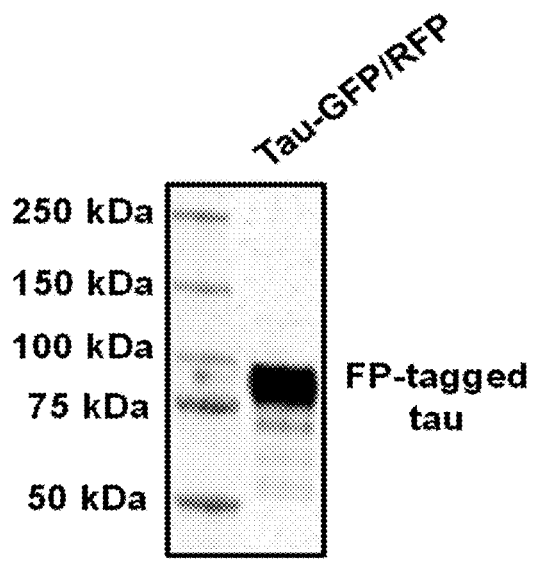
FIGS. 3A-3F show characterization of tau inter-molecular FRET biosensor and soluble free GFP/RFP expressed in HEK293 cells.

Inter-Molecular FRET Biosensor Directly Monitors Structural Changes in Tau Oligomers in Cells To develop an in-cell HTS platform that can detect small-molecule modulation of tau oligomerization and/or perturbation of tau conformational states, we engineered two cellular tau FRET biosensors. We expressed full-length 2N4R WT tau fused to green (GFP) or red (RFP) fluorescent proteins (tau-GFP/RFP or "tau FRET biosensor") in HEK293 cells (FIG. 2A). Expression and homogeneity of the FRET biosensor were determined by fluorescence microscopy and immunoblotting. Fluorescence microscopy images showed that the tau proteins were evenly distributed in the cytosol of the cells, with no discernable puncta (which would have indicated more progressive aggregation, e.g. fibril formation) or other non-uniformities (FIG. 2B). Western blot analysis of the tau biosensor cell lysates confirmed the expression of fluorophore-tagged tau (FIG. 3A).

Figure 2C:
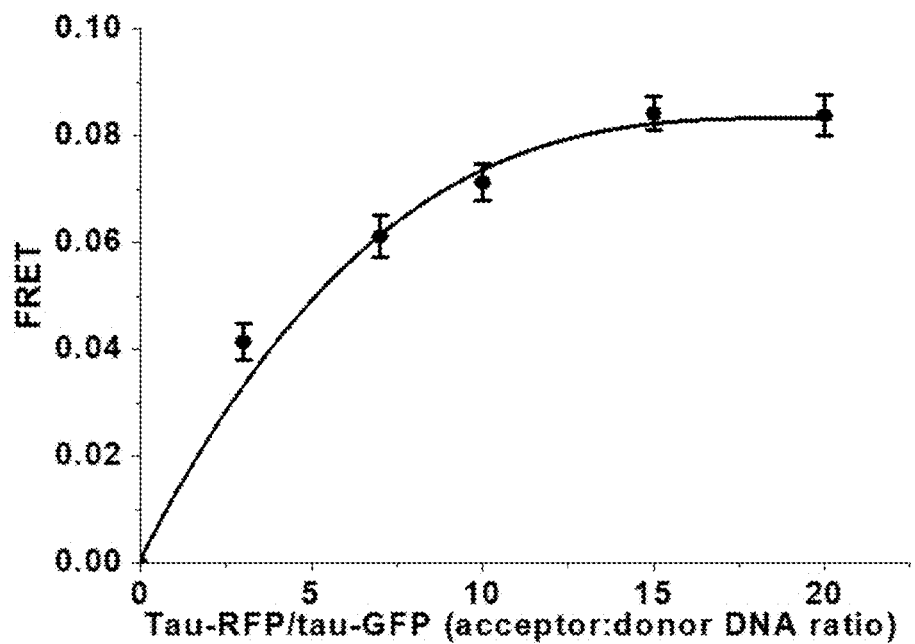
Figure 2D:
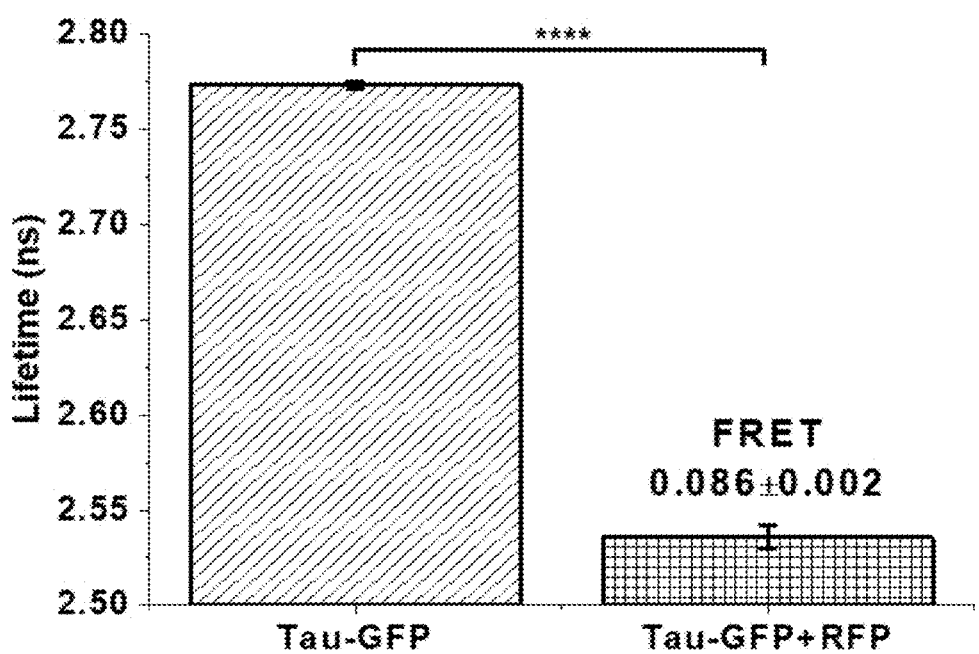
Figure 2E:
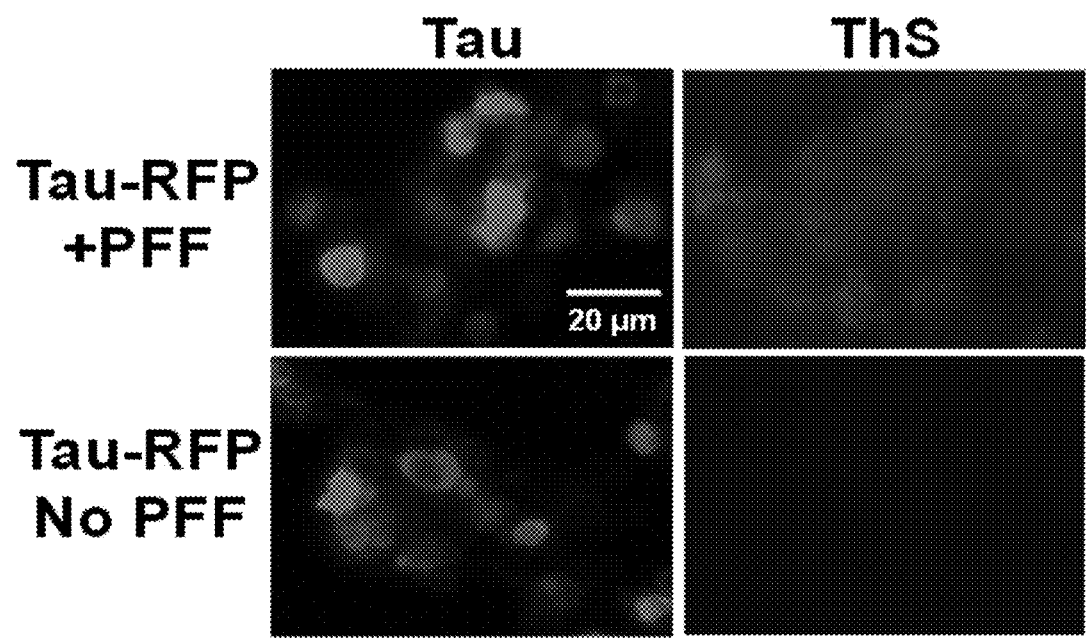
Figure 3B:
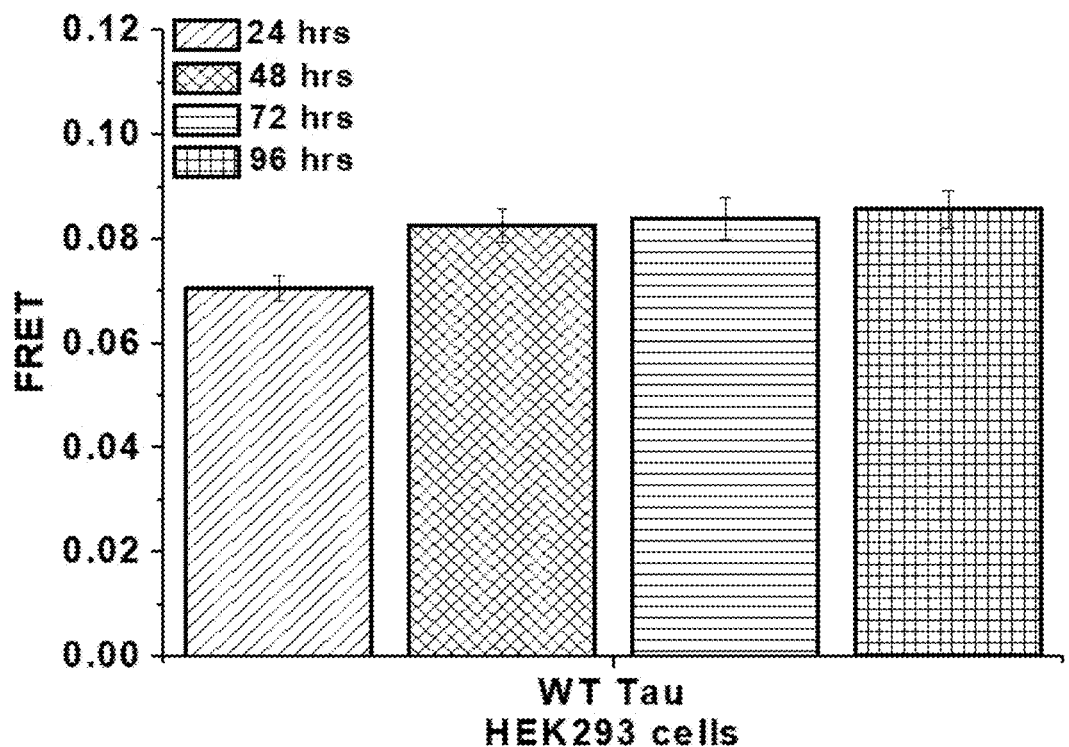
Figure 3C:
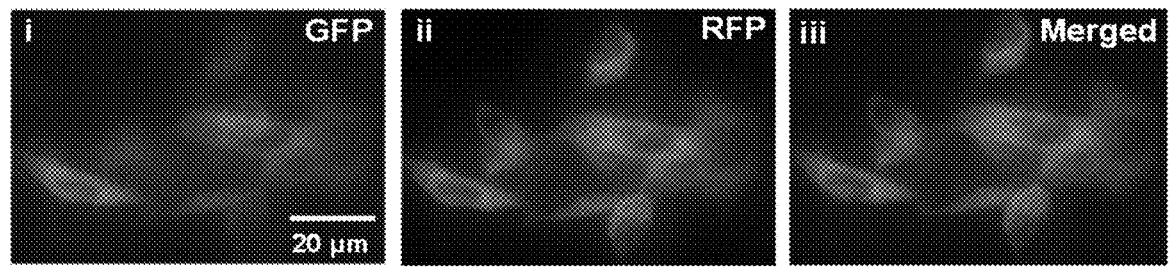
Figure 3D:
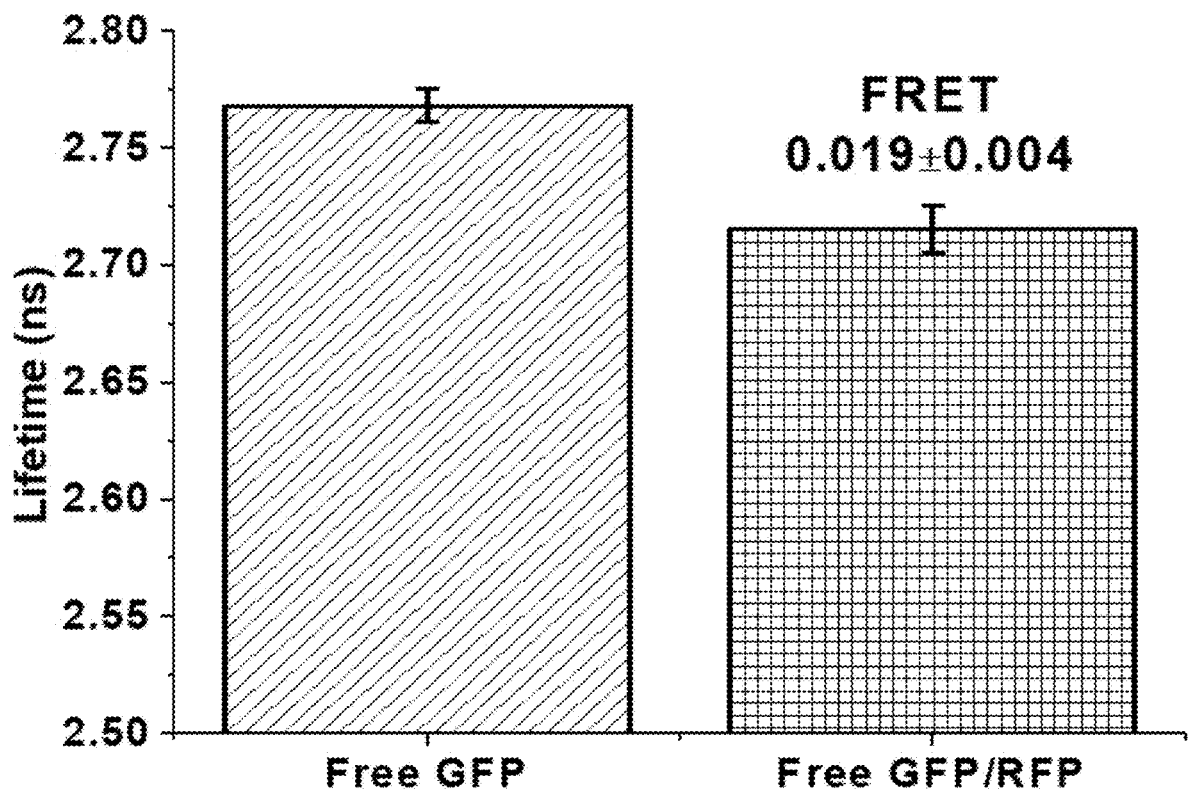
Figure 3E:
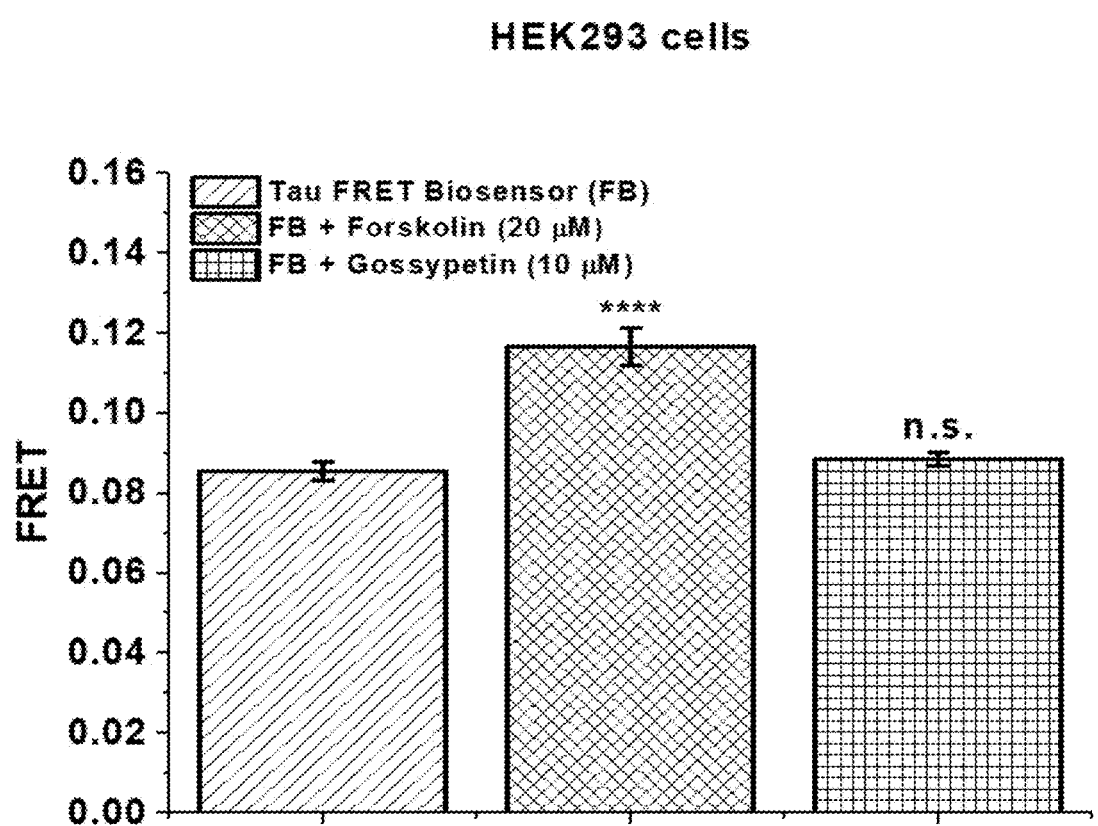
Figure 3F:
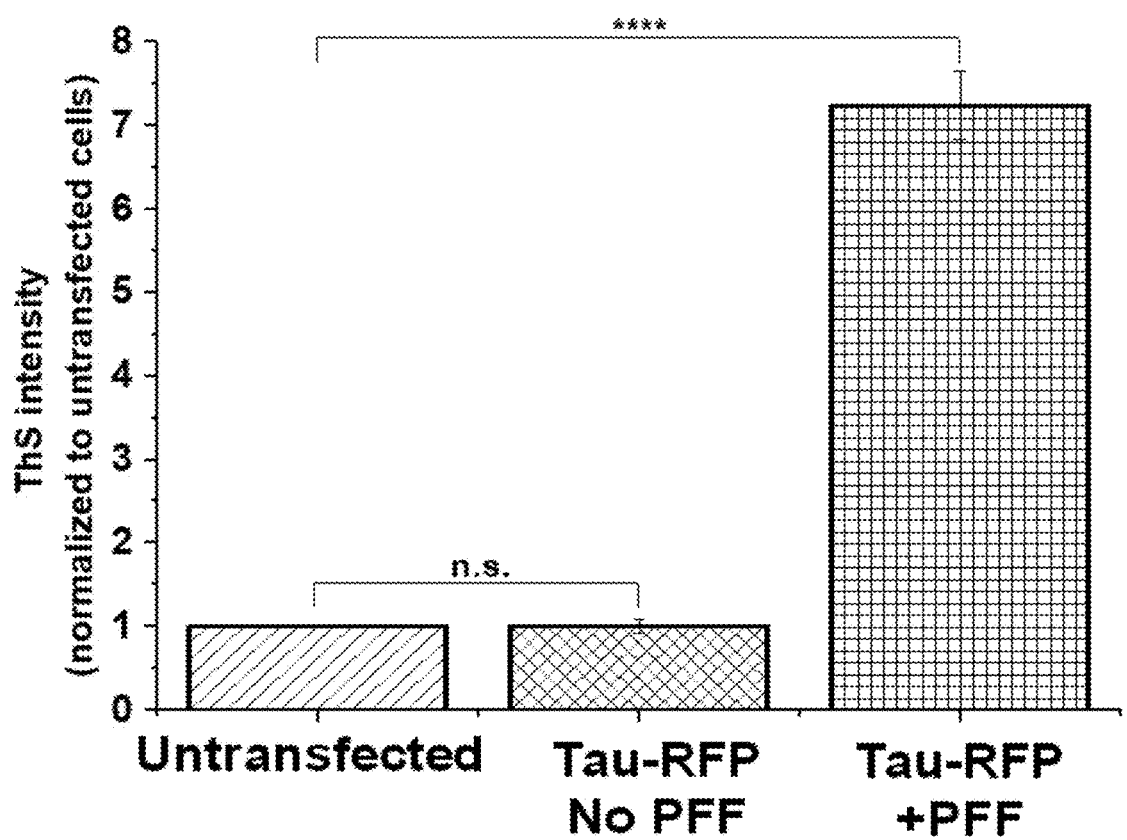

We next tested the functionality of the tau FRET biosensor by measuring FRET efficiency using the FLT-PR [44]. The value of FRET efficiency reflects the ensemble-averaged inter-molecular proximity between tau molecules, which is derived from the distance between the donor and acceptor fluorophore fused to the tau proteins. FRET between tau-GFP (donor) and tau-RFP (acceptor) in live cells showed hyperbolic dependence on acceptor concentration (FIG. 2C), with a maximum energy transfer efficiency (E) of 0.086±0.002, illustrated through a substantial decrease in the donor FLT in the presence of the acceptor (FIG. 2D), indicating the formation of tau oligomers in cells. The kinetics of formation of the tau-tau assemblies was also measured by FRET, showing that the WT tau biosensor has an optimal FRET after 48 hours of expression (FIG. 3B). We confirmed that the FRET observed from cells expressing tau biosensor arises from specific tau-tau interactions and not from non-specific interactions between the free fluorophores (FIG. 3C-D). Furthermore, we showed that the FRET biosensor is sensitive to the addition of forskolin, a small molecule known to induce tau hyperphosphorylation and self-association, but not to gossypetin, a small molecule known to inhibit or remodel of tau fibrils (FIG. 3E) [53]. To confirm that only oligomeric species of tau, but not fibrils, were present in the tau biosensor cells, we performed a thioflavin-S(ThS) assay in cells expressing tau-RFP at the same concentration of tau-GFP/RFP dual transfected cells (tau-GFP was not used as it will interfere with the ThS signal), with treatment of exogenous tau preformed fibril (PFF) as a positive control. Results from the ThS assay illustrate that only cells treated with PFF have a positive ThS signal (FIG. 2E) with a significant increase in the ThS intensity (FIG. 3F), confirming that no fibrils (e.g. β-sheet tau assemblies) are present in the biosensor cells, and more importantly that the FRET signal is the result of tau oligomerization.

Identification of Novel Small Molecules from HTS of the NCC Library that Perturb the Conformational Ensembles of Tau Oligomers Using our cellular tau FRET biosensor, we performed a HTS of the NCC library (727 bioactive compounds) to identify compounds that perturb the conformational ensembles of tau oligomers. The NCC library is a collection of small molecules that have been previously tested in clinical trials, and have known safety profiles and details on potential MOA.

Figure 4A:
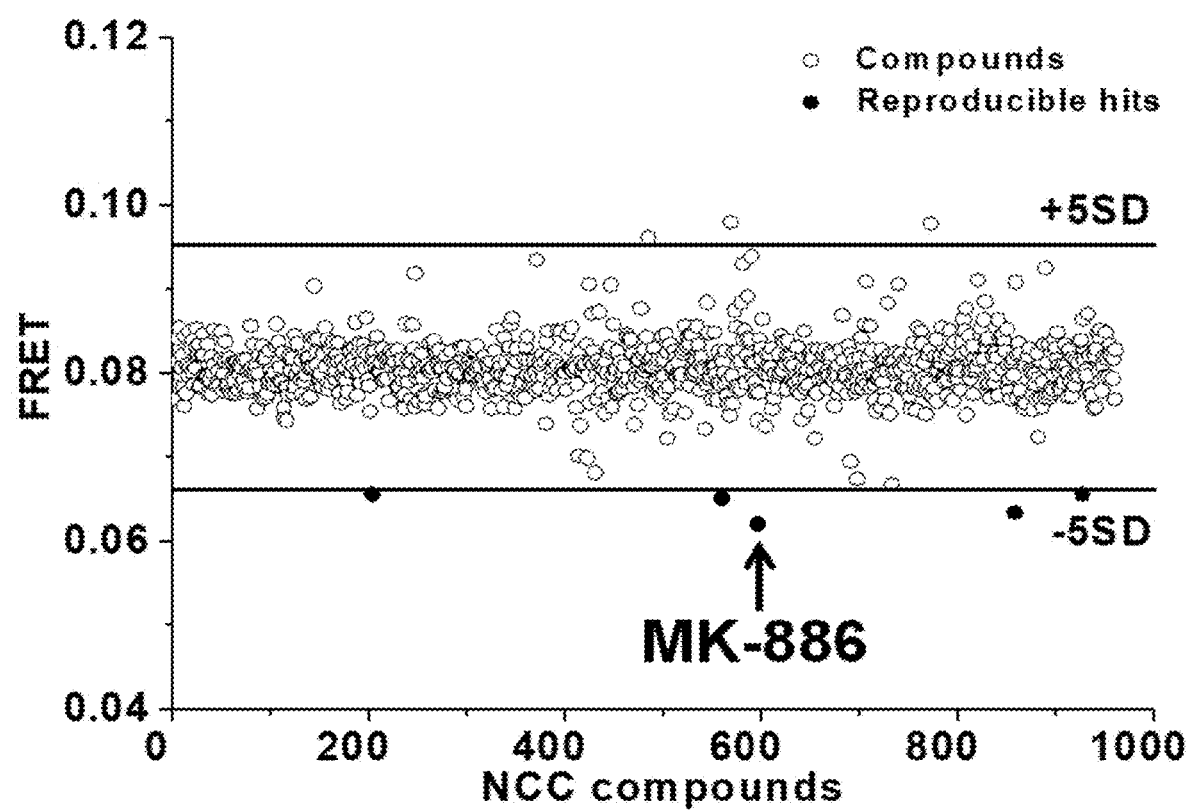
FIGS. 4A-4D show identification of MK-886 as a small molecule that directly perturbs conformational ensemble of tau oligomers.
Figure 5A:
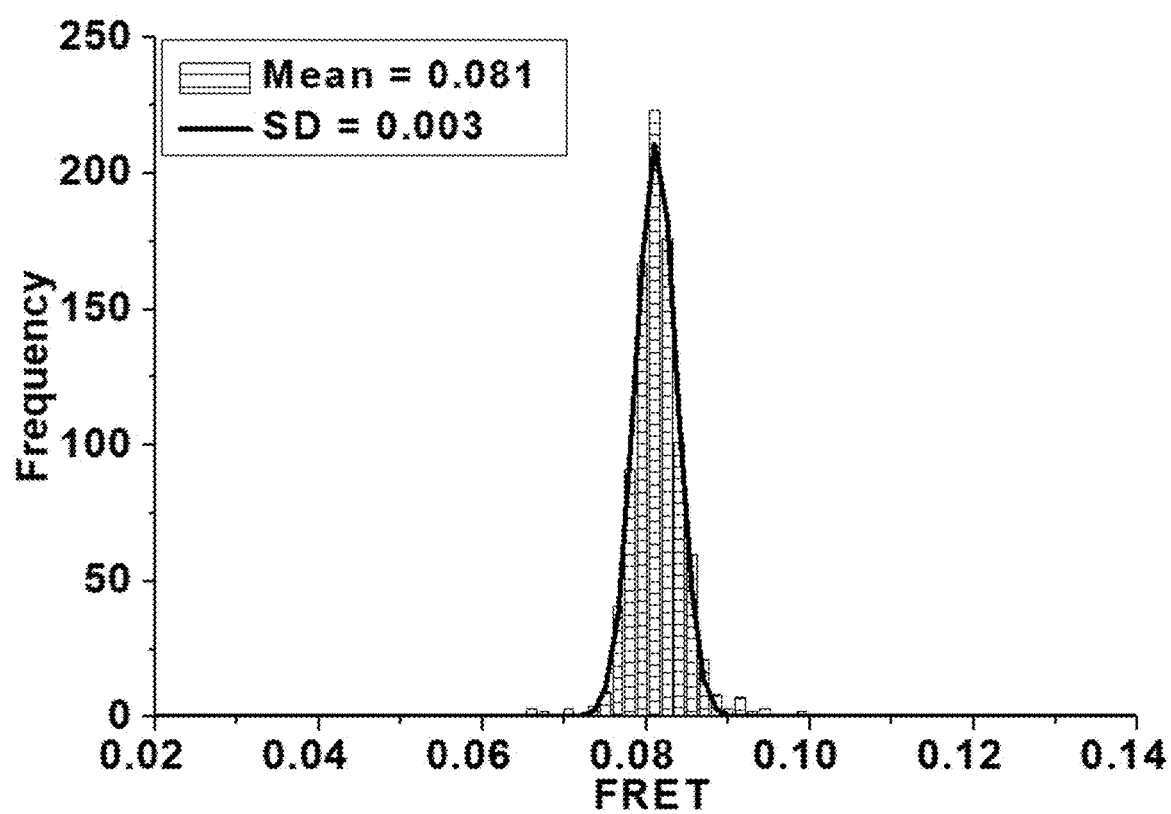
FIGS. 5A-5F show donor-only control screen and surface plasmon resonance (SPR) characterization of hit compounds in binding to purified tau protein.

After an initial quality control check of the cells expressing tau FRET biosensor on each day of screening (fluorescent waveform signal level and coefficient of variance), they were dispensed into drug plates and incubated with the compounds (10 μM) or DMSO control wells for 2 hours. FLT measurements were acquired with the FLT-PR. A single-exponential fit was used to determine the FLT from cells expressing the tau FRET biosensor ($\tau_{DA}$) or expressing a tau-GFP donor-only control ($\tau_D$) to determine FRET efficiency (Eq. 1). As FLT measurements are prone to interference from fluorescent compounds, a stringent fluorescent compound filter was used to flag 30 such compounds as potential false-positives [46,47]. FRET efficiency from all compounds that passed the fluorescent compound filter are plotted (FIG. 4A) and a histogram of the FRET distribution from these compounds was fit to a Gaussian curve to obtain a mean and standard deviation (SD) for the screen (FIG. 5A).

Figure 5B:
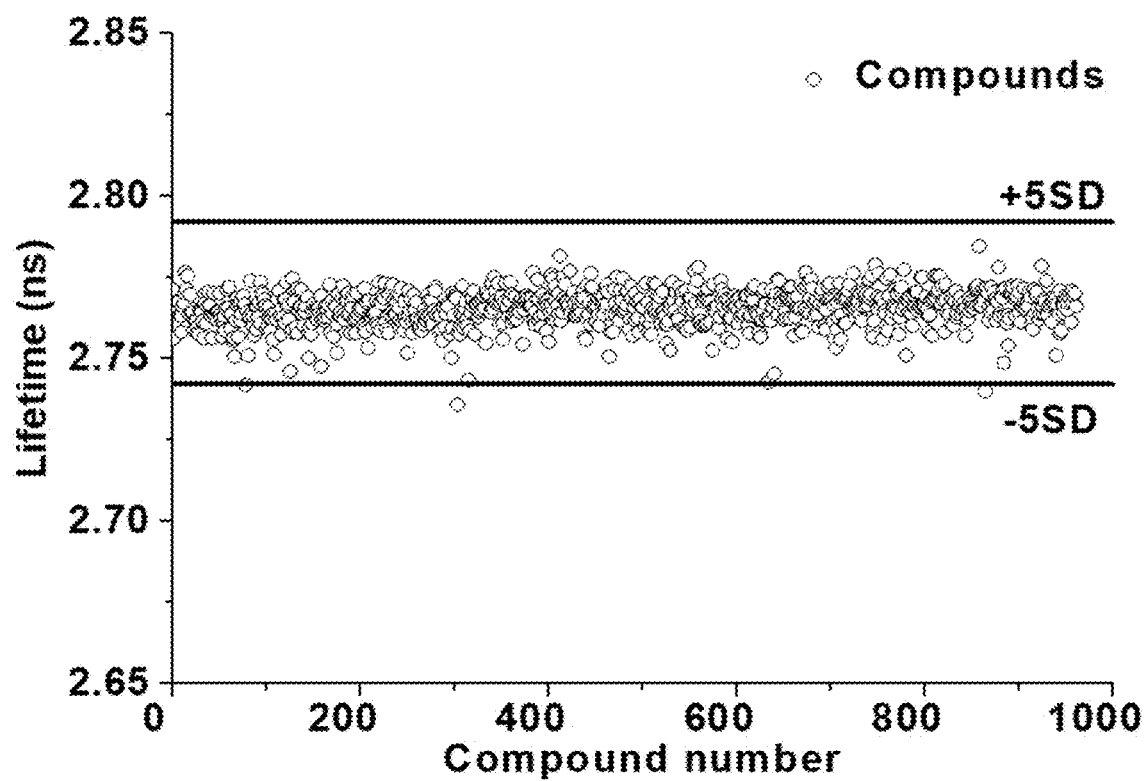
Figure 5C:
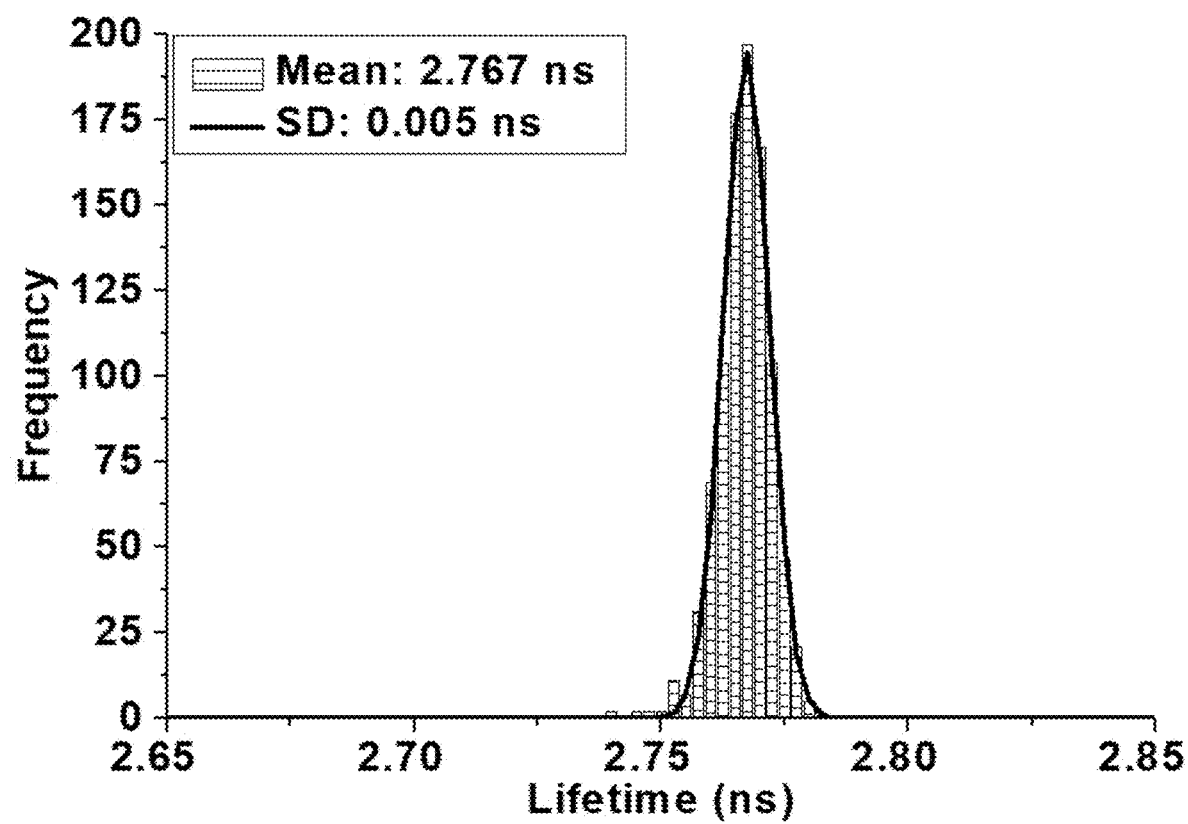

Our initial goal was to discover compounds that alter the conformational ensembles of tau oligomers with the potential of disrupting tau-tau interactions, leading us to focus our search to compounds that reduce FRET (though other compounds that increase FRET could potentially remodel toxic oligomers and be of interest in future studies). Five reproducible hits from the library were shown to decrease FRET by more than 5SD below the mean of all wells (FIG. 4A, highlighted in solid circle) while not appearing as hits in the donor-only control screen (FIG. 5B-C).

Binding of Hit Compounds to Purified Tau Proteins

Figure 4B:
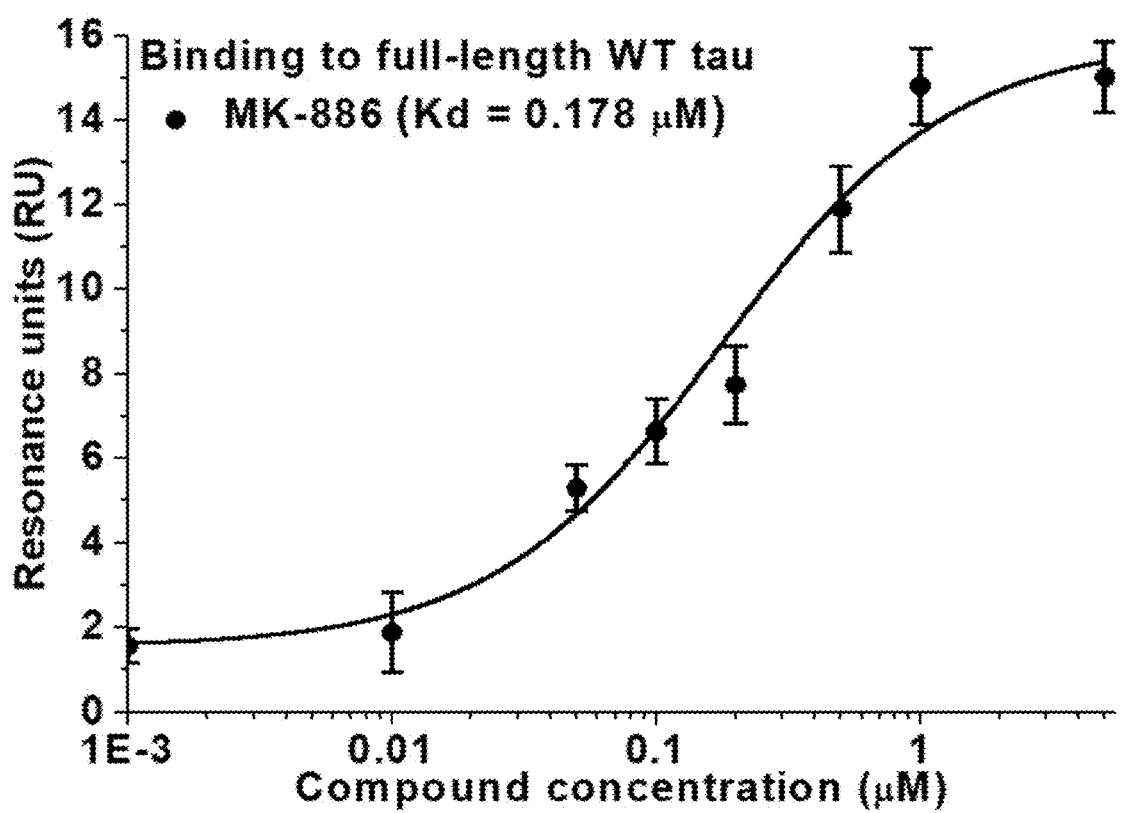
Figure 4C:
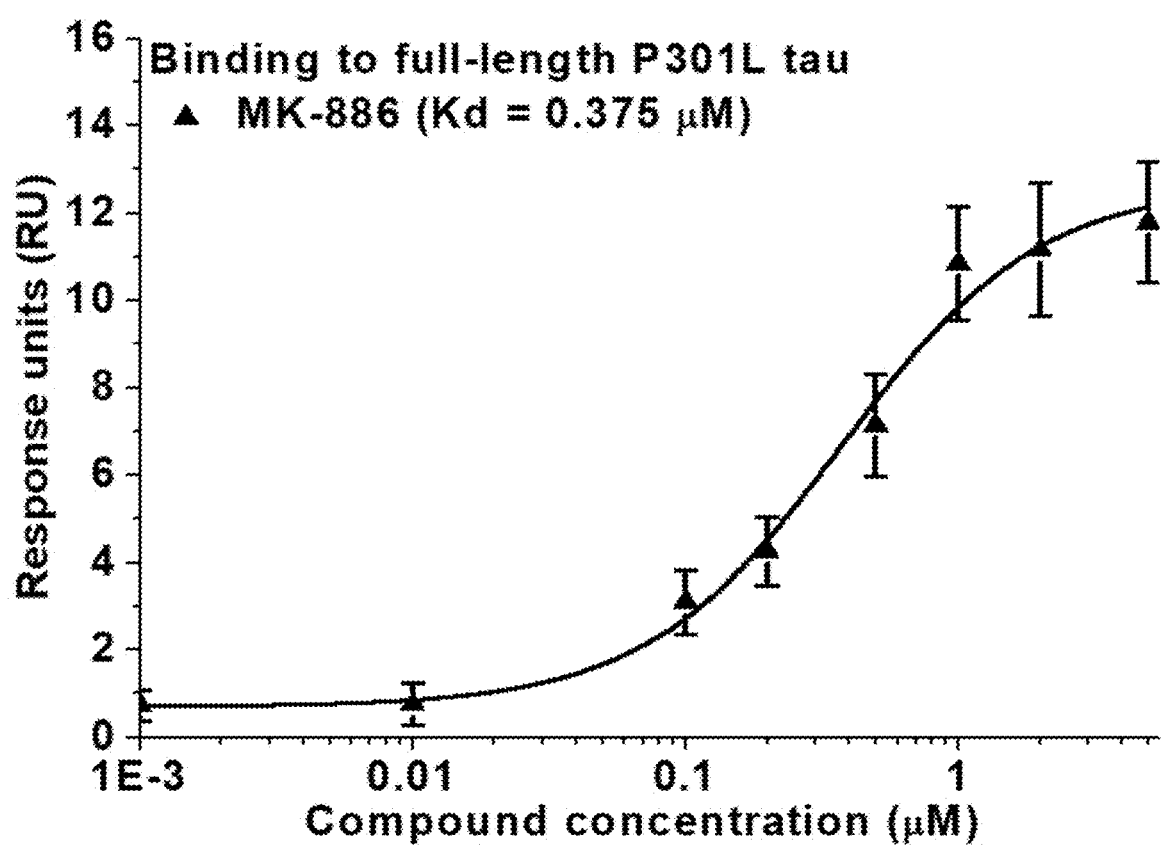
Figure 5D:
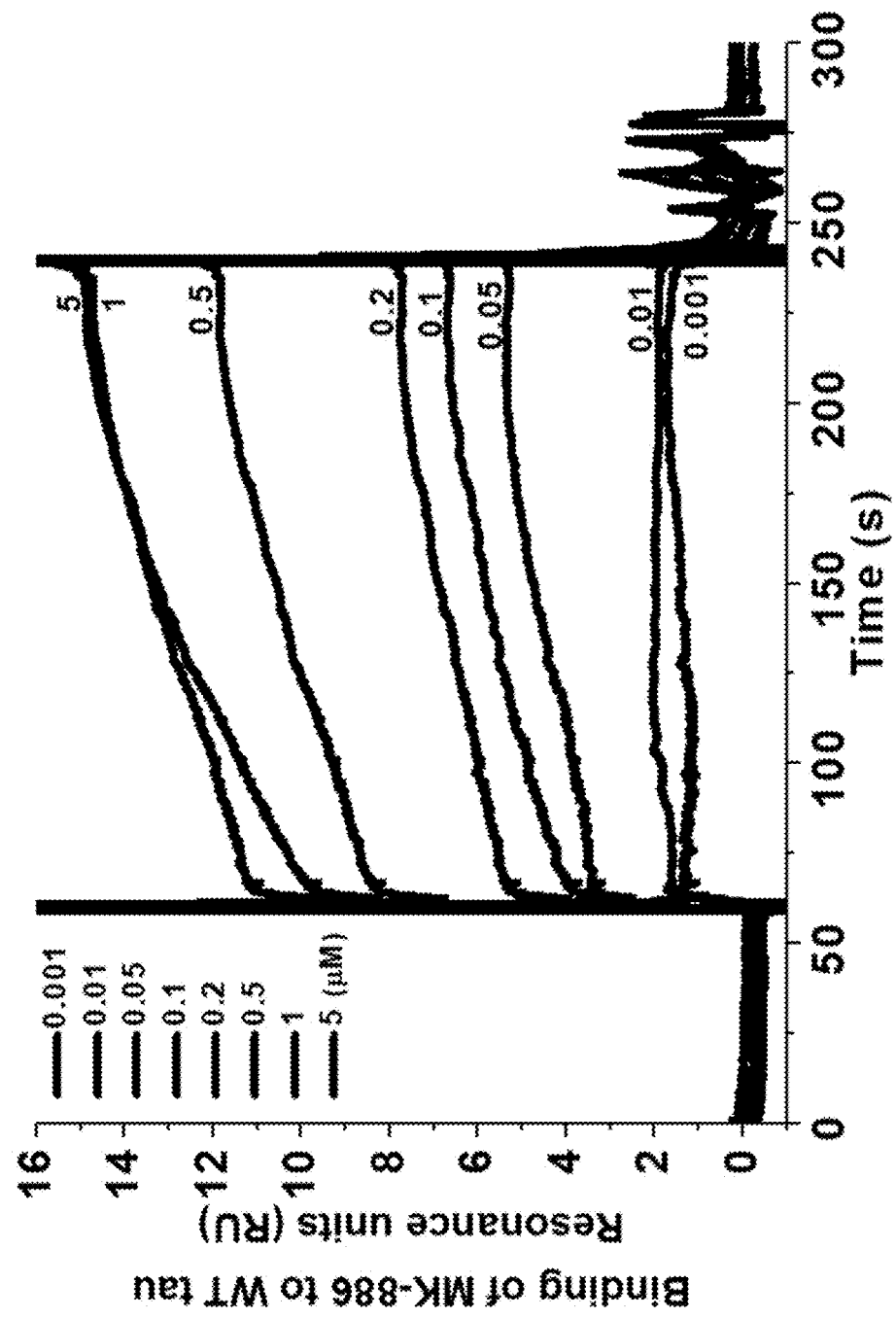
Figure 5E:
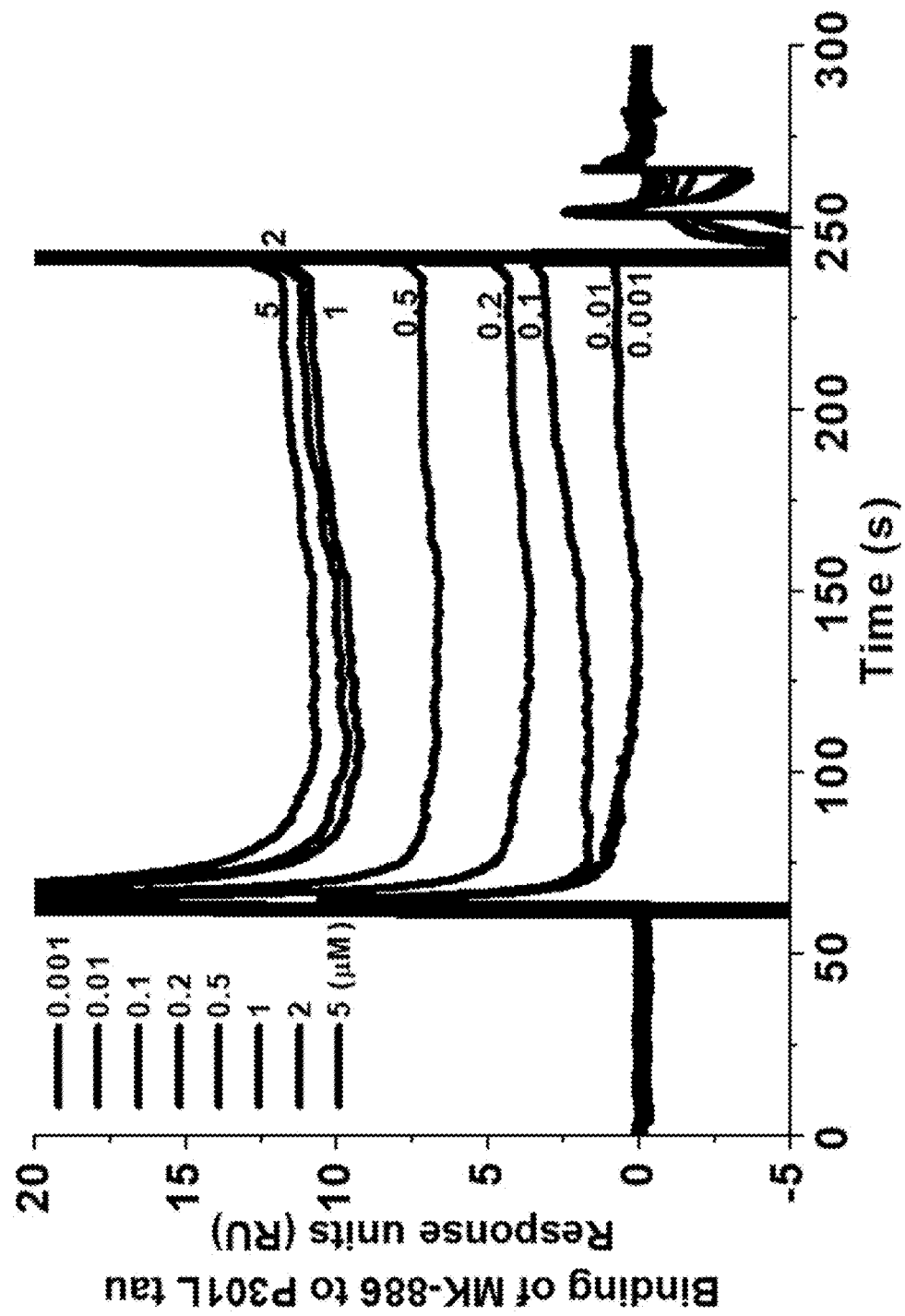
Figure 5F:
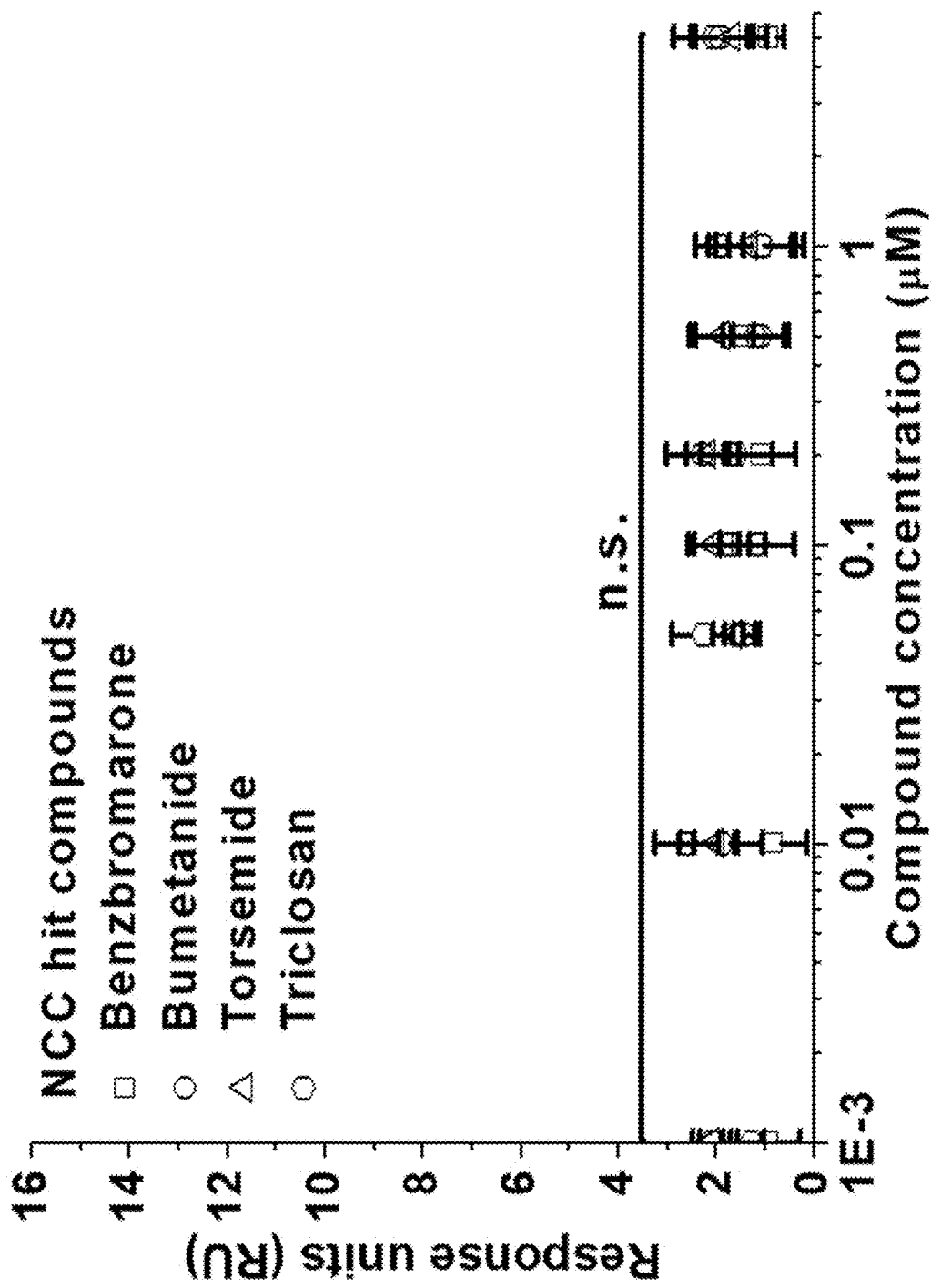

We next used surface plasmon resonance (SPR) to determine if these five hit compounds bind tau, delineating a potential direct or indirect MOA with tau. Of the five hits that reduced FRET with our tau biosensor, MK-886 was the only hit to demonstrate dose-dependent binding to purified WT tau protein with $K_d$=0.178 μM (FIG. 4B and FIG. 5D). MK-886 also showed binding to purified P301L tau protein, a more aggregation prone mutant of tau [54], with $K_d$=0.375 μM (FIG. 4C and FIG. 5E). Interestingly, MK-886 also had the strongest change in FRET (FIG. 4A, highlighted in arrow). The other four hit compounds did not show direct binding to immobilized tau protein (FIG. 5F) and therefore most likely attenuate tau FRET through an indirect MOA. All subsequent analysis in this study is focused on MK-866. The indirect MOA compounds, although outside the scope of this study, are potentially useful and are briefly discussed below.

FRET Dose-Response of MK-886 with Cellular Tau Inter-Molecular FRET Biosensors

Figure 4D:
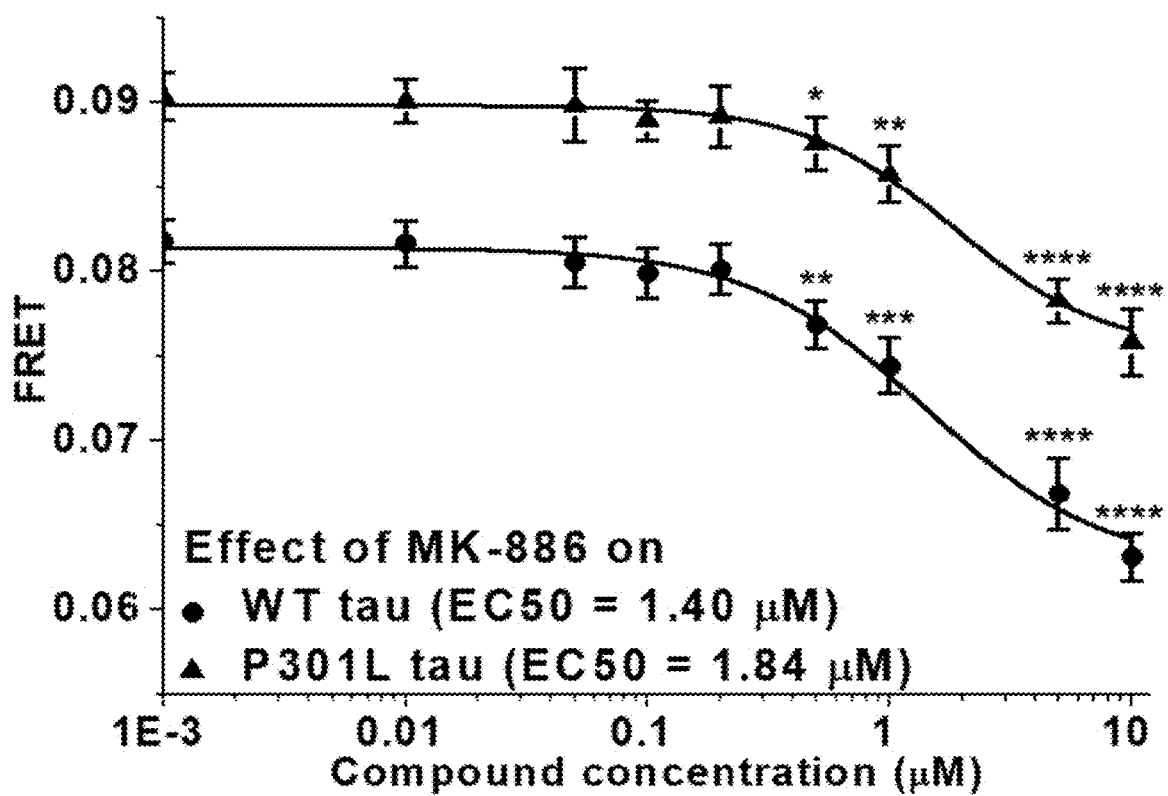
Figure 6A:
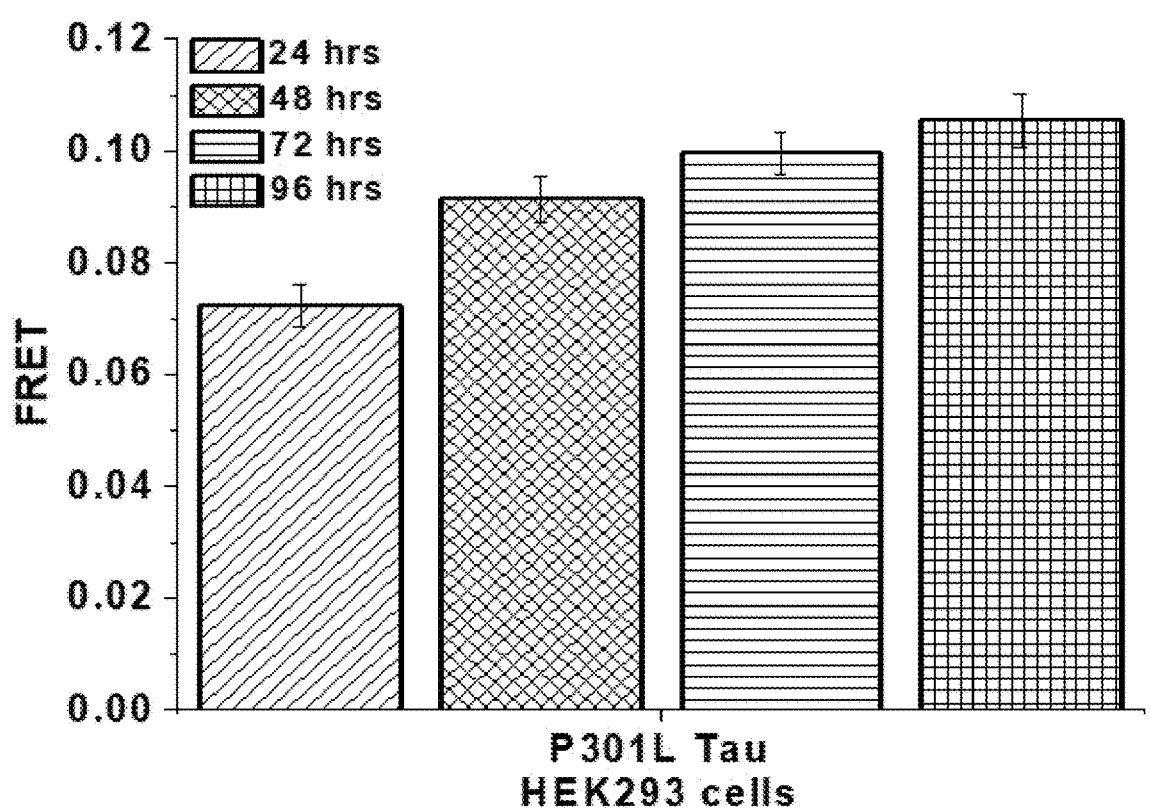
FIGS. 6A-6D show characterization of P301L tau FRET biosensor and the effect of MK-886 on control FRET biosensors.
Figure 6B:
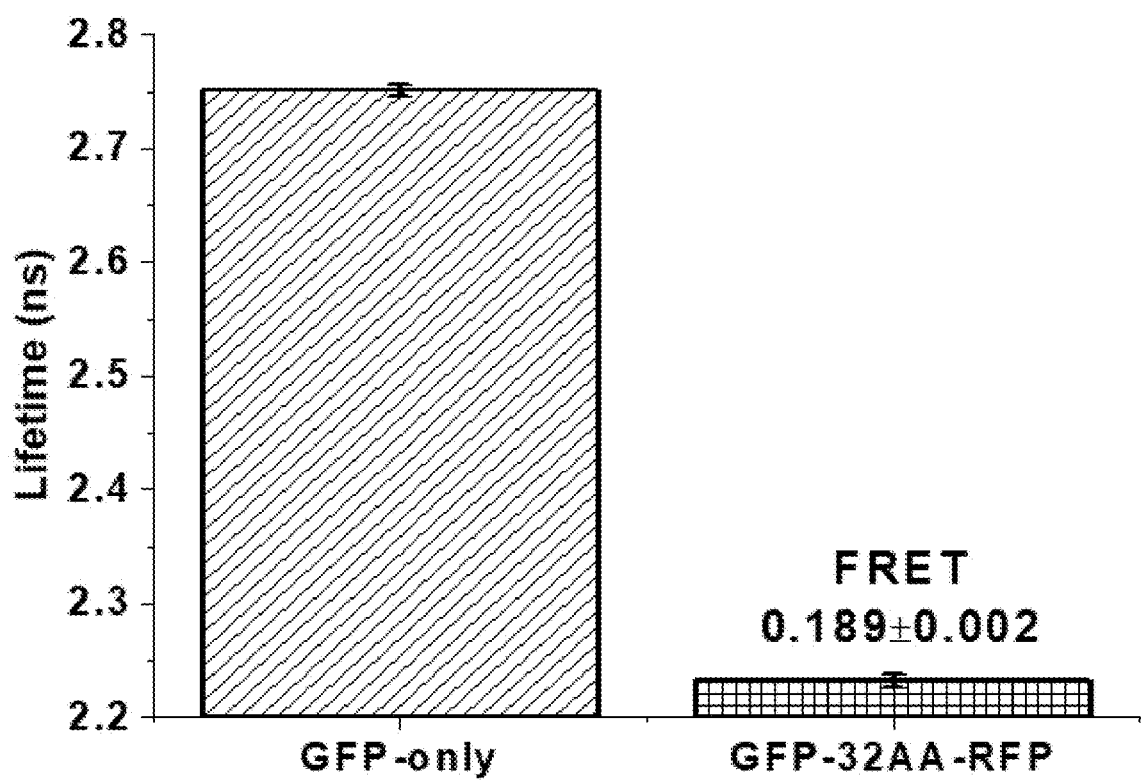
Figure 6C:
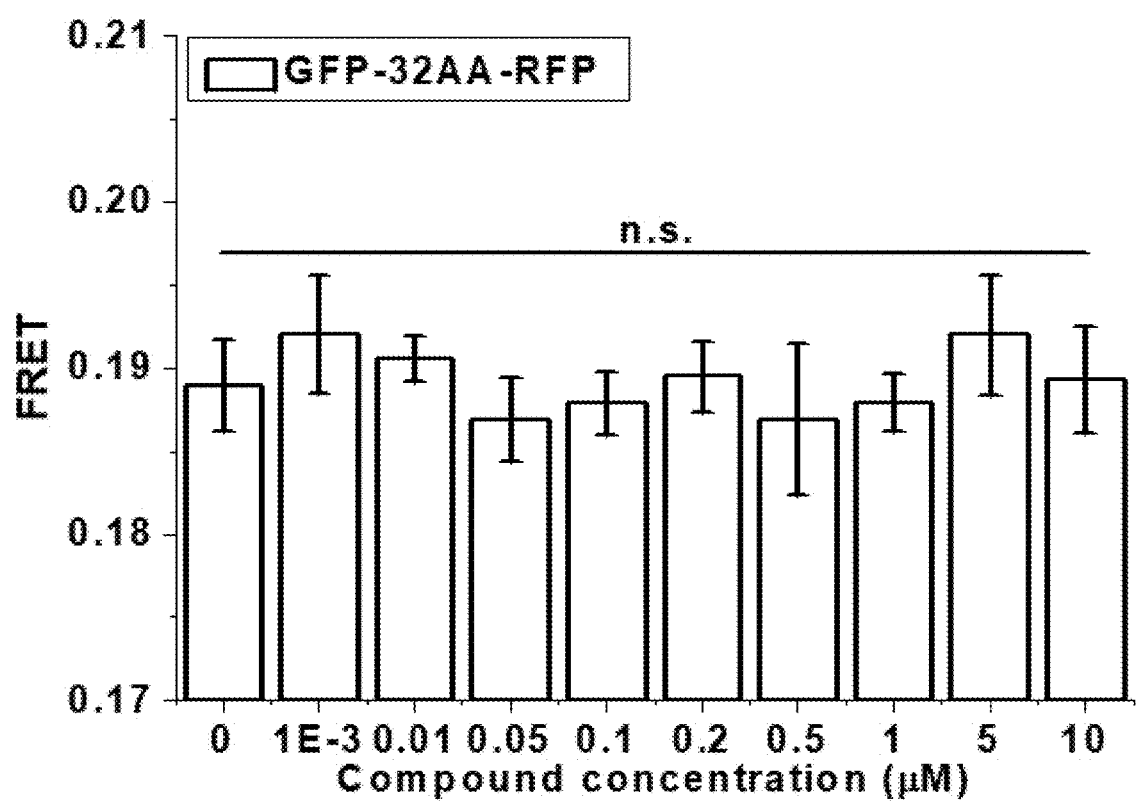
Figure 6D:
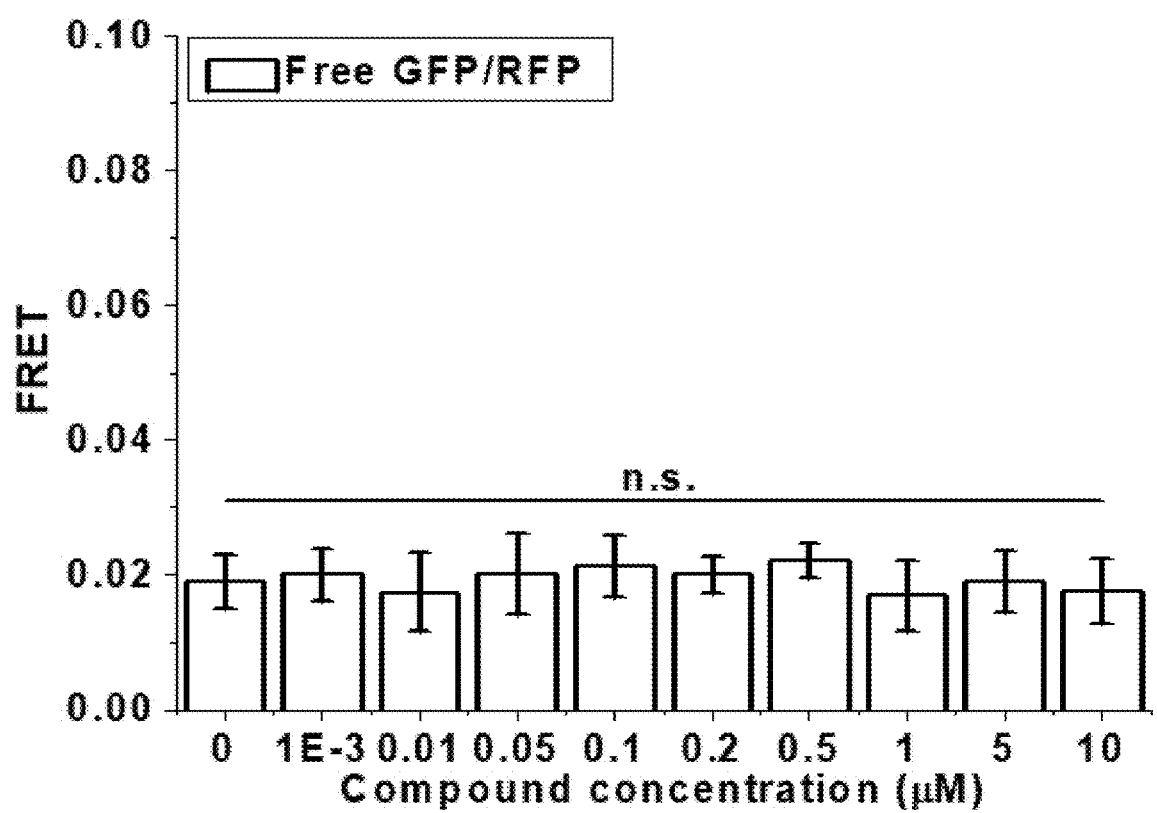

The relative effective concentration ($EC_{50}$) of MK-886 was determined by in-cell FRET measurements using the WT tau biosensor. The compound decreased FRET efficiency in a dose-dependent manner with an $EC_{50}$ value of 1.40 μM (FIG. 4D). We also performed a FRET dose response using P301L tau FRET biosensor. The FRET efficiency of this biosensor was found to be higher than that of WT tau biosensor (FIG. 5A) which is consistent with the known tendency of P301L tau to be hyperphosphorylated and hence more oligomeric [54]. Similar to WT, we observed a dose-dependent decrease in the FRET efficiency of the P301L tau biosensor with MK-886 with an $EC_{50}$ value of 1.84 μM (FIG. 4D), confirming that the hit compound also remodels tau oligomers in a disease-relevant model. Interestingly, we observed that MK-886 lowered the FRET level of P301L biosensor to the basal FRET level of WT tau biosensor. This may suggest that MK-886 disrupts the toxic oligomers of P301L tau and converts them to less toxic conformations that are similar to the conformations adopted by the WT tau. In addition, we confirmed that the small molecule was acting specifically on tau and was not acting on the cytosolic fluorophores (FIG. 6B-D). Assay quality (Z') was determined using MK-886 (Eq. 2). The Z' value of 0.72±0.02 indicates excellent assay quality, validating MK-886 as a positive control tool-compound for targeting tau oligomers.

Figure 7A:
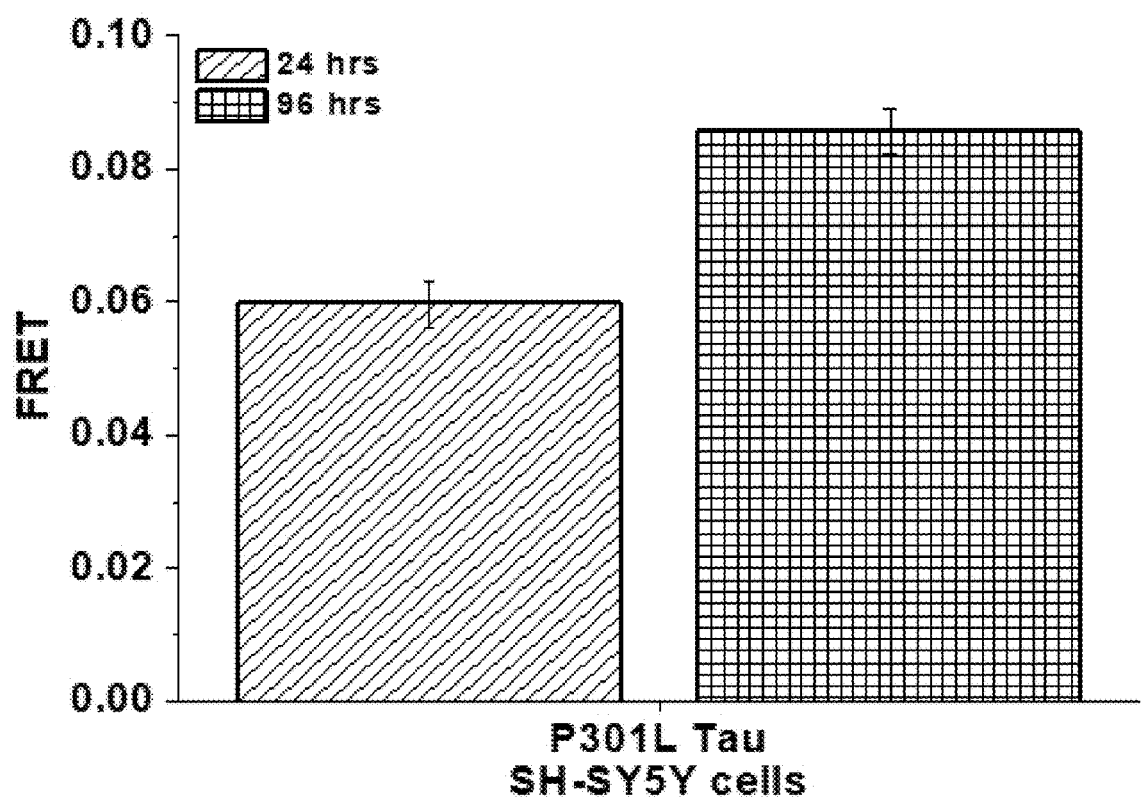
FIGS. 7A-7B show effect of MK-886 on P301L tau FRET biosensor expressed in SH-SY5Y cells.
Figure 7B:
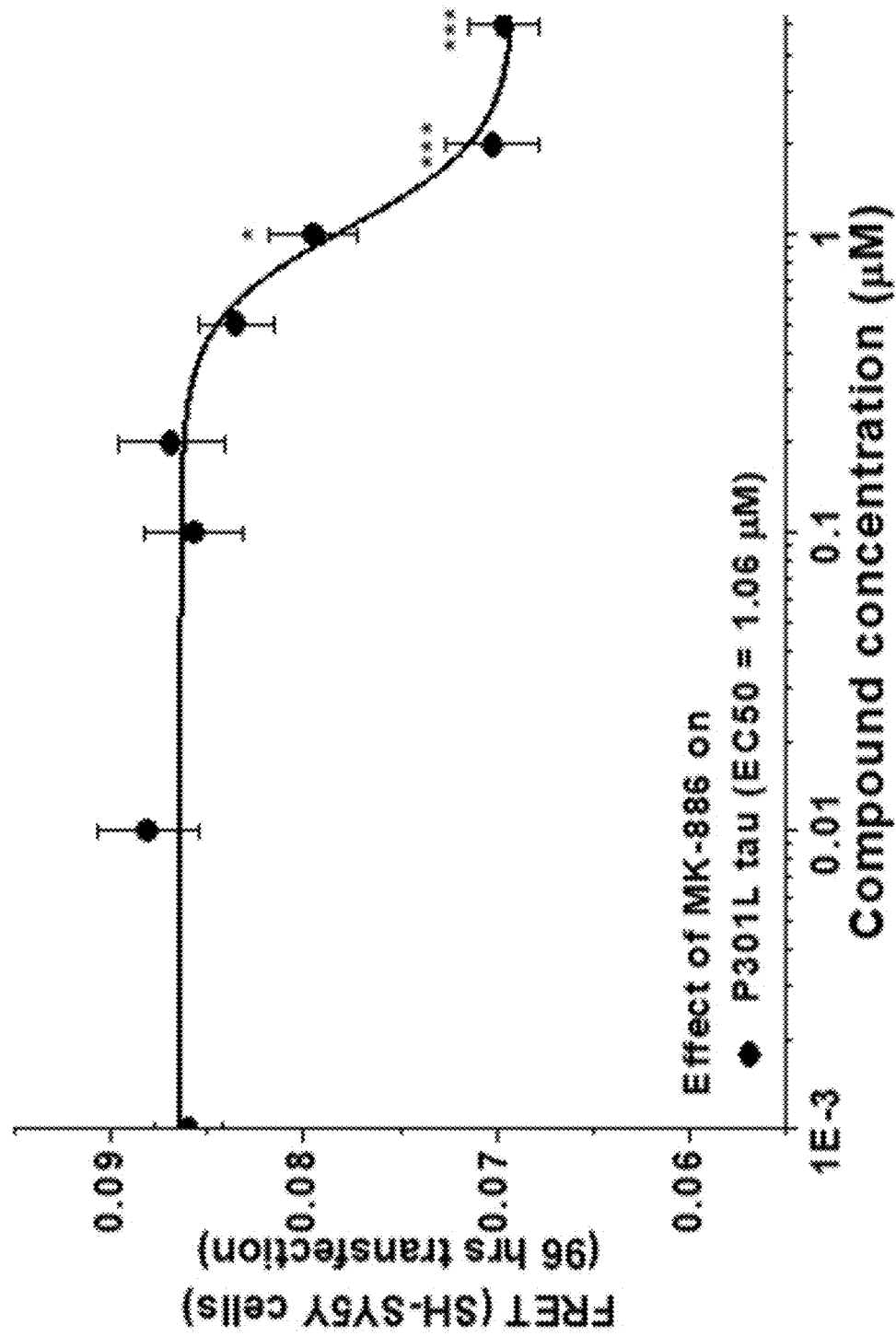

We also expressed the P301L tau FRET biosensor in the SH-SY5Y neuronal cell model, and similar FRET was observed as in the HEK293 cells (FIG. 7A). This FRET again reflects the formation of oligomers, as it is known that β-sheet fibrils do not spontaneously form in SH-SY5Y overexpressing P301L tau unless aggregation inducers are used [52]. MK-886 reduced FRET from P301L tau biosensor in the SH-SY5Y cells with an EC50 of 1.06 μM (FIG. 7B). Importantly, as will now be shown, if toxicity is observed when P301L tau is overexpressed in SH-SY5Y cells, and the toxicity is rescued by MK-886, it will further support the conclusion that the small molecule converts toxic tau oligomers into a non-toxic conformational state.

Figure 8A:
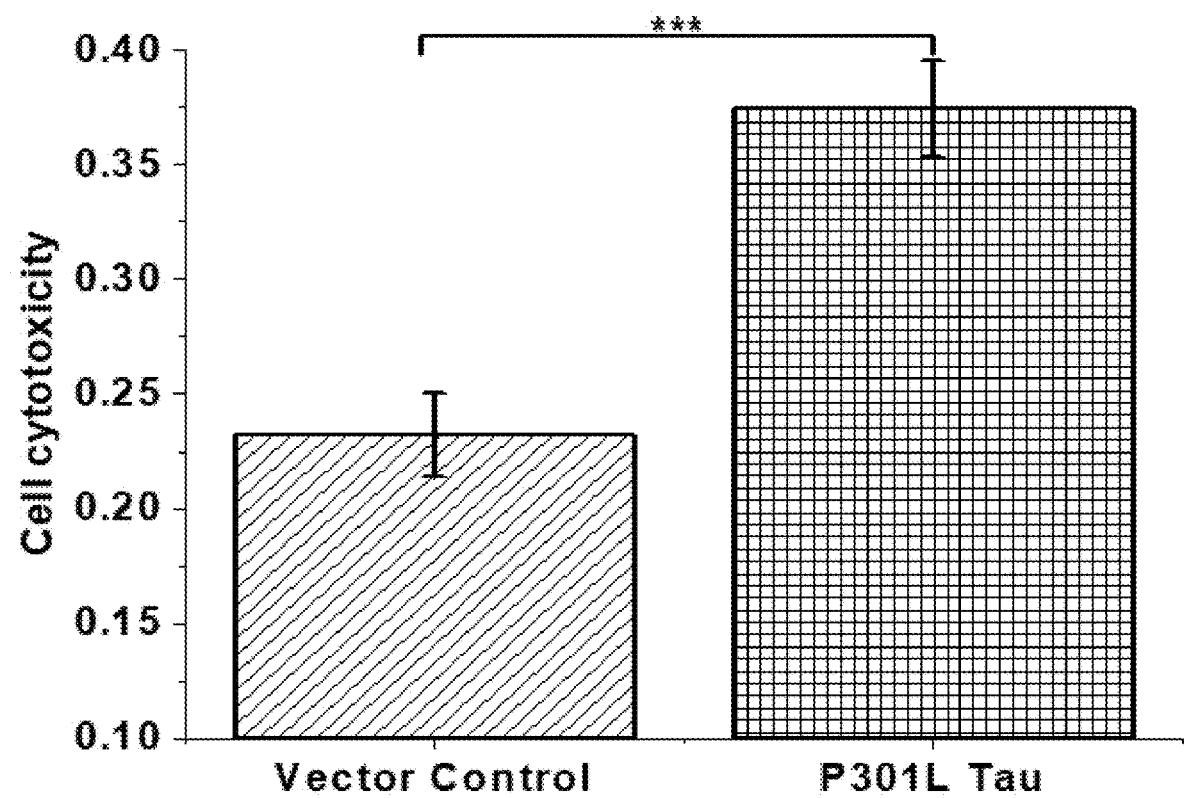
FIGS. 8A-8B show rescue of tau induced cell cytotoxicity in SH-SY5Y human neuroblastoma cells by MK-886.
Figure 8B:
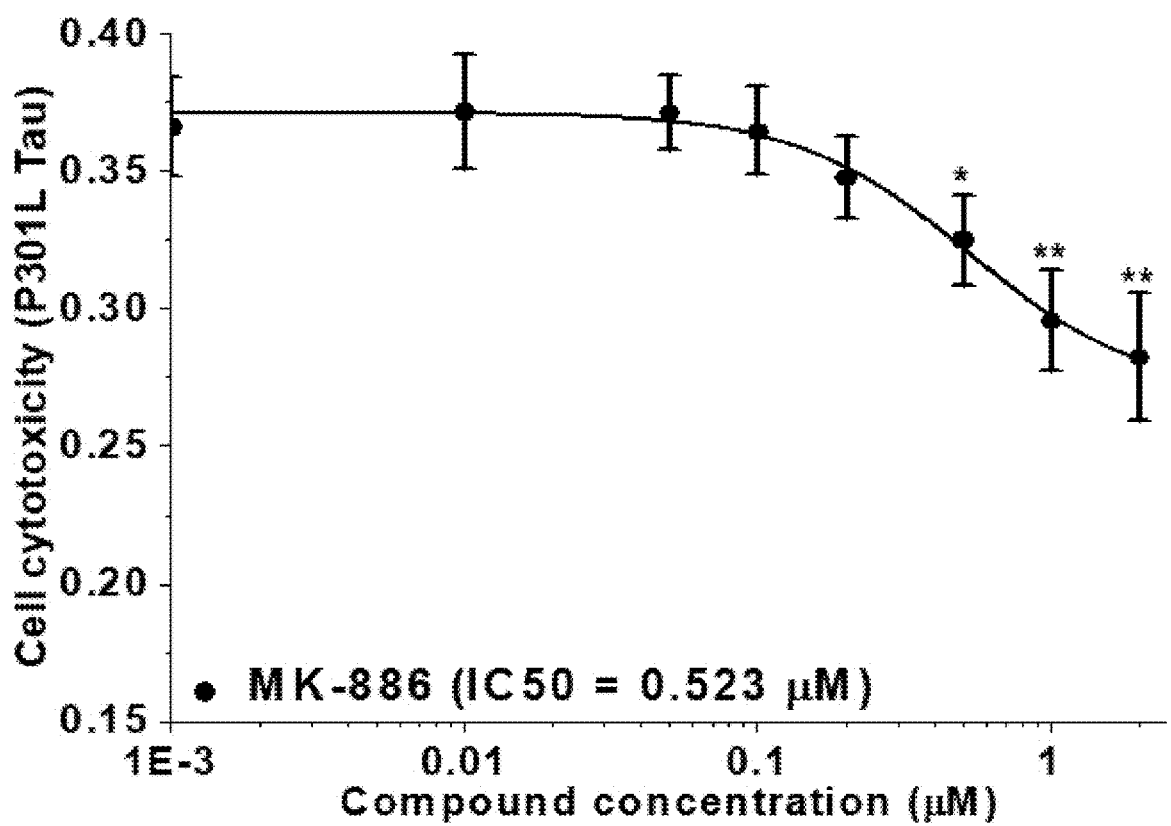
Figure 9A:
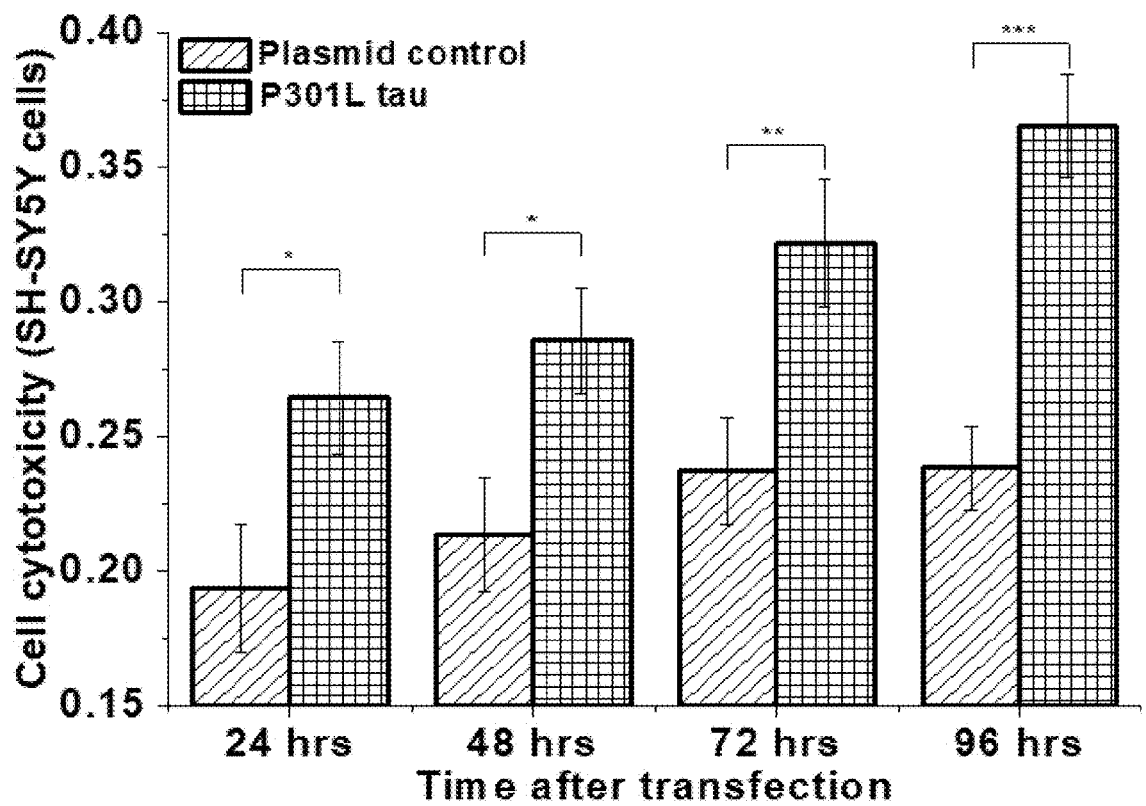
FIGS. 9A-9C show characterization and controls for P301L tau induced cell cytotoxicity assay in SH-SY5Y cells.

MK-886 Reduces Tau Induced Cell Cytotoxicity in SH-SY5Y Cells with Nanomolar Potency We next tested the effect of MK-886 on P301L tau induced cytotoxicity in the SH-SY5Y neuroblastoma cell model of tauopathy [20,32,55,56]. Overexpression of P301L tau showed significantly greater cell death (37%) when compared to the vector-only control (23%) after 96 hours of expression (FIG. 8A and FIG. 9A). Treatment with MK-886 (1 nM to 2 μM) to cells overexpressing P301L tau showed significant rescue of P301L tau induced cytotoxicity in a dose-dependent manner, with an $IC_{50}$ of 0.523 μM (FIG. 8B), the same order of magnitude as MK-886's binding affinity for recombinant P301L tau protein. The two-fold difference in $IC_{50}$ of MK-886 in the cell cytotoxicity assay (0.523 μM) and the $EC_{50}$ from the FRET assay (1.06 μM) may be due to the different treatment conditions as well as the expression of unlabeled vs. fluorophore-tagged P301L tau in each assay respectively.

Figure 9B:
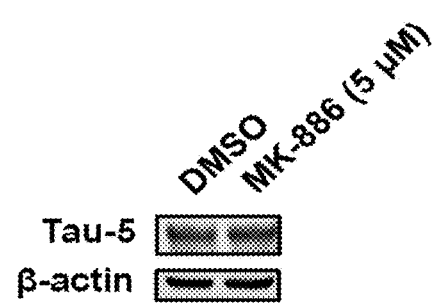
Figure 9C:

We note that MK-886—which was blindly identified in our HTS—has been shown to play a role in modulating AD-related amyloid and tau pathology through inhibition of 5-lipoxygenase (5-LOX)-activating protein (FLAP) [57], potentially altering the clearance and phosphorylation state of tau [58,59]. Our observations suggest that MK-886 rescues tau induced cytotoxicity through direct binding to tau protein and not by modulating FLAP, a previously undescribed mechanism of action. SH-SY5Y cells do not express 5-LOX or FLAP and therefore are a particularly well suited model to evaluate alternative MOA for MK-886 rescue of tau induced cytotoxicity [60]. We also confirmed that there were no changes in the relative levels of expressed tau (FIG. 9B) or the phosphorylation state (FIG. 9C) due to MK-886 treatment in the SH-SY5Y cell model, although it remains possible that MK-886 may be altering other PTMs such as acetylation or oxidation.

Figure 10A:
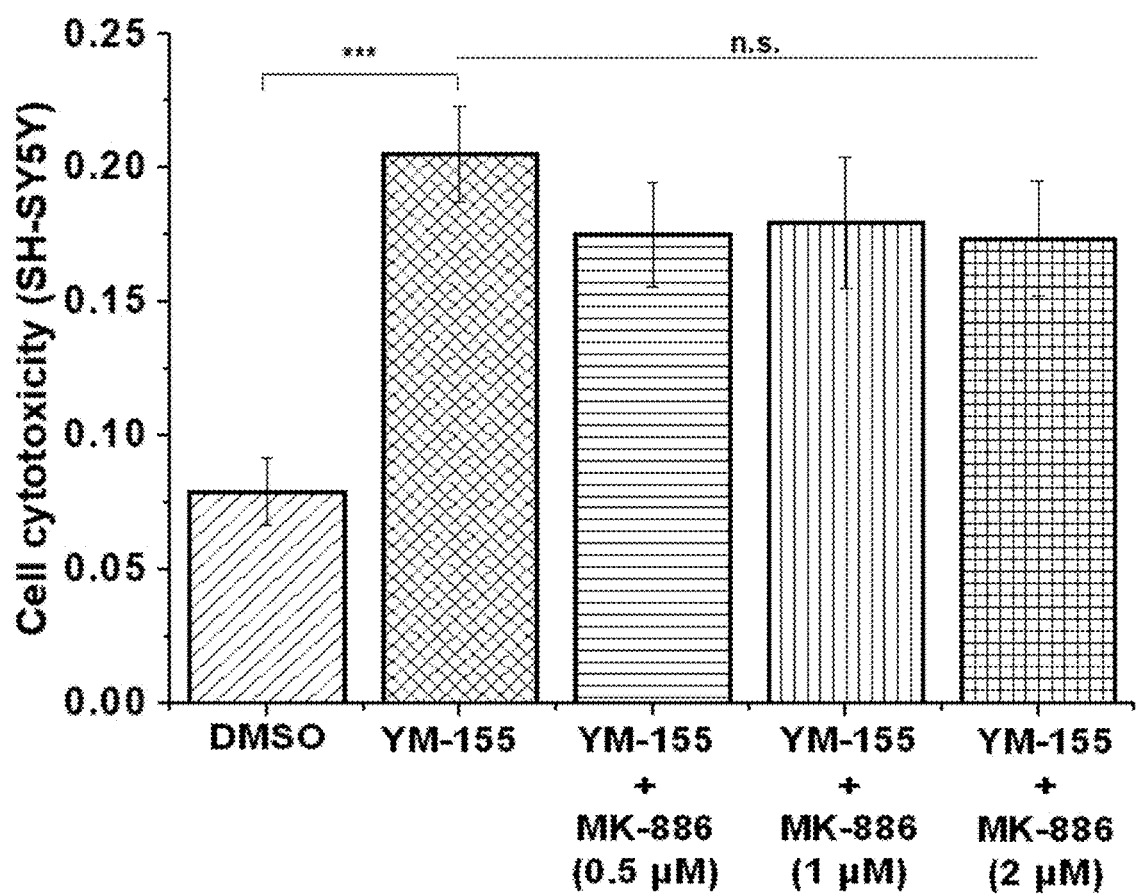
FIGS. 10A-10B show effect of MK-886 on cell cytotoxicity induced by suppressors of survivin, inhibitor of apoptosis proteins (IAPB) or X-linked inhibitor of apoptosis proteins (XIAP). Both (FIG. 10A) YM-155 and (FIG. 10B) UC-112 induced cell cytotoxicity in SH-SY5Y cells and MK-886 does not rescue any cell death caused by these compounds. Data are means±SD of three independent experiments. *P<0.001 and **P<0.0001 by two-tailed unpaired t test.
Figure 10B:
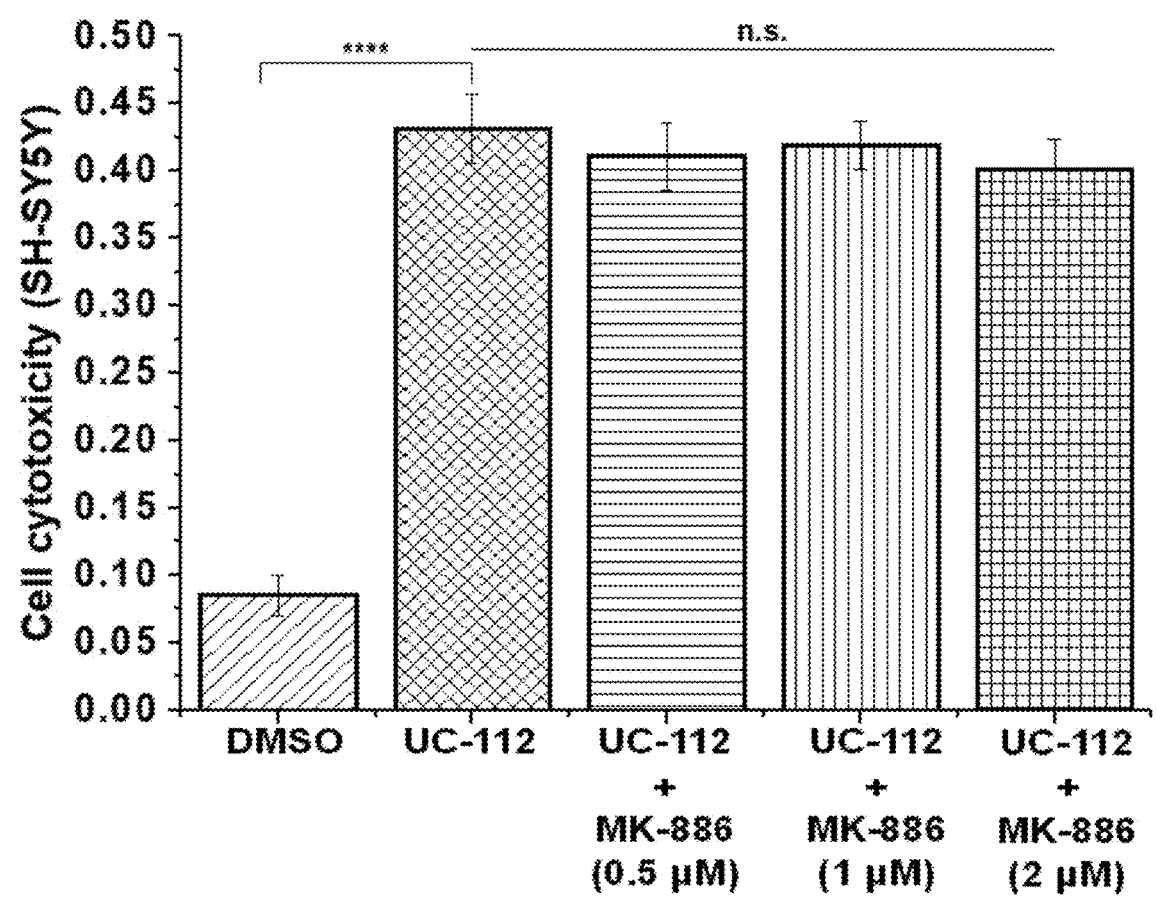

In addition, it has been shown that expression of P301L tau may also result in cell death through down-regulating the expression of survivin, inhibitor of apoptosis proteins (IAPB) or X-linked inhibitor of apoptosis proteins (XIAPs) [55]. Thus, we needed to rule out the possibility that MK-886 rescues P301L tau induced cell cytotoxicity by modulating the expression of these genes, rather than by directly altering tau conformations. To do so, we used two small molecules (YM-155 and UC-112) that are potent suppressors of the expression of survivin, IAPB and XIAPs, thus mimicking the effect of P301L tau on this pathway. This allowed us to test whether MK-886 can rescue cell cytotoxicity in the absence of P301L tau, simply by upregulating these survival genes [61]. Our results showed that MK-886 did not rescue the cell cytotoxicity induced by YM-155 (1 μM) or UC-112 (1 μM) (FIG. 10A-B). Thus, these important control experiments strongly suggest that MK-886 rescues P301L tau induced cell cytotoxicity by directly perturbing the conformations of the toxic tau oligomers to form a non-toxic conformation.

Figure 11A:
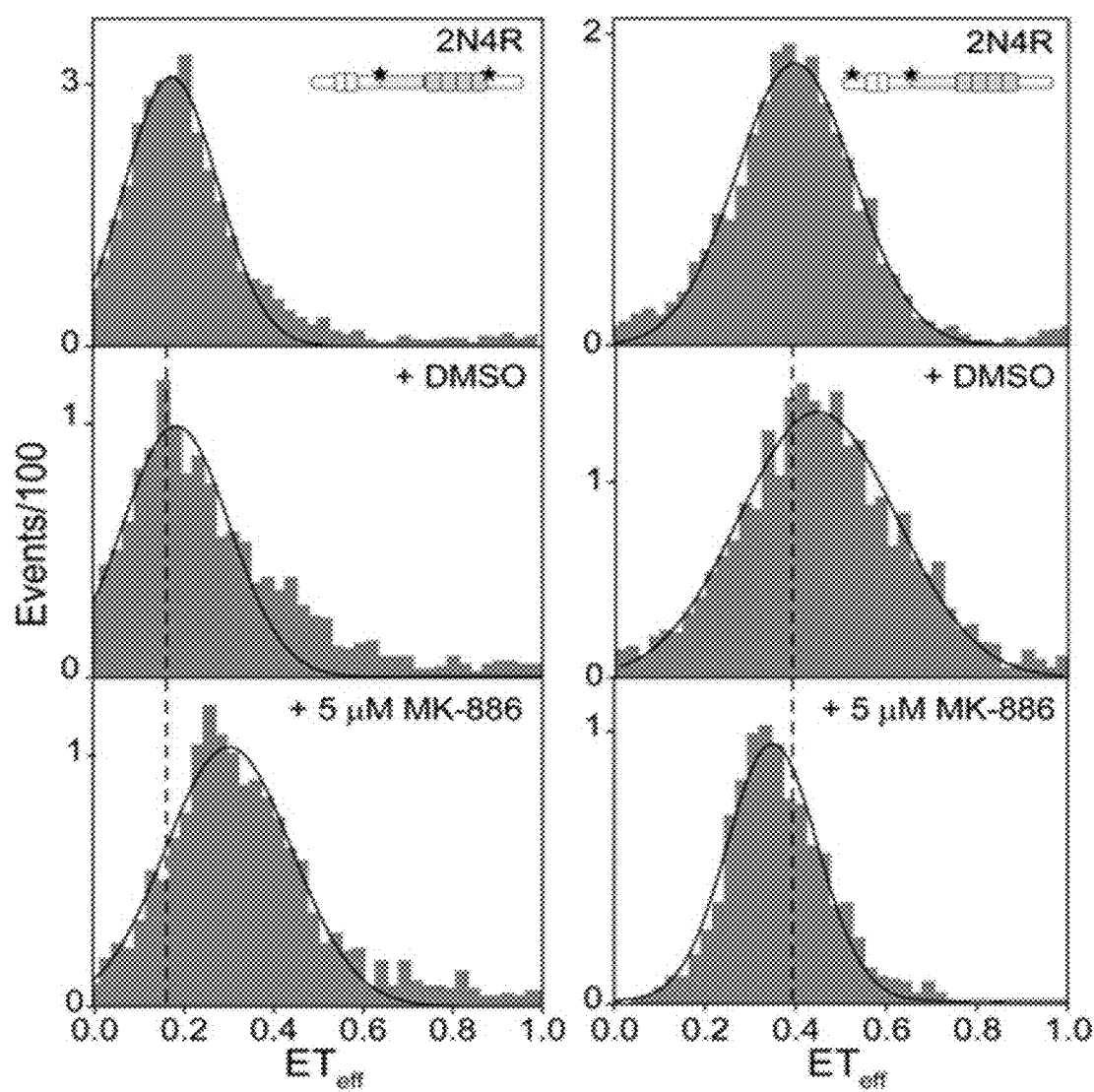
Figure 11B:
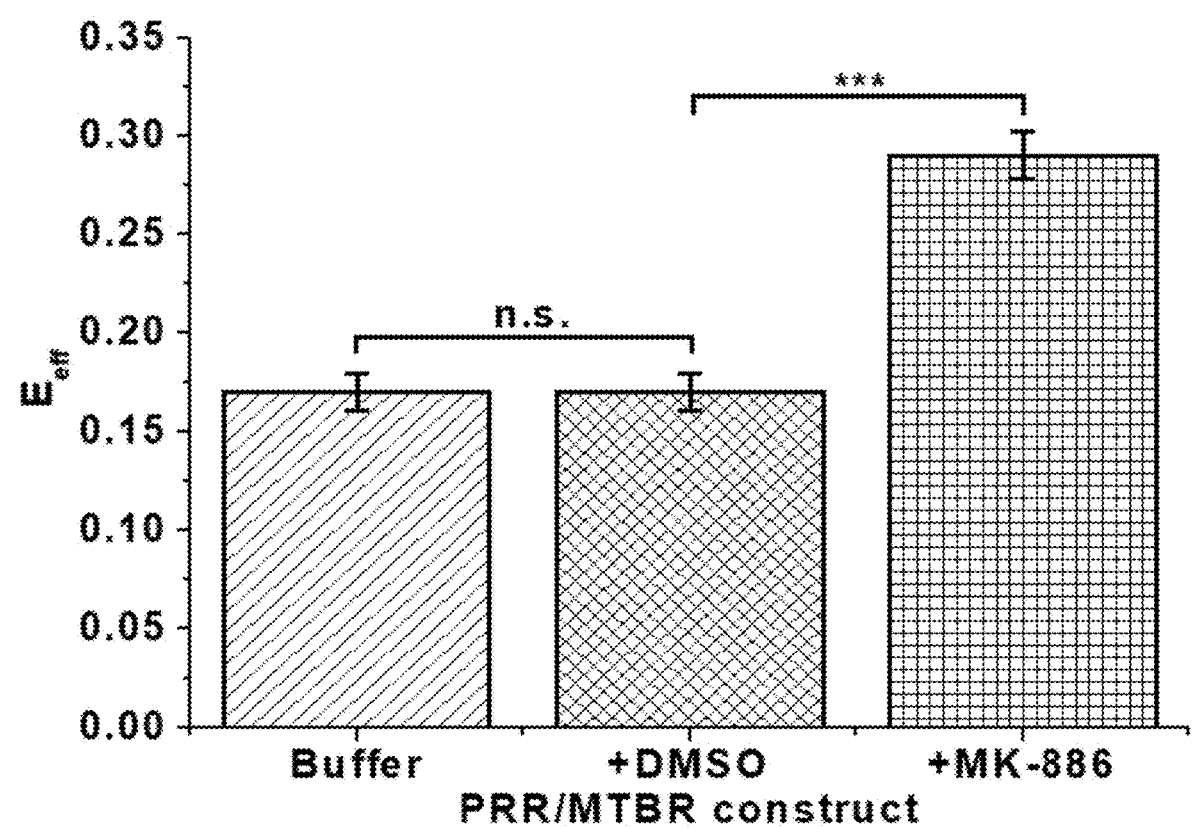
(FIG. 11B) Quantification of the smFRET measurements indicates that the PRR/MTBR becomes substantially more compact (increase in FRET) upon binding MK-886 (5 µM) (A, bottom left) when compared to tau in buffer (A, top left) or DMSO (A, middle left) while the N-terminal domain (FIG. 11C) shows only minor differences in the presence of MK-886 (5 µM) (A, right).
Figure 11C:
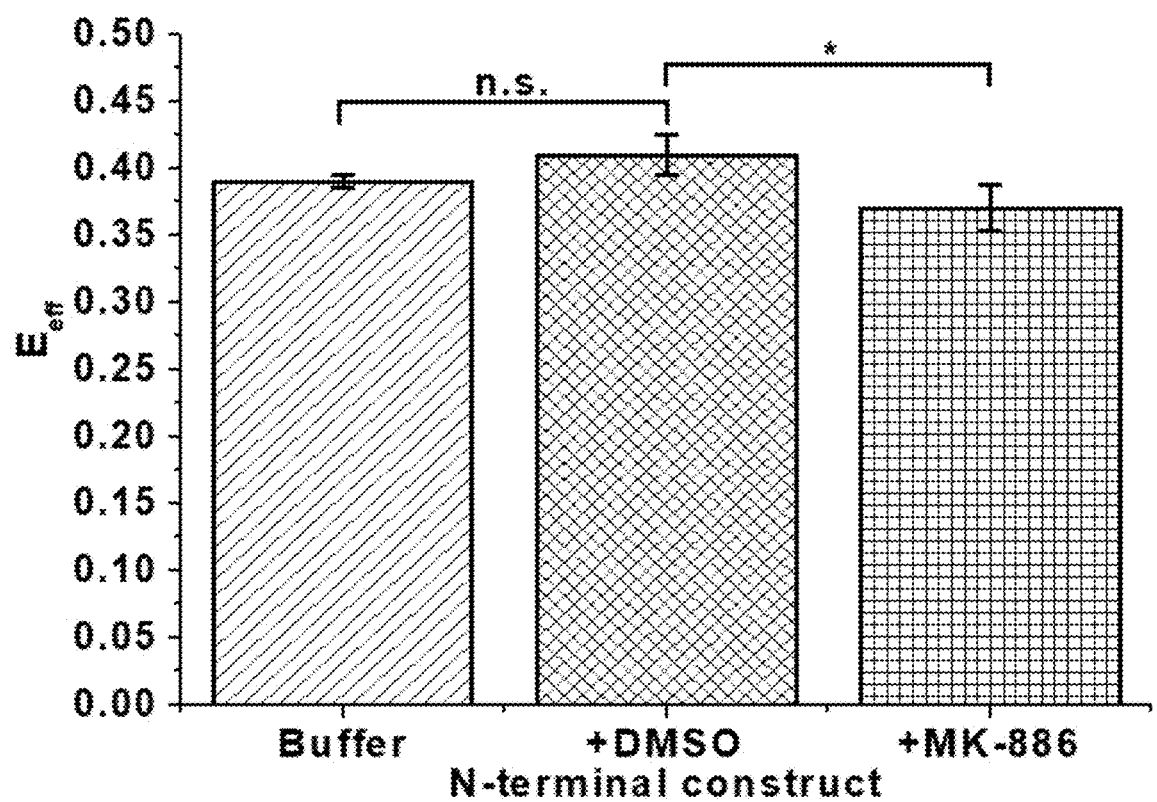
Figure 11D:
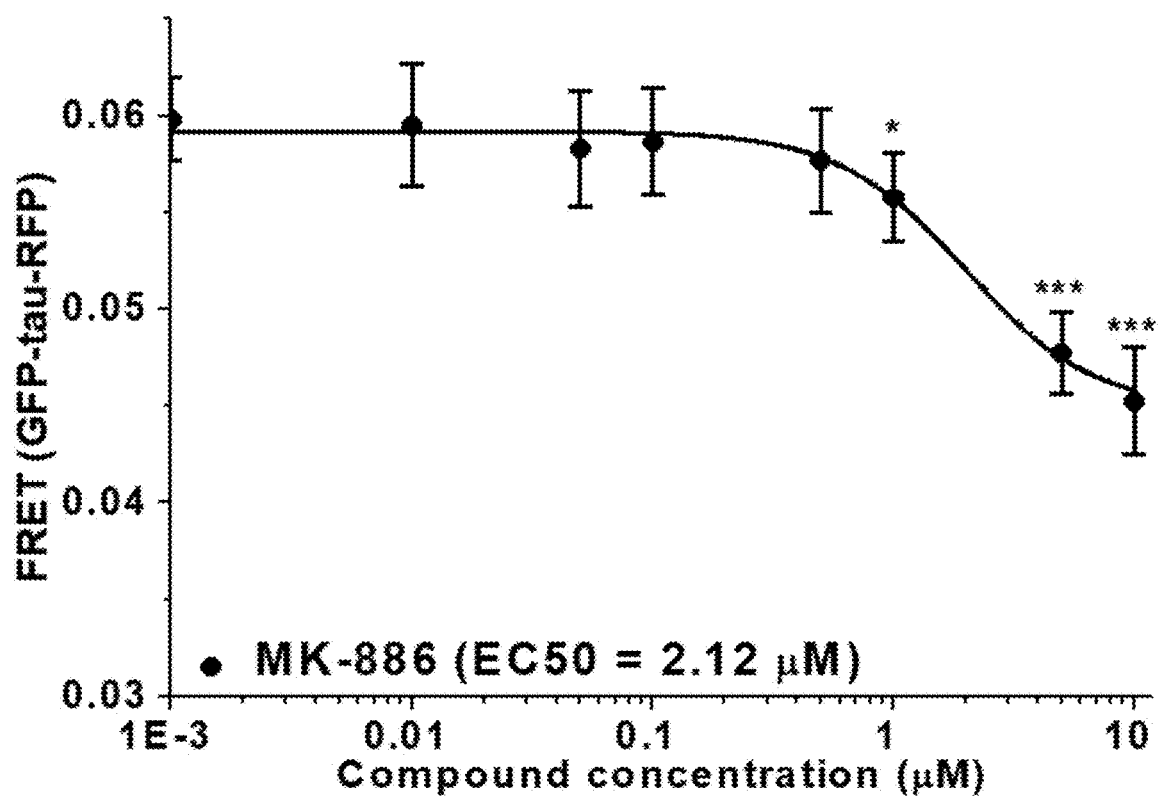
(FIG. 11D) FRET analysis of the dose response of MK-886 in the cellular tau intra-molecular biosensor indicates an $EC_{50}$ value of 2.12 µM, similar to that of oligomer modulation, suggesting that the change in conformational states of oligomers is due in part to conformational changes of tau monomer. Data are means±SD of three independent experiments. *P<0.05, ***P<0.001 and n.s. indicates not significant by two-tailed unpaired t test.
Figure 12:
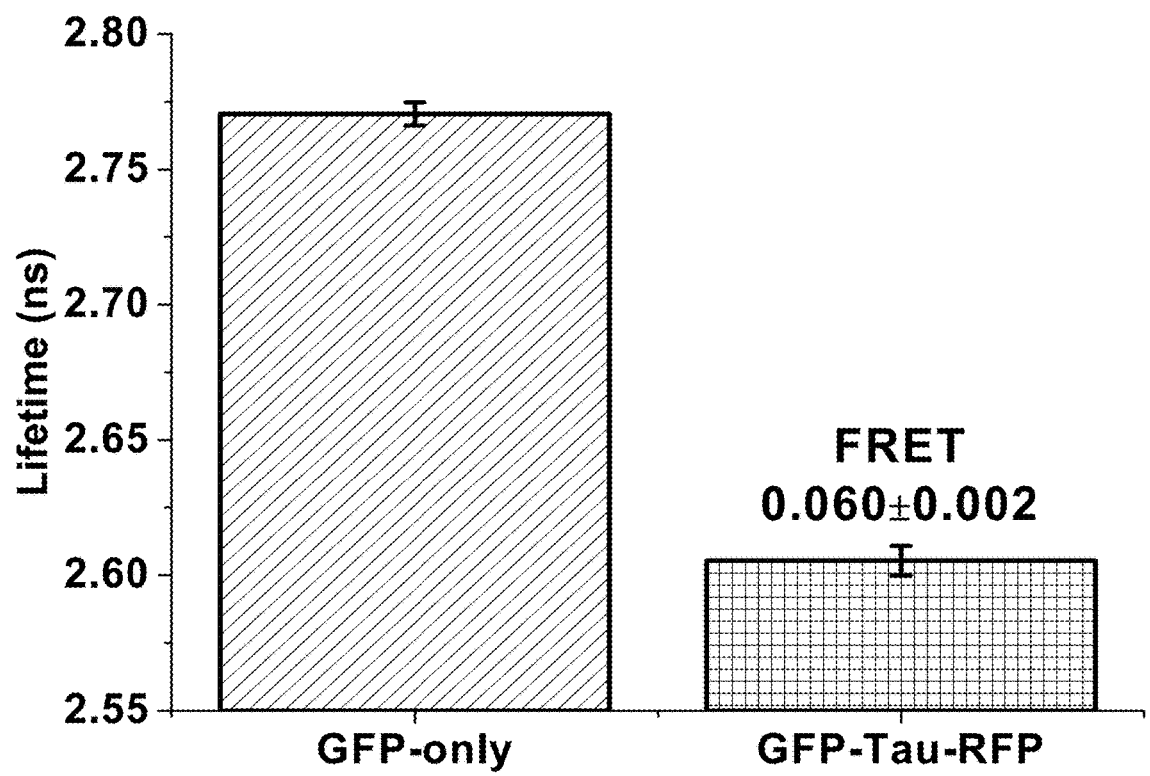
FIG. 12 shows lifetime measurements of the basal FRET of the cellular tau intra-molecular biosensor. The cellular tau intra-molecular FRET biosensor shows an efficient basal FRET, illustrating intra-molecular interactions arising from the paper-clip monomeric structure where the N and C terminus of tau fold in on each other, bringing the GFP and RFP into close proximity. Data are means±SD of three independent experiments.

MK-886 Specifically Perturbs the PRR/MTBR of Tau Monomer and Induces Conformational Changes of the Cellular Tau Intra-Molecular Biosensor To further investigate the MOA of MK-886, we used single-molecule FRET (smFRET) to examine the effect of MK-886 on monomeric tau. Using two different doubly fluorescent-labeled tau constructs (labeled at the proline rich region/microtubule binding region (PRR/MTBR) or at the N-terminal domain) [62], we monitored the conformation of two distinct regions of tau (FIG. 11A). The smFRET shows that MK-886 causes a substantial increase in FRET for the PRR/MTBR targeted construct (FIG. 11B) but only a minor decrease in FRET for the N-terminal domain construct (FIG. 11C). This suggests that MK-886 specifically binds and induces a conformational change in tau monomer at the PRR/MTBR region, resulting in a subsequent loss of interactions between the N-terminal domain and the PRR/MTBR. To determine whether MK-886 also perturbs the monomer conformation of tau in cells, we tested the compound with a cellular tau intra-molecular FRET biosensor (GFP-tau-RFP). The intra-molecular FRET biosensor has a basal 6% FRET signal (FIG. 12), illustrating the intramolecular interactions arising from the paper-clip monomeric structure in which the N- and C-terminus of tau are folded to close proximity [63]. Treatment with MK-886 reduced intra-molecular FRET with an $EC_{50}$ of 2.12 μM, similar to that of oligomer modulation, suggesting that the change in conformational states of oligomers is due in part to perturbation of the tau monomer (FIG. 11D).

It has been suggested that the folding over of tau's two termini to form the classic "paper-clip" structure is due to electrostatic interactions that arise from the opposite net charges of the N-terminal and MTBR domains [63]. While this global folding is specific, it has been shown to be a rather weak interaction [63]. We speculate that the binding of MK-886 to the PRR/MTBR of tau may shield these interactions and lead to an opening of the two termini, resulting in the observed decrease in FRET of the intra-molecular FRET biosensor. From our previous observations with smFRET on tau constructs, this type of conformational change is often accompanied by the PRR/MTBR becoming substantially more compact (increase in FRET) in recombinant protein systems [62].

Figure 13A:
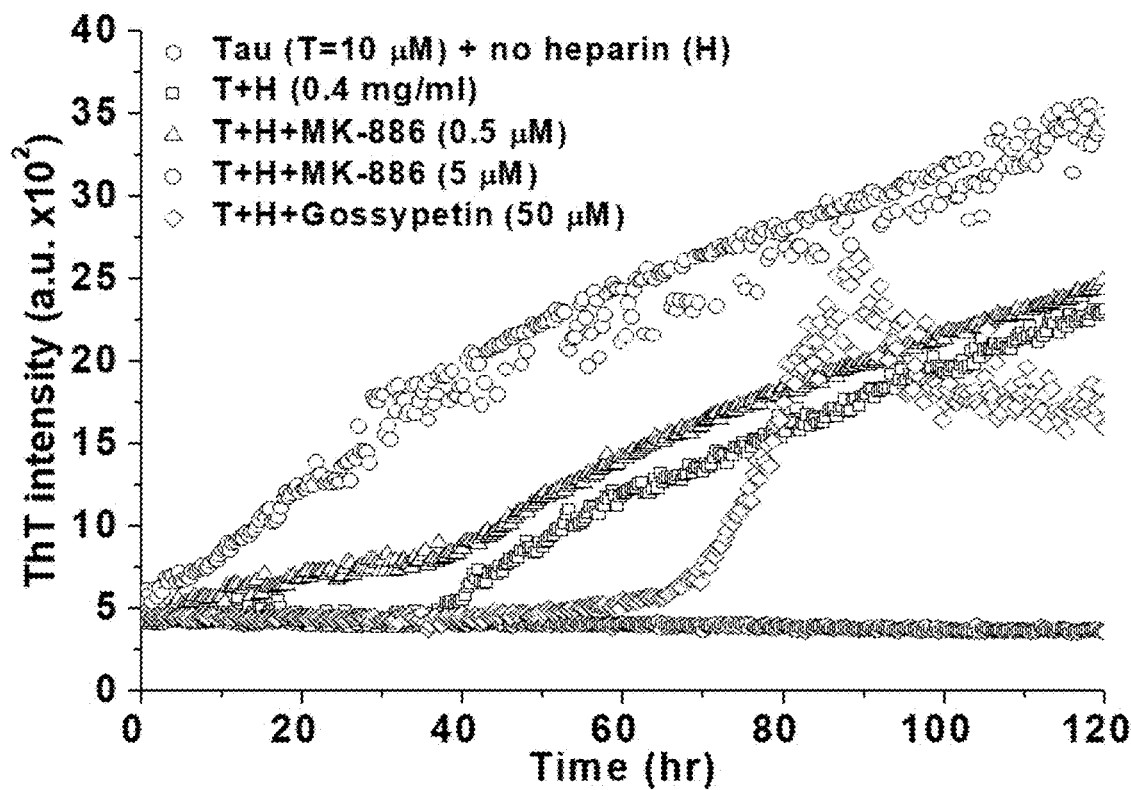
FIGS. 13A-13B show MK-886 alters the ensemble of conformational states of tau oligomers by stabilizing a fibrillization promoting conformation.
Figure 13B:
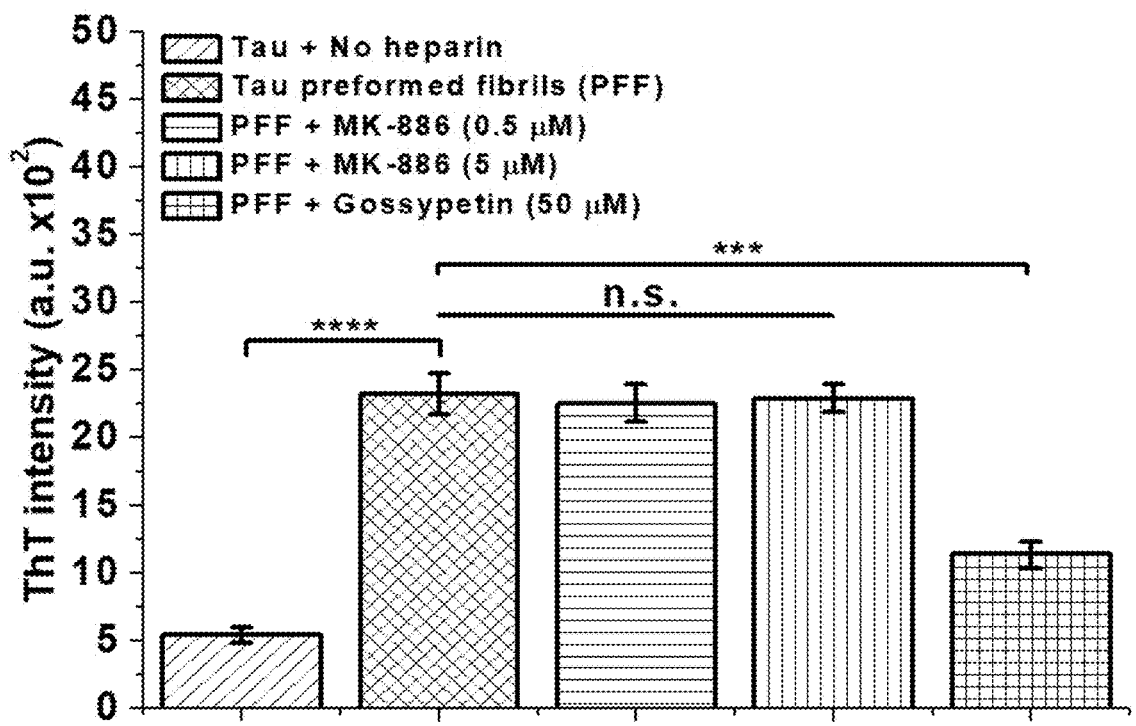
Figure 14A:
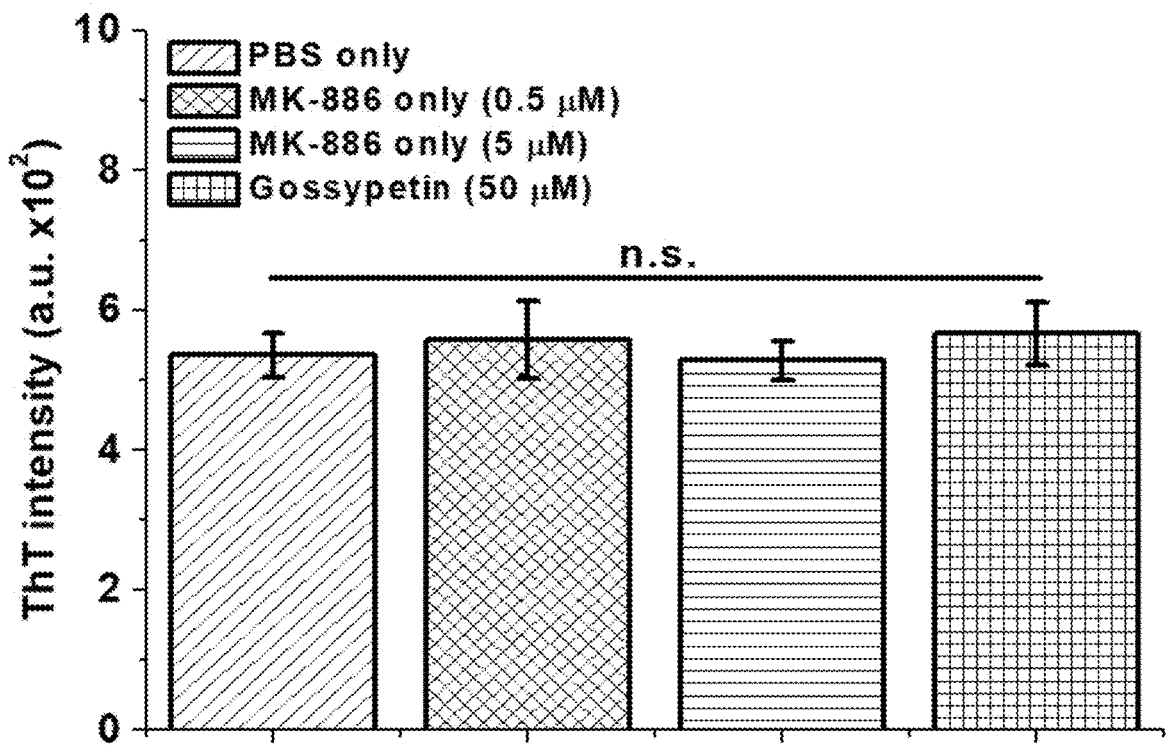
FIGS. 14A-14B show controls for thioflavin-T (ThT) assay with purified WT tau proteins.
Figure 14B:
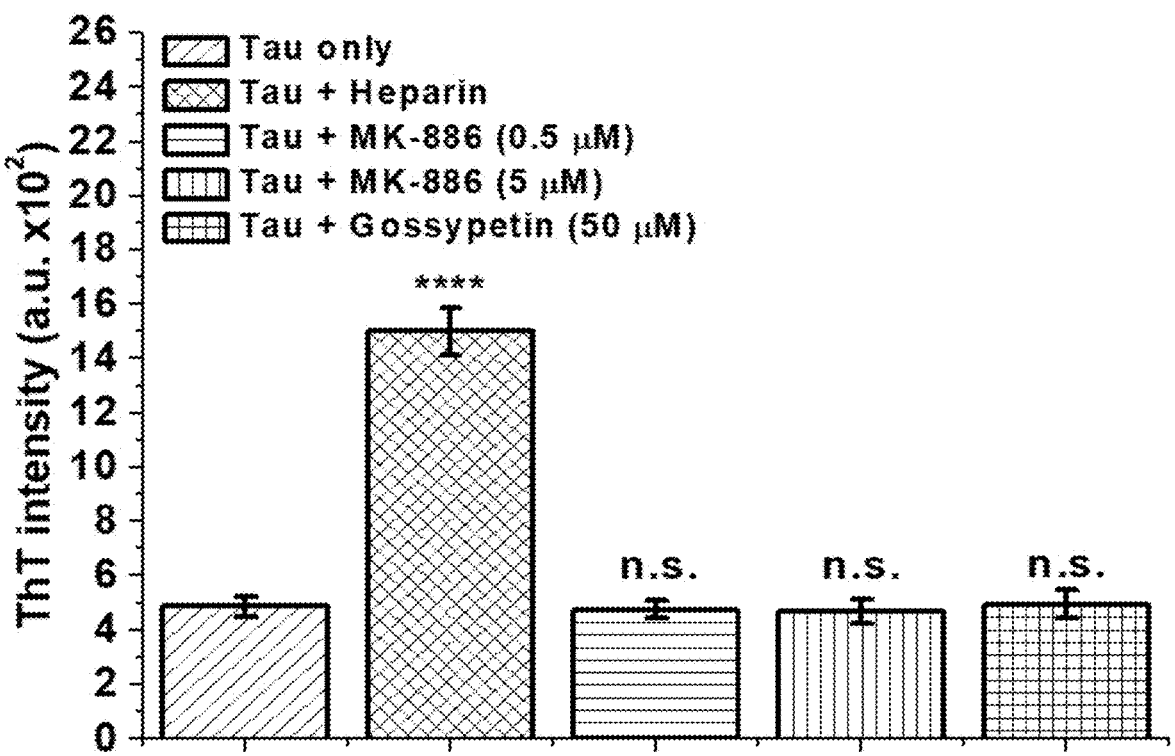

MK-886 Stabilizes Tau Conformations that Promote the Formation of Sheet Positive Fibrils in the Presence of Aggregation Inducer We have shown that MK-886 directly binds to immobilized tau, modulates tau oligomer and monomer conformation (both in cells and purified proteins), and rescues tau induced cytotoxicity. To further explore MK-886's MOA and identify whether MK-886 targets on- or off-pathway oligomers, we performed a heparin induced thioflavin-T (ThT) aggregation assay in the absence and presence of MK-886. MK-886 shortens the lag phase of tau β-sheet fibril formation in a dose-dependent manner (FIG. 13A), suggesting that it induces or stabilizes on-pathway, early-stage species in the amyloidogenic cascade. We confirmed that MK-886 did not have a direct effect on ThT fluorescence (FIG. 14A) and did not act to nucleate for fibril formation (FIG. 14B). In addition, we tested if MK-886 disrupts tau preformed fibrils (PFF). Comparison of MK-886 to gossypetin (a known remodeler of tau fibrils) illustrates that MK-886 did not reduce the ThT signal from tau PFF, whereas gossypetin showed a significant decrease, indicating the disruption of β-sheet fibril structure (FIG. 13B). These results, in combination with the changes in FRET and reduction of tau induced cytotoxicity, suggest that MK-886 alters the conformational ensemble of tau oligomers favoring a subset of non-toxic, on-pathway oligomers that promote tau fibrillization.

b. Future Experiments and Validation Studies

The identity of a specific, toxic tau oligomeric species remains elusive. Indeed, it is unlikely that a single, unique toxic conformation exists. It is far more likely that an ensemble of toxic oligomers (differing in size, conformation, and even molecular constituency) populates the fibrillogenesis cascade [22-28]. This heterogeneity in tau oligomer targets highlights the need for an ultra-sensitive screening platform capable of monitoring structural changes within the ensemble of tau assemblies. Our FRET-based platform for monitoring full-length tau oligomerization in cells is a new technology that is capable of doing this, as well as elucidating novel compounds which alter conformation and oligomerization, thereby providing a new pipeline of therapeutic discovery for tauopathies.

With this technology in hand, we and others are in a position to explore multiple important issues. First, screens will now be done of larger libraries and of libraries built specifically for targeting the central nervous system (CNS) (i.e. favorable blood-brain barrier permeability). These screens will dramatically increase the statistical sampling of small-molecule induced changes in time-resolved FRET (TR-FRET) signatures. With a larger sample, the high information content of TR-FRET can, when complemented with other structural tools (discussed below), be used to cluster compounds into distinct classes based on their myriad of structural effects on the targets [47]. To more adequately generalize the patho-physiological relevance of these clustered structural motifs, we will move to inducible cell lines [43], as well as alternate cell lines including eventually patient-derived induced pluripotent stem cells (iPSC) neurons [64] and iPSC-derived spheroids [65,66]. Additional extensions of this technology for small molecule discovery should include using different cellular models of tau pathology including, among others, modification of the oligomerization trigger through the addition of tau seeds (fibrils, oligomers, or monomer), upregulation of specific kinases or chaperone proteins (e.g. GSK3β or HSP70), and treatment with environmental toxins [14]. This will allow us to examine multiple proposed mechanisms of induced tauopathies, providing key insight into differences between on- and off-pathway oligomerization [67]. Each of these steps will be critical to building a more complete and useful correlation between structural heterogeneity and toxicity.

It will be of great interest to ascertain whether lead compounds are isoform specific or can target multiple distinct isoforms. Broadly speaking, information on isoform-specific oligomerization could be useful in designing more effective, patient-stratified design of clinical trials [68]. The Diamond group pioneered the tau cellular biomarker field with their tau repeat domain (tau-RD) FRET biosensor cells [43]. Use of full-length tau thus expands on the existing technology and should facilitate additional stratification of potential biomarkers present in AD versus other tauopathies. Following Diamond, experiments that compare the sensitivity and relative reactivity of each biosensor to different tauopathy associated biofluids will provide new insight into heterogeneity in tau assemblies inherent in these distinct diseases.

Ultimately, determining and validating the specific MOA by which lead compounds act—be they through direct binding to tau monomers/oligomers or indirectly by altering cellular processes that lead to alterations in oligomers—will require comprehensive approaches to link biophysical experiments with cell biological observables. One set of immediately accessible questions is how the compounds' impact on monomer folding and/or oligomerization relates to tau localization in cells, most obviously on microtubule binding. Here, future work will further probe post-translational modifications (including hyperphosphorylation, which we started here using forskolin) and acetylation, specifically testing how compounds alter the relationship between microtubule unbinding and tau folding/aggregation. As another example, tau has recently been shown to mislocalize to dendritic spines, disrupting synaptic transmission in primary neurons [69]. Whether these or numerous other mechanisms related to mislocalization can explain the cytoprotective effects of lead compounds will require additional experiments. For example, nano-imaging modalities like fluorescence-lifetime imaging microscopy (FLIM) and time-correlated single photon counting (TCSPC) can provide the necessary spatial resolution to correlate subcellular localization (e.g. microtubules, cytosol, mitochondria, etc.) and distinct tau conformations [70].

5. Long Term Hypothesis

The technology described here is based on the hypothesis that tau biosensors expressed in cells can be used to accomplish two complementary, but distinct goals: 1) they can be used to find small molecules that modulate tau toxicity; and 2) they can provide a direct, albeit low-resolution reporting of the structures and conformations of a heterogeneous ensemble of toxic and non-toxic states. For the first part of this hypothesis, namely modulation of toxicity, we have demonstrated the power of our approach with MK-886. The second broader and longer-term hypothesis is built on the idea that biophysical tools, such as TR-FRET, can provide key insight into the unique structural fingerprints of heterogeneous toxic tau oligomers, and that this detail can be exploited in drug discovery. This is a far more nuanced bar, but is nonetheless a goal that should and, we believe, can be tackled. On the one hand, unlike fibrils, oligomers are highly heterogeneous (number of monomers per aggregate, local or transient structural motifs/folds, molecular constituency, etc. . . . ), making it improbable that high-resolution structural biology tools are or ever will be applicable to their study (they simply lack well-defined secondary or tertiary structural elements). On the other hand, the field currently relies only on low-resolution techniques that provide little to no structural information (e.g. antibody recognition, protease protection, detergent resistance). Finding a middle ground requires a set of structural techniques that can adequately and accurately interrogate oligomers, but more crucially can stratify structural fingerprints at a quantitatively useful and reproducible resolution. Absent high-resolution structures, we should nonetheless be able to ask: what are the critical amino acids that dictate oligomer-prone monomer folds and what are the deleterious inter-monomeric amino acid motifs that dictate toxicity? As an example of how this can begin to happen, we complemented our TR-FRET with smFRET, and were able to isolate the region of tau impacted by MK-886 binding. But this is just a start, as far more detailed information should be obtainable using a set of creative and state-of-the-art experimental and computational approaches to interrogate these structures [71-73].

In theory, TR-FRET waveforms contain high-content information that can resolve relative species populations and protein-protein distance distributions [74]. TR-FRET alone does not provide atomic structural resolution to uniquely identify specific species. The process of extracting this structural data from TR-FRET requires model fitting. The challenge is that the model must be constrained by information we do not yet have, including constraints on the stoichiometry of the tau oligomer. This highlights a current limitation in analyzing tau-tau TR-FRET as there are no well-defined structural states and the exact toxic species, including the number of interacting tau monomers, is unknown. To begin to make progress in this regard will require additional biophysical tools. These will include, among others, analytical ultracentrifugation (AUC) and analytical gel filtration for oligomer size. Despite the promise of these techniques for grouping oligomeric species into meaningful clusters, doing so in cells will be the greatest challenge moving forward. Higher resolution structural information for stratifying oligomeric species can be obtained in purified, in vitro assemblies using other spectroscopic techniques such as nuclear magnetic resonance (NMR) and electron paramagnetic resonance (EPR). However, because tau oligomers in cells likely consist of other molecular constituents and are folded with the help of chaperones, there is a real danger in relying too heavily on the folding of these assemblies outside of the native cellular environment. There have been recent advances that allow for the use of high-resolution techniques, such as NMR, in cells [75-77].

6. Linkage to Other Major Theories

Tauopathies have a vast heterogeneity in their clinical presentations (e.g. AD, fronto-temporal dementia and movement disorders, amongst others) [78] which is one of the major challenges that plagues current clinical trials [79]. This heterogeneity may be explained in part by strong histopathologic differences and differential laminar and regional brain distributions. For therapeutic intervention, an equally important potential source of this heterogeneity is molecular variations such as isoform composition and post-translational modifications [78,80]. Hence, there is a need for robust tools and/or biomarkers to stage and delineate (particularly, at the molecular level) the numerous different tauopathies.

Although our biosensors and HTS technology are focused on the oligomer hypothesis of tauopathy, they are directly translatable into other areas of tauopathy research and therapeutic discovery. The presence of misfolded tau and the formation of the tau oligomers can be attributed to upstream dysfunctions in neurophysiology and axonal transport. For example, mitochondrial dysfunction and oxidative stress are believed to be a prominent early event in the pathogenesis of AD, contributing to tau phosphorylation and the formation of neurofibrillary tangles [81]. In particular, deterioration of mitochondrial functions such as impairments in the activity of Krebs cycle enzymes and electron transport machineries (e.g. cytochrome c oxidase (COX)) have been correlated with severity in the clinical state of tauopathies and AD [9,10]. Importantly, impaired COX activity can potentiate the generation of mitochondrial-derived reactive oxidative species (ROS), suggesting that defective mitochondrial bioenergetics and oxidative stress are coupled in a vicious cycle [10]. It has also been shown in that in familial AD, tau and amyloid-beta (Aβ) can augment the pathological deterioration of mitochondrial function [82]. In addition, there is compelling evidence that tau can play a role in controlling motor protein—driven vesicle transport along microtubules [83]. Furthermore, there is an age-dependent decline in axonal transport rates which correlates with increases in hyperphosphorylated tau [11]. Our FRET biosensors can be used to study these effects. For example, we can use the intra-molecular biosensor to study the global tau folding when it is bound to microtubules versus when it is detached from microtubules. Our inter-molecular biosensor can also be used to monitor the kinetics and the extent of free soluble tau that are detached from microtubules and start to form oligomers, providing important fundamental information in understanding early stage events underlying tau pathology.

Misfolded or oligomerized tau can be a symptom, as much as a cause, of an underlying pathology. Despite our focus on disrupting oligomers, using the cellular tau biosensors to modulate upstream effectors of tau dysfunction may actually hold the most promise. The TR-FRET screen in cells does not discriminate between compounds that act directly on tau folding/oligomerization and those that operate indirectly by binding to other upstream targets. Coupling secondary biophysical assays to the screen allows us to elucidate direct versus indirect MOA. Compounds that act through an indirect MOA—e.g. those that rescue dysfunctional autophagy or mitochondrial functions, endoplasmic reticulum or oxidative stress—can provide insight into specific pathways that are disrupted in tauopathy, giving rise to novel therapeutic targets and strategies. Upon inspection, this appears likely the case for several of the compounds we identified in our screen but whose MOA we have not yet elucidated. Two of these compounds (bumetanide and torsemide) are both loop diuretics which inhibit the sodium-potassium-chloride cotransporter (NKCC1) in vascular smooth muscle and have been shown to reduce the risk of AD dementia in both adults with normal cognition or with mild cognitive impairments [84]. The other two hits (benzbromarone and triclosan) have been shown to attenuate oxidative stress [85] and induce autophagy [86] (respectively), both known cellular dysfunctions in AD.

The expression of tau in a stable or inducible cell line as well as in human iPSCs will further improve conditions for screening in a native environment. In addition, we will launch further HTS campaigns using the tau FRET biosensors to screen CNS-focused libraries such as the CNS-MPO or CNS-Set library to ensure small molecules have a high probability of crossing the blood-brain barrier. In conjunction with smFRET and other techniques such as AUC, the biosensors can be used to develop a clearer picture of how mutations (e.g. P301L), different tau isoforms and post-translation modifications alter the conformations of oligomers, and what determines toxicity. Ultimately, the functional effect of the hit compounds will be tested in animal models with tau oligomer induced pathology to see if they rescue the pathology. If the compounds are functional in the animal models, they will be poised to be tested in clinical trials. As for biomarkers development, an immediate next step is to compare our biosensor with the existing tau-RD FRET biosensor developed by the Diamond group to test their sensitivity in cerebrospinal fluid (CSF) from AD patients. If our biosensor is sensitive to these patient samples, we can then further investigate how different groups of patient samples may have different effects on our FRET biosensor. This will act as an initial step in potentially stratifying the patients into different groups to be tested in clinical trials for more effective targeting and drug discovery.

Materials and Methods

Molecular Biology

To generate tau-GFP and tau-RFP, cDNA encoding full-length 2N4R tau (441 amino acids) was fused to the N-terminus of EGFP and TagRFP vectors. The P301L mutation was introduced by QuikChange mutagenesis (Agilent Technologies, Santa Clara, Calif.) and sequenced for confirmation. The GFP-tau-RFP was generated by fusing the N-terminal of tau to the C-terminus of GFP and the C-terminus of tau to the N-terminus of RFP. All constructs contain the monomeric mutation A206K to prevent constitutive fluorophore clustering [88].

Cell Culture and Generation of Stable Cell Lines

HEK293 and SH-SY5Y cells (ATCC) were cultured in phenol red-free Dulbecco's Modified Eagle Medium (DMEM, Gibco) supplemented with 2 mM L-Glutamine (Invitrogen), heat-inactivated 10% fetal bovine serum (FBS HI, Gibco), 100 U/ml penicillin and 100 µg/ml streptomycin (Gibco). Cell cultures were maintained in an incubator with 5% $CO_2$ (Forma Series II Water Jacket $CO_2$ Incubator, Thermo Scientific) at 37° C. Both the WT and P301L tau inter-molecular FRET biosensor were generated by transiently transfecting HEK293 cells using Lipofectamine 3000 (Invitrogen) with WT or P301L tau-GFP and tau-RFP (1:20 DNA plasmid concentration ratio). The effectiveness of HEK293 cells transfected with FRET constructs as a HTS platform has been demonstrated in our previous work [46, 47]. P301L tau inter-molecular FRET biosensor was also transiently expressed in SH-SY5Y cells using Lipofectamine 3000 (Invitrogen). To generate stable cell lines expressing GFP-tau-RFP or tau-GFP only, HEK293 cells were transiently transfected using Lipofectamine 3000 with GFP-tau-RFP or tau-GFP DNA plasmids. Transiently transfected cells were treated with G418 (Enzo Life Sciences, Farmingdale, N.Y.) to eliminate non-expressing cells. Stable cell lines expressing GFP-tau-RFP or tau-GFP with the largest population of expressing cells were selected by fluorescence microscopy. The GFP-linker-RFP (linker contains 32 amino acids, GFP-32AA-RFP) control stable cell line was generated as described previously [89]. The control cells expressing only free soluble fluorophores (GFP or RFP only) were generated by transiently transfecting HEK293 cells using Lipofectamine 3000 with plasmids containing GFP or RFP DNAs at the same plasmid concentration as the inter-molecular tau FRET biosensor.

Pilot Screening with NIH Clinical Collection (NCC) Library

The NIH Clinical Collection (NCC) library, containing 727 compounds, was purchased from Evotec (Hamburg, Germany), formatted into 96-well mother plates using an FX liquid dispenser, and formatted across three 384-well plates at 50 nL (10 µM final concentration/well) using an Echo liquid dispenser. DMSO (matching % v/v) was loaded as in-plate no-compound negative controls to make a total of 960 wells. The 384-well flat, black-bottom polypropylene plates (PN 781209, Greiner Bio-One) were selected as the assay plates for their low autofluorescence and low interwell cross talk. The plates were sealed and stored at −20° C. until use. Two days prior to screening, HEK293 cells were transfected using Lipofectamine 3000 with WT tau-GFP/RFP (WT tau FRET biosensor) in 15×100 mm plates (5×10$^6$ cells/plate) and the stable tau-GFP cell line (donor-only control) was expanded in five 225 cm$^2$ flasks. On each day of screening, the compound plates were equilibrated to room temperature (25° C.). The cells were harvested from the 100 mm plates by incubating with TrypLE (Invitrogen) for 5 min, washed three times in PBS by centrifugation at 300 g and filtered using 70 µm cell strainers (BD Falcon). Cell viability, assessed using a trypan blue assay, was >95%. Cells were diluted to 1 million cells/ml using an automated cell counter (Countess, Invitrogen). Expression of tau-GFP and tau-GFP/RFP (tau FRET biosensor) was confirmed by fluorescence microscopy prior to each screen. After resuspension and dilution in PBS, the biosensor cells were constantly and gently stirred using a magnetic stir bar at room temperature, keeping the cells in suspension and evenly distributed to avoid clumping. During screening, cells (50 µl/well) were dispensed by a Multidrop Combi Reagent Dispenser (Thermo Fisher Scientific) into the 384-well assay plates containing the compounds and allowed to incubate at room temperature for 2 hours before readings were taken by the fluorescence lifetime plate reader (Fluorescence Innovations, Inc) as described previously [46,47].

HTS and Fluorescence Lifetime Data Analysis

As described previously [46,47], time-resolved fluorescence waveforms for each well were fit with single-exponential decays using least-squares minimization global analysis software to give donor-acceptor lifetime ($\tau_{DA}$) and donor-only lifetime ($\tau_D$). FRET efficiency (E) was then calculated based on Equation 1.

$$E = 1 - \left(\frac{\tau_{DA}}{\tau_D}\right) \qquad \text{Eq. 1}$$

Assay quality was determined with the lead compound (MK-886) as positive control and DMSO as a negative control and calculated based on Equation 2 [90], $$Z' = 1 - \frac{3(\sigma_p + \sigma_n)}{|\mu_p - \mu_n|} \qquad \text{Eq. 2}$$

where $\sigma_p$ and $\sigma_n$ are the standard deviations (SD) of the observed $\tau_{DA}$ values, and $\mu_p$ and $\mu_n$ are the mean $\tau_{DA}$ values of the positive and negative controls. To make this metric less sensitive to strong outliers, we utilized the normalized median absolute deviation (1.4826*MAD) and median in place of the standard deviation and mean, respectively [91].

Fluorescent compounds were flagged as potential false positives due to interference from compound fluorescence by a set of stringent fluorescent compound filters based on analysis of the spectral waveforms of each well from the NCC screen [46,47]. After removal of fluorescent compounds, a histogram of the FRET distribution from all compounds in the screen was plotted and fit to a Gaussian curve to obtain the mean (µ) and standard deviation (σ, SD). A hit was defined as a compound that decreased the FRET efficiency by more than five times the standard deviation (5SD) relative to the mean Five reproducible hits, MK-886 (Cayman Chemical), Benzbromarone (Millipore Sigma), Bumetanide (Millipore Sigma), Torsemide (Millipore Sigma) and Triclosan (Millipore Sigma) were purchased.

Protein Purification

Full-length 2N4R WT tau proteins were purified from *E. coli* using previously published protocols [62]. Full-length tau was expressed with a cleavable His-tag. After elution from a nickel column, cleavage of the His-tag was achieved by incubation with tobacco etch virus (TEV) protease at room temperature for at least 4 hours, followed by passing through the His-tag column again to separate cleaved and uncleaved protein and remove the TEV. Final purification was performed by size-exclusion chromatography and the purity of the proteins was assessed by 4%-15% SDS-PAGE gels (Bio-Rad) under reducing conditions, followed by Coomassie staining. Fractions of pure proteins from the gels were pooled together and the protein stock concentrations were measured using the BCA assay (Thermo Fisher Scientific). Full-length 2N4R P301L tau protein was purchased (rPeptide).

Surface Plasmon Resonance (SPR) Binding Assay

Binding affinity between full-length 2N4R WT or P301L tau and the hit compounds were determined by SPR analysis using BIAcore 5200. Recombinant tau proteins were immobilized on the CM5 sensor chip (Biacore, GE Healthcare) via amine coupling. Briefly, the dextran surface was activated with a 1:1 mixture of 0.4 M 1-ethyl-3-(3-dimethylaminopropyl)carbodiimide hydrochloride and 0.1 M N-hydroxysuccinimide. WT or P301L tau proteins (20 μg/ml) in 10 mM sodium acetate at pH 3.5-4.0 were flowed past a working surface before blocking the remaining activated carboxymethyl groups with 1 M ethanolamine at pH 8.5 to achieve a level of 1200 RU suitable for binding analysis. The reference surface was activated and reacted with only ethanolamine.

For direct binding assays to the tau proteins, hit compounds at eight different concentrations (1 nM to 5 μM), as well as DMSO-only controls, were prepared in HEPES-EP containing a total of 2% DMSO. The samples were injected over both the reference and tau immobilized surfaces at 10 μl/min for 180 seconds and dissociated in glycine-HCl pH 2.5. All the samples, along with blanks from buffer and DMSO-only controls, were measured on a 96-well microplate (Biacore, GE Healthcare) at 25° C. Reflectivity response data points were extracted from response curves at 5 seconds prior to the end of the injection to determine steady-state binding. All the data were double referenced with blanks using standard procedures with Biacore 5200 Evaluation Software v1.0.

FRET Dose-Response Assay

MK-886, which shows direct binding to tau proteins and the strongest change in FRET, was tested in a FRET dose-response assay. The compound was dissolved in DMSO to make a 10 mM stock solution, which was serially diluted in 96-well mother plates. MK-886 was screened at different concentrations (1 nM to 10 μM). Compound (1 μl) was transferred from the mother plates into assay plates using a Mosquito HV liquid handler (TTP Labtech Ltd, UK). Three days prior to conducting the assays, the stable GFP-tau-RFP cells and GFP-32AA-RFP control cells were expanded in two 225 cm² flasks (Corning). The preparations for WT or P301L tau-GFP/RFP FRET biosensors and the soluble GFP/RFP controls cells were carried out similar as above.

Cell Cytotoxicity Assay

Cell cytotoxicity was measured using the CytoTox-Glo (Promega Corporation) luminescence assay kit. SH-SY5Y human neuroblastoma cells were plated at a density of $1 \times 10^6$ cells/well in a 6-well plate (Corning) and transfected with unlabeled full-length 2N4R P301L tau or equivalent vector-only control for 24 hours. The transfected cells were then plated at a density of 10000 cells/well in white solid 96-well plate (Corning) with a total volume of 100 μl, followed by treatment with MK-886 at eight different concentrations (1 nM to 2 μM), as well as DMSO-only controls, for another 72 hours. After incubation, 50 μl of CytoTox-Glo Cytotoxicity Assay Reagent was added to all wells followed by mixing by orbital shaking and incubation for 15 minutes at room temperature. The first luminescence reading was measured using a Cytation3 Cell Imaging Multi-Mode Reader luminometer (BioTek). 50 μl of Lysis Reagent with 1% Triton X-100 was then added, followed by incubation at room temperature for 15 min, and luminescence was measured again using the luminometer. Cell cytotoxicity was calculated following the manufacturer protocol. Effect of MK-886 on the suppressors of inhibitors of apoptosis (IAPB) (YM-155 and UC-112) was tested with untransfected SH-SY5Y cells plated in white solid 96-well plate with treatment of YM-155 (1 μM) or UC-112 (1 μM) in the absence or presence of MK-886 (0.5, 1 or 2 μM).

Western Blot Analysis

To test the expression of tau FRET biosensors, HEK293 cells were plated in a 100 mm plate at a density of $5 \times 10^6$ cells/plate and transfected with tau-GFP/RFP (tau FRET biosensor) plasmid. To test the clearance and phosphorylation state of tau in the cytotoxicity assay, SH-SY5Y cells were plated in a six-well plate at a density of $1 \times 10^6$ cells/well and transfected with unlabeled P301L tau plasmid for 24 hours followed by treatment of MK-886 (2 μM) for 72 hours. In both cases, cells were lysed for 30 minutes on ice with radioimmunoprecipitation assay (RIPA) lysis buffer (Pierce RIPA buffer, Thermo Fisher Scientific) containing 1% protease inhibitor (Clontech, Mountain View, Calif.) and 1% phosphatase inhibitors (Millipore Sigma), and centrifuged at 15,000 g at 4° C. for 15 min. The total protein concentration of lysates was determined by bicinchoninic acid (BCA) assay (Pierce), and equal amounts of total protein (60 μg) were mixed with 4× Bio-Rad sample buffer and loaded onto 4%-15% Trisglycine sodium dodecyl sulfate-polyacrylamide gel electrophoresis (SDS-PAGE) gels (Bio-Rad, Hercules, Calif.). Proteins were transferred to polyvinylidene fluoride (PVDF) membrane (Immobilon-FL, EMD Millipore, Billerica, Mass.) and probed using antibodies against tau (Tau-5, Thermo Fisher Scientific) or antibody specific to Serine 396 of tau (Phospho-Tau 5396, Thermo Fisher Scientific) with β-actin (ab8227, Abcam, Cambridge, Mass.) used as loading control. Blots were quantified on the Odyssey scanner (LI-COR Biosciences, Lincoln, Nebr.).

Protein Labelling and Single-Molecule FRET (smFRET) Measurements

For site-specific labeling with maleimide-reactive fluorophores, cysteine residues were introduced using QuikChange Site-Directed Mutagenesis (Stratagene). Naturally occurring cysteines were mutated to serines. Labelling positions were selected to roughly mark the boundaries of the N-terminal domain or the proline-rich and microtubule-binding region of tau. Tau protein was purified as described above and labeled immediately following purification following published protocols [62]. Briefly, the protein (typically 200 μL of ~100 μM protein) was incubated with 1 mM DTT for 30 minutes at room temperature followed by exchange into labeling buffer (20 mM Tris pH 7.4, 50 mM NaCl, and 6 M guanidine HCl) to remove DTT. The protein was incubated with the donor fluorophore, Alexa Fluor 488 maleimide (Invitrogen), at a protein to dye ratio of 2:1 at room temperature for one hour with stirring. The acceptor dye, Alexa Fluor 594 maleimide (Invitrogen), was added at a 5-fold molar excess and incubated overnight at 4° C. with stirring. Excess dye was then removed by buffer-exchanging the labeled solution into 20 mM Tris (pH 7.4) and 50 mM NaCl buffer using Amicon concentrators (Millipore) and then passed over two coupled HiTrap Desalting Columns (GE Life Sciences).

Single-molecule FRET measurements were carried out using ~30 pM of labelled tau in phosphate buffer (40 mM potassium phosphate, 50 mM KCl, pH 7.4) in 8-chambered Nunc coverslips (ThermoFisher) passivated with poly(ethylene glycol) poly(L-lysine) (PEG-PLL) to reduce protein adsorption to the chambers. Control measurements included DMSO to match the concentration in samples containing MK-886. Measurements were made on a MicroTime 200 time-resolved confocal microscope (Picoquant) in pulsed interleaved excitation FRET (PIE-FRET) mode. Laser power from 485 and 561 nm lasers, operated at 40 MHz pulse rate, was adjusted to ~30 µW before sample illumination. Fluorescence emission was collected through the objective and passed through a 150 µm diameter pinhole. Photons were separated by an HQ585LP dichroic in combination with ET525/50M and HQ600LP filters and detected by avalanche photodiodes. Photon traces were collected in 1 ms time bins for one hour. A cutoff of 25 counts/ms was applied to discriminate between bursts arising from fluorescently labeled protein and background noise. No bursts were identified in photon traces with DMSO only and MK-886 only when this criterion was applied. The FRET efficiency (ETeff) was calculated using SymphoTime 64 software. SmFRET histograms were fit with Gaussian distributions to determine the peak ETeff values. Alignment of instrument and analysis were verified using 10 base pair, 14 base pair and 18 base pair dsDNA standards.

Thioflavin-S(ThS) Assay

HEK293 cells were transfected with tau-RFP (at equivalent DNA concentration as used in the tau FRET biosensor) for 48 hours prior to the addition of tau preformed fibrils (PFF). Tau-GFP was not used as it would interfere with the thioflavin-S(ThS) signal. To make the PFF, 100 µl of purified tau proteins (10 µM) with DTT (5 mM) and heparin (0.4 mg/ml) were first incubated for 120 hours at 37° C. and shook at 1000 rpm in a thermal shaker (Thermo Fisher Scientific). After incubation, the sample was subjected to ultracentrifugation at 80,000 rpm for 30 minutes. The pellet was collected and sonicated to break up the fibrils into smaller pieces. The concentration of the fibrils was then measured by BCA. The sonicated fibrils were then treated to the transfected cells at a concentration of 40 µg/ml for 24 hours before conducting the ThS assay. Thioflavin-S(ThS, Millipore Sigma, product no. T1892) was dissolved in PBS buffer and was filtered through a 0.2 µm syringe filter to make a stock solution of 2.5 mM. For the ThS assay, cells were fixed with 1 ml of 4% paraformaldehyde in TBS for 15 minutes followed by washing with 1 ml of TBS for 5 minutes twice. After fixing, cells were permeabilized with 1 ml of 1% Triton in TBS for 5 minutes, followed by washing with 1 ml of TBS for 5 minutes twice. After permeabilization, cells were then treated with 0.002% ThS in TBS and incubate in the dark for 20 minutes. Cells were then washed twice with 50% ethanol for 10 minutes each and finally washed twice with TBS for 5 minutes each. Cells were then imaged with a fluorescence microscope using EVOS-FL cell imaging systems at 20× magnification. Mean fluorescence intensity for each image was quantified using ImageJ and values were normalized to untransfected controls.

Thioflavin-T (ThT) Assay

Thioflavin-T (ThT, Sigma, product no. T3516) was dissolved in PBS buffer and was filtered through a 0.2 µm syringe filter to make a stock solution of 2.5 mM. ThT was then diluted to 20 prior to addition to the tau proteins. The samples for ThT measurements were prepared by mixing 25 µl of 20 µM tau proteins with 25 µl of 20 µM of ThT, resulting in final concentrations of 10 µM tau proteins and 10 µM ThT. DTT (5 mM) and heparin (0.4 mg/ml) were then added to the samples; a control sample lacked addition of heparin. Lastly, the samples were treated with MK-886 (0.5 µM or 5 µM) and gossypetin (50 µM) with DMSO added to the no-compound controls. The ThT samples (50 µl each) were transferred to a black 96-well non-binding surface microplate with clear bottom (Corning product no. 3655) and incubated at 37° C. with mild shaking (200 rpm) in the Cytation 3 plate reader. The ThT fluorescence was measured by the Cytation 3 plate reader through the bottom of the plate with excitation filter of 440 nm and emission filter of 480 nm. Readings were acquired every 20 minutes for a total of 120 hours.

Statistical Analysis

Data are shown as mean±standard deviation unless stated otherwise. Statistical analysis was performed by a two-tailed unpaired t test (Student's t test) using GraphPad Software to determine statistical significance for all experiments. Values of $P<0.05$ were considered statistically significant. GraphPad style in using asterisks to denote P values in figures was used (*$P<0.05$, $P<0.01$, *$P<0.001$, ****$P<0.0001$ and n.s. indicates not significant).

CITATIONS

1. Wood J G, Mirra S S, Pollock N J, Binder L I. Neurofibrillary tangles of Alzheimer disease share antigenic determinants with the axonal microtubule-associated protein tau (tau). *Proceedings of the National Academy of Sciences of the United States of America.* 1986; 83(11): 4040-4043.
2. Orr M E, Sullivan A C, Frost B. A Brief Overview of Tauopathy: Causes, Consequences, and Therapeutic Strategies. *Trends in Pharmacological Sciences.* 2017; 38(7): 637-648.
3. Cummings J, Lee G, Ritter A, Zhong K. Alzheimer's disease drug development pipeline: 2018. *Alzheimer's & Dementia: Translational Research & Clinical Interventions.* 2018; 4:195-214.
4. Medina M. An Overview on the Clinical Development of Tau-Based Therapeutics. *International Journal of Molecular Sciences.* 2018; 19(4):1160.
5. Brunden K R, Trojanowski J Q, Lee V M Y. Advances in tau-focused drug discovery for Alzheimer's disease and related tauopathies. *Nature reviews Drug discovery.* 2009; 8(10):783-793.
6. Giacobini E, Gold G. Alzheimer disease therapy—moving from amyloid-β to tau. *Nature Reviews Neurology.* 2013; 9:677.
7. Avila et al., Role of Tau Protein in Both Physiological and Pathological Conditions. *Physiological Reviews.* 2004; 84(2):361-384.
8. Bramblett G T, Goedert M, Jakes R, Merrick S E, Trojanowski J Q, Lee V M Y. Abnormal tau phosphorylation at Ser396 in alzheimer's disease recapitulates development and contributes to reduced microtubule binding. *Neuron.* 1993; 10(6):1089-1099.
9. Bubber P, Haroutunian V, Fisch G, Blass J P, Gibson G E. Mitochondrial abnormalities in Alzheimer brain: mechanistic implications. *Annals of neurology.* 2005; 57(5):695-703.
10. Sultana R, Butterfield D A. Oxidative modification of brain proteins in Alzheimer's disease: perspective on future studies based on results of redox proteomics studies. *Journal of Alzheimer's disease: JAD.* 2013; 33 Suppl 1:S243-251.
11. Majid T, Ali Y O, Venkitaramani D V, Jang M-K, Lu H-C, Pautler R G. In vivo axonal transport deficits in a mouse model of fronto-temporal dementia. *NeuroImage: Clinical.* 2014; 4:711-717.
12. Sahara N, Maeda S, Takashima A. Tau Oligomerization: A Role for Tau Aggregation Intermediates Linked to Neurodegeneration. *Current Alzheimer Research.* 2008; 5(6):591-598.
13. Ballatore C, Lee V M Y, Trojanowski J Q. Tau-mediated neurodegeneration in Alzheimer's disease and related disorders. *Nature Reviews Neuroscience.* 2007; 8:663.

14. Gerson J E, Castillo-Carranza D L, Kayed R. Advances in Therapeutics for Neurodegenerative Tauopathies: Moving toward the Specific Targeting of the Most Toxic Tau Species. *ACS Chemical Neuroscience.* 2014; 5(9):752-769.
15. Maeda S, Sahara N, Saito Y, Murayama S, Ikai A, Takashima A. Increased levels of granular tau oligomers: An early sign of brain aging and Alzheimer's disease. *Neuroscience Research.* 2006; 54(3):197-201.
16. Wittmann C W, Wszolek M F, Shulman J M, Salvaterra P M, Lewis J, Hutton M, et al. Tauopathy in *Drosophila*: Neurodegeneration Without Neurofibrillary Tangles. *Science.* 2001; 293(5530):711-714.
17. Santacruz K, Lewis J, Spires T, Paulson J, Kotilinek L, Ingelsson M, et al. Tau suppression in a neurodegenerative mouse model improves memory function. *Science.* 2005; 309(5733):476-481.
18. Berger Z, Roder H, Hanna A, Carlson A, Rangachari V, Yue M, et al. Accumulation of Pathological Tau Species and Memory Loss in a Conditional Model of Tauopathy. *The Journal of Neuroscience.* 2007; 27(14):3650-3662.
19. Lasagna-Reeves C A, Castillo-Carranza D L, Sengupta U, Sarmiento J, Troncoso J, Jackson G R, et al. Identification of oligomers at early stages of tau aggregation in Alzheimer's disease. *The FASEB Journal.* 2012; 26(5): 1946-1959.
20. Flach K, Hilbrich I, Schiffmann A, Gaertner U, Krueger M, Leonhardt M, et al. Tau oligomers impair artificial membrane integrity and cellular viability. *Journal of Biological Chemistry.* 2012.
21. Ward S M, Himmelstein D S, Lancia J K, Binder L I. Tau oligomers and tau toxicity in neurodegenerative disease. *Biochemical Society transactions.* 2012; 40(4):667-671.
22. Nath A, Sammalkorpi M, DeWitt D C, Trexler A J, Elbaum-Garfinkle S, O'Hern C S, et al. The conformational ensembles of α-synuclein and tau: combining single-molecule FRET and simulations. *Biophysical journal.* 2012; 103(9):1940-1949.
23. Akoury E, Gajda M, Pickhardt M, Biernat J, Soraya P, Griesinger C, et al. Inhibition of Tau Filament Formation by Conformational Modulation. *Journal of the American Chemical Society.* 2013; 135(7):2853-2862.
24. Gerson J E, Mudher A, Kayed R. Potential mechanisms and implications for the formation of tau oligomeric strains. *Critical Reviews in Biochemistry and Molecular Biology.* 2016; 51(6):482-496.
25. Weaver C L, Espinoza M, Kress Y, Davies P. Conformational change as one of the earliest alterations of tau in Alzheimer's disease. *Neurobiology of Aging.* 2000; 21(5): 719-727.
26. Sharma A M, Thomas T L, Woodard D R, Kashmer O M, Diamond M I. Tau monomer encodes strains. *eLife.* 2018; 7:e37813.
27. Mirbaha H, Chen D, Morazova O A, Ruff K M, Sharma A M, Liu X, et al. Inert and seed-competent tau monomers suggest structural origins of aggregation. *eLife.* 2018; 7:e36584.
28. Huang R Y-C, Iacob R E, Sankaranarayanan S, Yang L, Ahlijanian M, Tao L, et al. Probing Conformational Dynamics of Tau Protein by Hydrogen/Deuterium Exchange Mass Spectrometry. *Journal of The American Society for Mass Spectrometry.* 2018; 29(1):174-182.
29. Gotz J, Xia D, Leinenga G, Chew Y L, Nicholas H. What Renders TAU Toxic. *Frontiers in neurology.* 2013; 4:72-72.
30. Gendron T F, Petrucelli L. The role of tau in neurodegeneration. *Molecular Neurodegeneration.* 2009; 4(1):13.
31. Kopeikina K J, Hyman B T, Spires-Jones T L. Soluble forms of tau are toxic in Alzheimer's disease. *Translational neuroscience.* 2012; 3(3):223-233.
32. Lo Cascio F, Kayed R. Azure C Targets and Modulates Toxic Tau Oligomers. *ACS Chemical Neuroscience.* 2018; 9(6): 1317-1326.
33. Wischik C M, Edwards P C, Lai R Y, Roth M, Harrington C R. Selective inhibition of Alzheimer disease-like tau aggregation by phenothiazines. *Proceedings of the National Academy of Sciences of the United States of America.* 1996; 93(20):11213-11218.
34. Wobst H J, Sharma A, Diamond M I, Wanker E E, Bieschke J. The green tea polyphenol (−)-epigallocatechin gallate prevents the aggregation of tau protein into toxic oligomers at substoichiometric ratios. *FEBS Letters.* 2015; 589(1):77-83.
35. Rane J S, Bhaumik P, Panda D. Curcumin Inhibits Tau Aggregation and Disintegrates Preformed Tau Filaments in vitro. *Journal of Alzheimer's Disease.* 2017; 60(3):999-1014.
36. Wang P, Lo Cascio F, Gao J, Kayed R, Huang X. Binding and neurotoxicity mitigation of toxic tau oligomers by synthetic heparin like oligosaccharides. *Chemical Communications.* 2018; 54(72):10120-10123.
37. Taniguchi S, Suzuki N, Masuda M, Hisanaga S-i, Iwatsubo T, Goedert M, et al. Inhibition of Heparin-induced Tau Filament Formation by Phenothiazines, Polyphenols, and Porphyrins. *Journal of Biological Chemistry.* 2005; 280(9):7614-7623.
38. Baggett D W, Nath A. The Rational Discovery of a Tau Aggregation Inhibitor. *Biochemistry.* 2018; 57(42):6099-6107.
39. Gauthier S, Feldman H H, Schneider L S, Wilcock G K, Frisoni G B, Hardlund J H, et al. Efficacy and safety of tau-aggregation inhibitor therapy in patients with mild or moderate Alzheimer's disease: a randomised, controlled, double-blind, parallel-arm, phase 3 trial. *Lancet.* 2016; 388(10062):2873-2884.
40. Cowan C M, Mudher A. Are tau aggregates toxic or protective in tauopathies? *Frontiers in neurology.* 2013; 4:114-114.
41. Guzmán-Martinez L, Farias G A, Maccioni R B. Tau oligomers as potential targets for Alzheimer's diagnosis and novel drugs. *Frontiers in neurology.* 2013; 4:167-167.
42. Davidowitz E, Chatterjee I, Moe J. Targeting tau oligomers for therapeutic development for Alzheimer's disease and tauopathies. *Curr Topics Biotechnol.* 2008; 4:47-64.
43. Kfoury N, Holmes B B, Jiang H, Holtzman D M, Diamond M I. Trans-cellular propagation of Tau aggregation by fibrillar species. *J Biol Chem.* 2012; 287(23): 19440-19451.
44. Petersen K J, Peterson K C, Muretta J M, Higgins S E, Gillispie G D, Thomas D D. Fluorescence lifetime plate reader: Resolution and precision meet high-throughput. *The Review of Scientific Instruments.* 2014; 85(11): 113101.
45. Gruber S J, Cornea R L, Li J, Peterson K C, Schaaf T M, Gillispie G D, et al. Discovery of enzyme modulators via high-throughput time-resolved FRET in living cells. *Journal of Biomolecular Screening.* 2014; 19(2):215-222.
46. Lo C H, Vunnam N, Lewis A K, Chiu T-L, Brummel B E, Schaaf T M, et al. An Innovative High-Throughput Screening Approach for Discovery of Small Molecules That Inhibit TNF Receptors. *SLAS DISCOVERY: Advancing Life Sciences R & D.* 2017; 22(8):950-961.

47. Schaaf T M, Peterson K C, Grant B D, Bawaskar P, Yuen S, Li J, et al. High-Throughput Spectral and Lifetime-Based FRET Screening in Living Cells to Identify Small-Molecule Effectors of SERCA. *SLAS DISCOVERY: Advancing Life Sciences R & D.* 2017; 22(3):262-273.

48. Lo C H, Schaaf T M, Grant B D, Lim C K-W, Bawaskar P, Aldrich C C, et al. Noncompetitive inhibitors of TNFR1 probe conformational activation states. *Science Signaling.* 2019; 12(592): eaav5637.

49. Kuret J, Congdon E E, Li G, Yin H, Yu X, Zhong Q. Evaluating triggers and enhancers of tau fibrillization. *Microscopy Research and Technique.* 2005; 67(3-4):141-155.

50. Ko L-w, Deture M, Sahara N, Chihab R, Yen S-H. *Cellular Models for Tau Filament Assembly.* Vol 192003.

51. Chirita C N, Congdon E E, Yin H, Kuret J. Triggers of Full-Length Tau Aggregation: A Role for Partially Folded Intermediates. *Biochemistry.* 2005; 44(15):5862-5872.

52. Ferrari A, Hoerndli F, Baechi T, Nitsch R M, Gotz J. β-Amyloid Induces Paired Helical Filament-like Tau Filaments in Tissue Culture. *Journal of Biological Chemistry.* 2003; 278(41):40162-40168.

53. Tak H, Haque M M, Kim M J, Lee J H, Baik J H, Kim Y, et al. Bimolecular fluorescence complementation; lighting-up tau-tau interaction in living cells. *PLoS One.* 2013; 8(12).

54. Sahara N, Lewis J, DeTure M, McGowan E, Dickson D W, Hutton M, et al. Assembly of tau in transgenic animals expressing P301L tau: alteration of phosphorylation and solubility. *Journal of neurochemistry.* 2002; 83(6):1498-1508.

55. Zhao Z, Ho L, Suh J, Qin W, Pyo H, Pompl P, et al. A role of P301L tau mutant in anti-apoptotic gene expression, cell cycle and apoptosis. *Molecular and Cellular Neuroscience.* 2003; 24(2):367-379.

56. Schulz K L, Eckert A, Rhein V, Mai S, Haase W, Reichert A S, et al. A New Link to Mitochondrial Impairment in Tauopathies. *Molecular Neurobiology.* 2012; 46(1):205-216.

57. Mancini J A, Prasit P, Coppolino M G, Charleson P, Leger S, Evans J F, et al. 5-Lipoxygenase-activating protein is the target of a novel hybrid of two classes of leukotriene biosynthesis inhibitors. *Molecular Pharmacology.* 1992; 41(2):267-272.

58. Chu J, Li J-G, Ceballos-Diaz C, Golde T, Pratico D. The influence of 5-lipoxygenase on Alzheimer's disease-related tau pathology: in vivo and in vitro evidence. *Biological psychiatry.* 2013; 74(5):321-328.

59. Valera E, Dargusch R, Maher P A, Schubert D. Modulation of 5-lipoxygenase in proteotoxicity and Alzheimer's disease. *The Journal of neuroscience: the official journal of the Society for Neuroscience.* 2013; 33(25): 10512-10525.

60. Klegeris A, McGeer P L. Toxicity of human monocytic THP-1 cells and microglia toward SH-SY5Y neuroblastoma cells is reduced by inhibitors of 5-lipoxygenase and its activating protein FLAP. *Journal of Leukocyte Biology.* 2003; 73(3):369-378.

61. Xiao M, Li W. Recent Advances on Small-Molecule Survivin Inhibitors. *Curr Med Chem.* 2015; 22(9):1136-1146.

62. Elbaum-Garfinkle S, Rhoades E. Identification of an aggregation-prone structure of tau. *Journal of the American Chemical Society.* 2012; 134(40):16607-16613.

63. Jeganathan S, von Bergen M, Brutlach H, Steinhoff H J, Mandelkow E. Global hairpin folding of tau in solution. *Biochemistry.* 2006; 45(7):2283-2293.

64. Verheyen A, Diels A, Dijkmans J, Oyelami T, Meneghello G, Mertens L, et al. Using Human iPSC-Derived Neurons to Model TAU Aggregation. *PLOS ONE.* 2016; 10(12):e0146127.

65. Lee H-K, Velazquez Sanchez C, Chen M, Morin P J, Wells J M, Hanlon E B, et al. Three Dimensional Human Neuro-Spheroid Model of Alzheimer's Disease Based on Differentiated Induced Pluripotent Stem Cells. *PloS one.* 2016; 11(9):e0163072-e0163072.

66. Raja W K, Mungenast A E, Lin Y-T, Ko T, Abdurrob F, Seo J, et al. Self-Organizing 3D Human Neural Tissue Derived from Induced Pluripotent Stem Cells Recapitulate Alzheimer's Disease Phenotypes. *PloS one.* 2016; 11(9):e0161969-e0161969.

67. Kjaergaard M, Dear A J, Kundel F, Qamar S, Meisl G, Knowles TPJ, et al. Oligomer Diversity during the Aggregation of the Repeat Region of Tau. *ACS chemical neuroscience.* 2018; 9(12):3060-3071.

68. Dujardin S, Bégard S, Caillierez R, Lachaud C, Carrier S, Lieger S, et al. Different tau species lead to heterogeneous tau pathology propagation and misfolding. *Acta Neuropathologica Communications.* 2018; 6(1):132.

69. Zhao X, Kotilinek L A, Smith B, Hlynialuk C, Zahs K, Ramsden M, et al. Caspase-2 cleavage of tau reversibly impairs memory. *Nature Medicine.* 2016; 22(11):1268-1276.

70. Chen W, Young L J, Lu M, Zaccone A, Strohl F, Yu N, et al. Fluorescence Self-Quenching from Reporter Dyes Informs on the Structural Properties of Amyloid Clusters Formed in Vitro and in Cells. *Nano Letters.* 2017; 17(1): 143-149.

71. Romo T D, Lewis A K, Braun A R, Grossfield A, Sachs J N. Minimal Nucleation State of alpha-Synuclein Is Stabilized by Dynamic Threonine-Water Networks. *ACS Chem Neurosci.* 2017; 8(9):1859-1864.

72. Tuttle M D, Comellas G, Nieuwkoop A J, Covell D J, Berthold D A, Kloepper K D, et al. Solid-state NMR structure of a pathogenic fibril of full-length human alpha-synuclein. *Nature structural & molecular biology.* 2016; 23(5):409-415.

73. Rodriguez J A, Ivanova M I, Sawaya M R, Cascio D, Reyes F E, Shi D, et al. Structure of the toxic core of alpha-synuclein from invisible crystals. *Nature.* 2015; 525(7570):486-490.

74. Muretta; J M, Kyrychenko; A, Kast; ASLDJ, Gillispie; G D, Thomas D D. High-performance time-resolved fluorescence by direct waveform recording. *Review of Scientific Instruments.* 2010; 81(10): 103101.

75. Zhang S, Wang C, Lu J, Ma X, Liu Z, Li D, et al. In-Cell NMR Study of Tau and MARK2 Phosphorylated Tau. *International Journal of Molecular Sciences.* 2018; 20(1): 90.

76. Theillet F X, Binolfi A, Bekei B, Martorana A, Rose H M, Stuiver M, et al. Structural disorder of monomeric alpha-synuclein persists in mammalian cells. *Nature.* 2016; 530(7588):45-50.

77. Zigoneanu I G, Pielak G J. Interaction of alpha-synuclein and a cell penetrating fusion peptide with higher eukaryotic cell membranes assessed by (1)(9)F NMR. *Molecular pharmaceutics.* 2012; 9(4):1024-1029.

78. Kovacs G G. Invited review: Neuropathology of tauopathies: principles and practice. *Neuropathology and Applied Neurobiology.* 2015; 41(1):3-23.

79. Devi G, Scheltens P. Heterogeneity of Alzheimer's disease: consequence for drug trials? *Alzheimer's Research & Therapy.* 2018; 10(1):122.

80. Ghetti B, Oblak A L, Boeve B F, Johnson K A, Dickerson B C, Goedert M. Invited review: Frontotemporal dementia caused by microtubule-associated protein tau gene (MAPT) mutations: a chameleon for neuropathology and neuroimaging. *Neuropathology and Applied Neurobiology*. 2015; 41(1):24-46.

81. Mondragon-Rodriguez S, Perry G, Zhu X, Moreira P I, Acevedo-Aquino M C, Williams S. Phosphorylation of tau protein as the link between oxidative stress, mitochondrial dysfunction, and connectivity failure: implications for Alzheimer's disease. *Oxid Med Cell Longev*. 2013; 2013:940603.

82. Rhein V, Song X, Wiesner A, Ittner L M, Baysang G, Meier F, et al. Amyloid-beta and tau synergistically impair the oxidative phosphorylation system in triple transgenic Alzheimer's disease mice. *Proc Natl Acad Sci USA*. 2009; 106(47):20057-20062.

83. Ebneth A, Godemann R, Stamer K, Illenberger S, Trinczek B, Mandelkow E. Overexpression of tau protein inhibits kinesin-dependent trafficking of vesicles, mitochondria, and endoplasmic reticulum: implications for Alzheimer's disease. *The Journal of cell biology*. 1998; 143(3):777-794.

84. Yasar S, Xia J, Yao W, Furberg C D, Xue Q-L, Mercado C I, et al. Antihypertensive drugs decrease risk of Alzheimer disease: Ginkgo Evaluation of Memory Study. *Neurology*. 2013; 81(10):896-903.

85. Muraya N, Kadowaki D, Miyamura S, Kitamura K, Uchimura K, Narita Y, et al. Benzbromarone Attenuates Oxidative Stress in Angiotensin II- and Salt-Induced Hypertensive Model Rats. *Oxid Med Cell Longev*. 2018; 2018:7635274.

86. Wang C, Yu Z, Shi X, Tang X, Wang Y, Wang X, et al. Triclosan Enhances the Clearing of Pathogenic Intracellular *Salmonella* or *Candida albicans* but Disturbs the Intestinal Microbiota through mTOR-Independent Autophagy. *Frontiers in cellular and infection microbiology*. 2018; 8:49-49.

87. Moussaud S, Jones D R, Moussaud-Lamodiere E L, Delenclos M, Ross O A, McLean P J. Alpha-synuclein and tau: teammates in neurodegeneration? *Mol Neurodegener*. 2014; 9:43.

88. Zacharias D A, Violin J D, Newton A C, Tsien R Y. Partitioning of lipid-modified monomeric GFPs into membrane microdomains of live cells. *Science*. 2002; 296(5569):913-916.

89. Schaaf T, Li A, Grant B, Peterson K, Yuen S, Bawaskar P, et al. Red-Shifted FRET Biosensors for High-Throughput Fluorescence Lifetime Screening. *Biosensors*. 2018; 8(4):99.

90. Zhang J H, Chung T D, Oldenburg K R. A Simple Statistical Parameter for Use in Evaluation and Validation of High Throughput Screening Assays. *Journal of biomolecular screening*. 1999; 4(2):67-73.

91. Birmingham A, Selfors L M, Forster T, Wrobel D, Kennedy C J, Shanks E, et al. Statistical methods for analysis of high-throughput RNA interference screens. *Nature methods*. 2009; 6(8):569-575.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for identifying a compound that alters fluorescence resonance energy transfer (FRET) of a protein comprising:
   providing a genetically engineered cell comprising two tau proteins,
      wherein a first tau protein comprises a first heterologous domain, wherein the first heterologous domain comprises a first probe,
      wherein a second tau protein comprises a second heterologous domain, wherein the second heterologous domain comprises a second probe;
      wherein the first and second tau proteins form an oligomer in the cell;
   contacting the cell with a test compound to form a mixture; and
   measuring fluorescence lifetime of the first probe, the second probe, or the combination thereof.

2. The method of claim 1 wherein a difference between the fluorescence lifetime in the presence of the test compound and the fluorescence lifetime in the absence of the test compound indicates that the test compound alters the FRET of the first tau protein, the second tau protein, or a combination thereof.

3. The method of claim 1 wherein the cell is substantially free of fibrillar tau proteins.

4. The method of claim 1 wherein the first heterologous domain is located at the amino-terminal end of the first tau protein and the second heterologous domain is located at the carboxy-terminal end of the second tau protein.

5. The method of claim 1 wherein the first probe and the second probe are a donor-acceptor pair.

6. The method of claim 5 wherein the measuring comprises capturing fluorescence lifetime waveforms emitted by the donor probe, the acceptor probe, or a combination thereof.

7. The method of claim 5 wherein the fluorescence lifetime of the donor probe, the acceptor probe, or a combination thereof, is changed in the presence of the test compound.

8. The method of claim 1 wherein the measuring of the fluorescence lifetime comprises high throughput screening.

9. The method of claim 1 wherein the first and second tau proteins are different isoforms.

10. The method of claim 1 wherein the first tau protein, the second tau protein, or both tau proteins comprise a mutation.

11. A method for identifying a compound that alters fluorescence resonance energy transfer (FRET) of a protein comprising:
   providing a genetically engineered cell comprising a tau protein,
      wherein the tau protein comprises two heterologous domains, wherein a first heterologous domain comprises a first probe, and wherein a second heterologous domain comprises a second probe, and
      wherein the tau protein forms an oligomer in the cell;
   contacting the cell with a test compound to form a mixture; and
   measuring fluorescence lifetime of the first probe, the second probe, or the combination thereof.

12. The method of claim 11 wherein a difference between the fluorescence lifetime in the presence of the test compound and the fluorescence lifetime in the absence of the test compound indicates that the test compound alters the FRET of the tau protein.

13. The method of claim 11 wherein the cell is substantially free of fibrillar tau proteins.

14. The method of claim 11 wherein the first heterologous domain is located at the amino-terminal end of the tau protein and the second heterologous domain is located at the carboxy-terminal end of the tau protein.

15. The method of claim 11 wherein the first probe and the second probe are a donor-acceptor pair.

16. The method of claim 15 wherein the measuring comprises capturing fluorescence lifetime waveforms emitted by the donor probe, the acceptor probe, or a combination thereof.

17. The method of claim 15 wherein the fluorescence lifetime of the donor probe, the acceptor probe, or a combination thereof, is changed in the presence of the test compound.

18. The method of claim 15 wherein the fluorescence lifetime of the donor probe is unchanged in the presence of the test compound.

19. The method of claim 11 wherein the measuring of the fluorescence lifetime comprises high throughput screening.

20. The method of claim 11 wherein the tau protein is selected from isoform 2N4R, isoform 2N3R, isoform 1N4R, isoform 1N3R, isoform 0N4R, or isoform 0N3R.

* * * * *